(12) United States Patent
Strittmatter

(10) Patent No.: US 11,241,434 B2
(45) Date of Patent: *Feb. 8, 2022

(54) COMPOSITIONS AND METHODS FOR IMPROVING COGNITION IN A SUBJECT

(71) Applicant: Yale University, New Haven, CT (US)

(72) Inventor: Stephen M. Strittmatter, Guilford, CT (US)

(73) Assignee: Yale Uninversity, New Haven, CT (US)

( * ) Notice: Subject to any disclaimer, the term of this patent is extended or adjusted under 35 U.S.C. 154(b) by 137 days.

This patent is subject to a terminal disclaimer.

(21) Appl. No.: 16/820,060

(22) Filed: Mar. 16, 2020

(65) Prior Publication Data
US 2020/0215070 A1 Jul. 9, 2020

Related U.S. Application Data

(63) Continuation-in-part of application No. 14/272,874, filed on May 8, 2014, now Pat. No. 10,660,957.

(60) Provisional application No. 61/834,595, filed on Jun. 13, 2013.

(51) Int. Cl.
*A61K 31/517* (2006.01)
*A61P 25/28* (2006.01)

(52) U.S. Cl.
CPC ............ *A61K 31/517* (2013.01); *A61P 25/28* (2018.01)

(58) Field of Classification Search
CPC .............................. A61K 31/517; A61P 25/28
See application file for complete search history.

(56) References Cited

U.S. PATENT DOCUMENTS

2008/0008752 A1 1/2008 Hrakovsky et al.

FOREIGN PATENT DOCUMENTS

| WO | 2006064217 A2 | 6/2006 |
| WO | 2012120048 A1 | 9/2012 |

OTHER PUBLICATIONS

"Safety and Tolerability of AZD0530 (Saracatinib) in Alzheimer's Disease" ClinicalTrials.gov Identifier: NCT01864655. May 8, 2013. Retrieved from internet on Feb. 7, 2016. Found at: https://clinicaltrials.gov/ct2/show/study/NCT01864655?term=azd0530.
Bekris, et al., "Tau Phosphorylation Pathway Genes and Cerebrospinal Fluid Tau Levels in Alzheimer's Disease", Am J Med Genet B Neuropsychiatr Genet. 159B(7), Oct. 2012, 874-883.
Bhaskar, et al., "Disease-related Modifications in Tau Affect the Interaction between Fyn and Tau", J Biol Chem. 280(42), Oct. 21, 2005, 35119-35125.
Bhaskar, et al., "Tyrosine phosphorylation of tau accompanies disease progression in transgenic mouse models of tauopathy", Neuropathol Appl Neurobiol.36(6), Oct. 2010, 462-477.
Bizat, et al., "Neuron Dysfunction Is Induced by Prion Protein with an Insertional Mutation via a Fyn Kinase and Reversed by Sirtuin Activation in Caenorhabditis elegans", J Neurosci. 30(15), Apr. 14, 2010, 5394-5403.
Chin, et al., "Fyn Kinase Induces Synaptic and Cognitive Impairments in a Transgenic Mouse Model of Alzheimer's Disease", J Neurosci. 25(42), Oct. 19, 2005, 9694-9703.
Chin, et al., "Fyn Kinase Modulates Synaptotoxicity, But Not Aberrant Sprouting, in Human Amyloid Precursor Protein Transgenic Mice", J Neurosci. 24(19), May 12, 2004, 4692-4697.
Cruchaga, et al., "SNPs Associated with Cerebrospinal Fluid Phospho-Tau Levels Influence Rate of Decline in Alzheimer's Disease", PLoS Genet. 6(9):e1001101, Sep. 16, 2010, 1-10.
Grant, et al., "Impaired Long-Term Potentiation, Spatial Learning, and Hippocampal Development in fyn Mutant Mice", Science 258(5090), Dec. 18, 1992, 1903-1910.
Heidinger, et al., "Metabotropic Glutamate Receptor 1-Induced Upregulation of NMDA Receptor Current: Mediation through the Pyk2/Src-Family Kinase Pathway in Cortical Neurons", J Neurosci. 22(13), Jul. 1, 2002, 5452-5461.
Ittner, et al., "Dendritic Function of Tau Mediates Amyloid-β Toxicity in Alzheimer's Disease Mouse Models", Cell 142(3), Aug. 6, 2010, 387-397.
Kojima, et al., "Higher Seizure Susceptibility and Enhanced Tyrosine Phosphorylation of N-Methyl-D-Aspartate Receptor Subunit 2B in fyn Transgenic Mice", Learn Mem. 5(6), Nov.-Dec. 1998, 429-445.
Larson, et al., "The complex PrP(c)-Fyn couples human oligomeric Aβ with pathological tau changes in Alzheimer's disease", J Neurosci 32(47), Nov. 21, 2012, 16857-71a.
Lee, et al., "Phosphorylation of Tau by Fyn: Implications for Alzheimer's Disease", J Neurosci. 24(9), Mar. 3, 2004, 2304-2312.
Lee, et al., "Tau interacts with src-family non-receptor tyrosine kinases", J Cell Sci. 111 ( Pt 21), Nov. 1998, 3167-3177.
Li, et al., "Levels of mTOR and its downstream targets 4E-BP1, eEF2, and eEF2 kinase in relationships with tau in Alzheimer's disease brain", FEBS J. 272(16), Aug. 2005, 4211-4220.
Liang, et al., "Neuroprotective Profile of Novel Src Kinase Inhibitors in Rodent Models of Cerebral Ischemia", J Pharmacol Exp Ther. 331(3), Dec. 2009, 827-835.
Málaga-Trillo, et al., "Regulation of Embryonic Cell Adhesion by the Prion Protein", PLoS Biol. 7(3):e55, Mar. 10, 2009, 0576-0590.
Nakazawa, et al., "Characterization of Fyn-mediated Tyrosine Phosphorylation Sites on GluRe2 (NR2B) Subunit of the N-Methyl-D-aspartate Receptor", J Biol Chem. 276(1), Jan. 5, 2001, 693-699.
Prybylowski, et al., "The synaptic localization of NR2B-containing NMDA receptors is controlled by interactions with PDZ proteins and AP-2", Neuron 47(6), Sep. 15, 2005, 845-857.

(Continued)

*Primary Examiner* — Yong S. Chong
(74) *Attorney, Agent, or Firm* — Saul Ewing Arnstein & Lehr LLP; Kathryn Doyle; Domingos J. Silva

(57) ABSTRACT

The present invention provides compositions and methods for treating and preventing an Aβ-modulated disease and/or a Tauopathy. In certain embodiments, the invention provides an inhibitor of Fyn tyrosine kinase, and methods of using the same. In certain embodiments, the inhibitor of the invention inhibits Aβ oligomer induced signaling and reduces or halts the progression of Alzheimer's Disease.

16 Claims, 23 Drawing Sheets

(56) References Cited

OTHER PUBLICATIONS

Rammes, et al., "Therapeutic significance of NR2B-containing NMDA receptors and mGluR5 metabotropic glutamate receptors in mediating the synaptotoxic effects of β-amyloid oligomers on long-term potentiation (LTP) in murine hippocampal slices", Neuropharmacology 60(6), May 2011, 982-990.

Renner, et al., "Deleterious Effects of Amyloid β Oligomers Acting as an Extracellular Scaffold for mGluR5", Neuron. 66(5), Jun. 10, 2010, 739-754.

Roberson, et al., "Amyloid-β/Fyn-Induced Synaptic, Network, and Cognitive Impairments Depend on Tau Levels in Multiple Mouse Models of Alzheimer's Disease", J Neurosci.31(2), Jan. 12, 2011, 700-711.

Suzuki, et al., "NMDA receptor subunits epsilon 1 (NR2A) and epsilon 2 (NR2B) are substrates for Fyn in the postsynaptic density fraction isolated from the rat brain", Biochem Biophys Res Commun. 216(2), Nov. 13, 1995, 582-588.

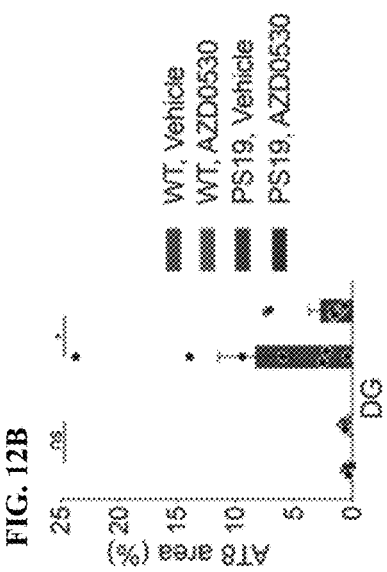
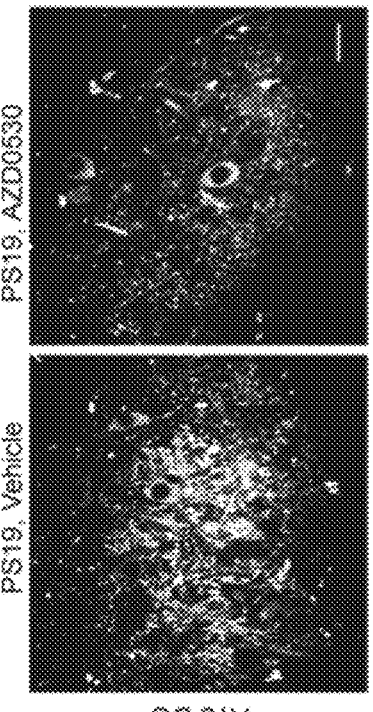
FIG. 12A
FIG. 12B
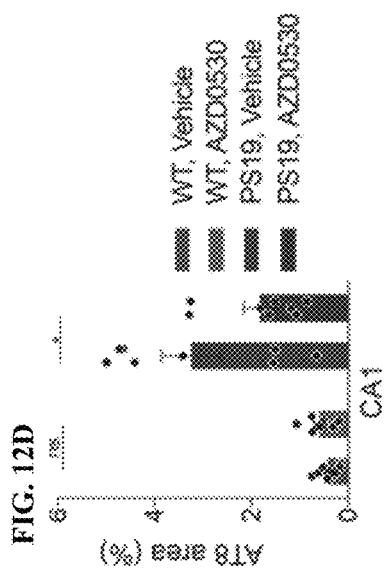
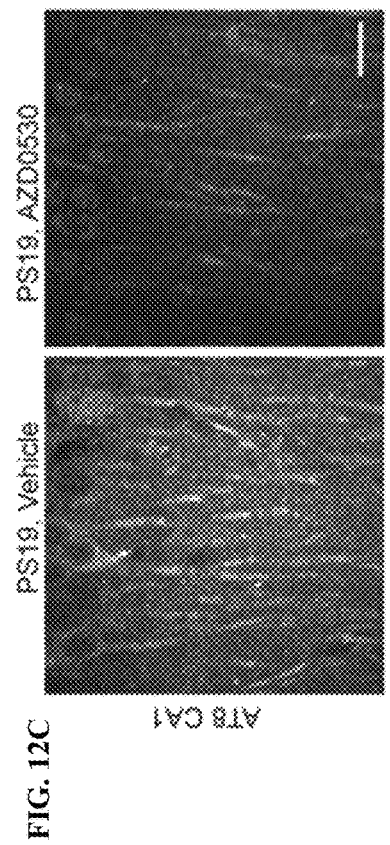
FIG. 12C
FIG. 12D
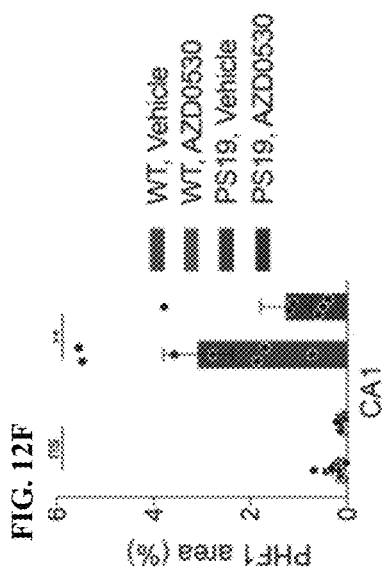
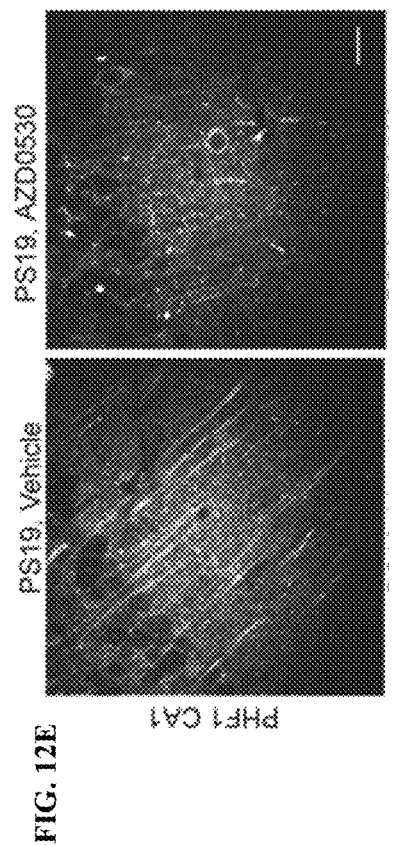
FIG. 12E
FIG. 12F FIG. 13B 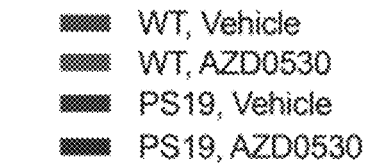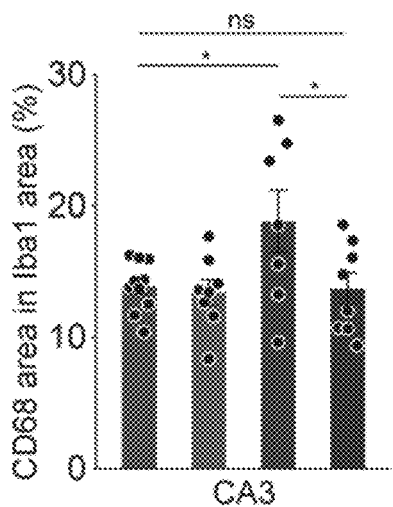

FIG. 13D 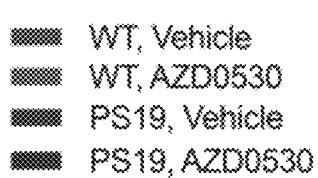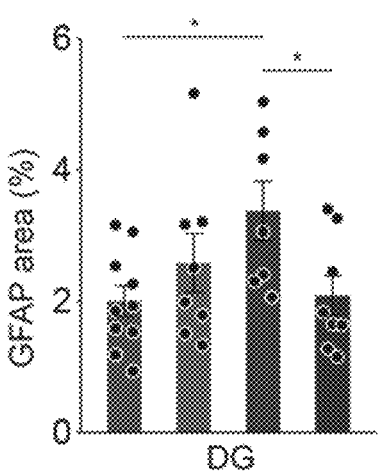

FIG. 14A SV2A, CA3
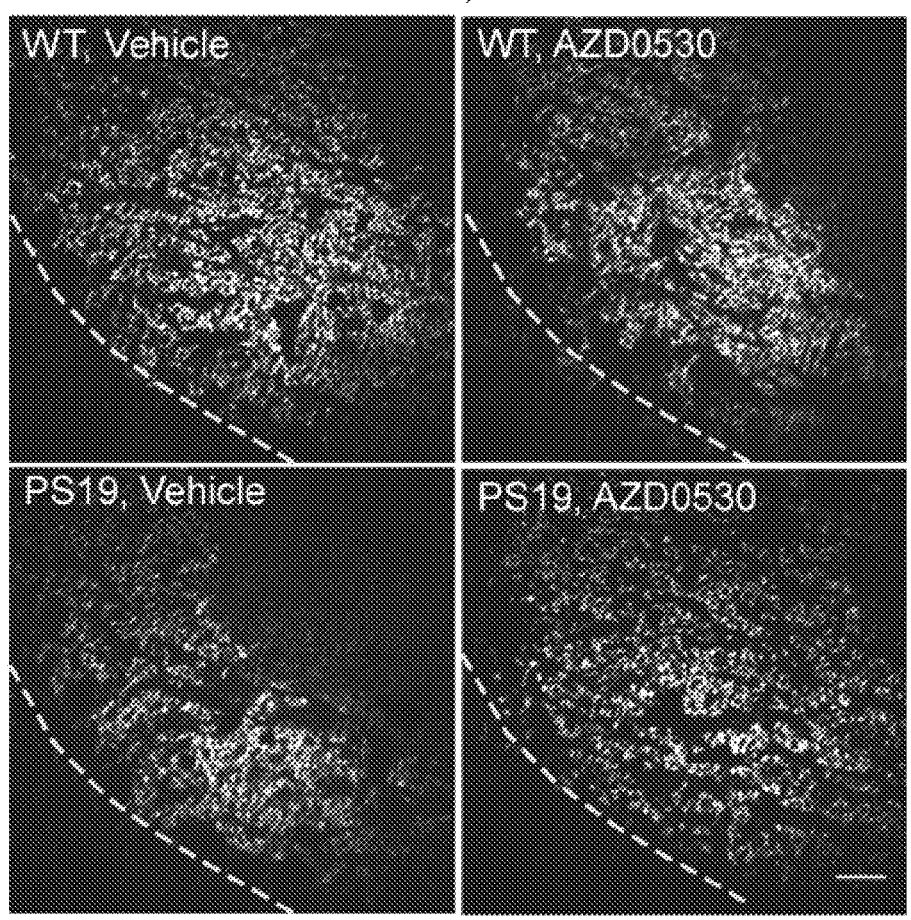
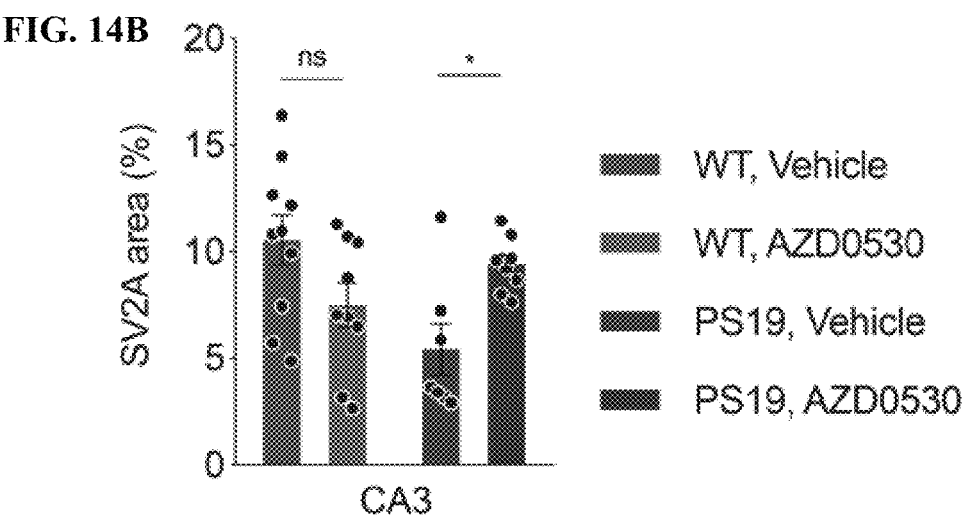
FIG. 14B

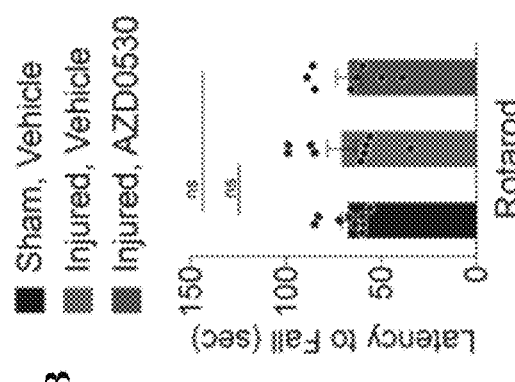
FIG. 15A
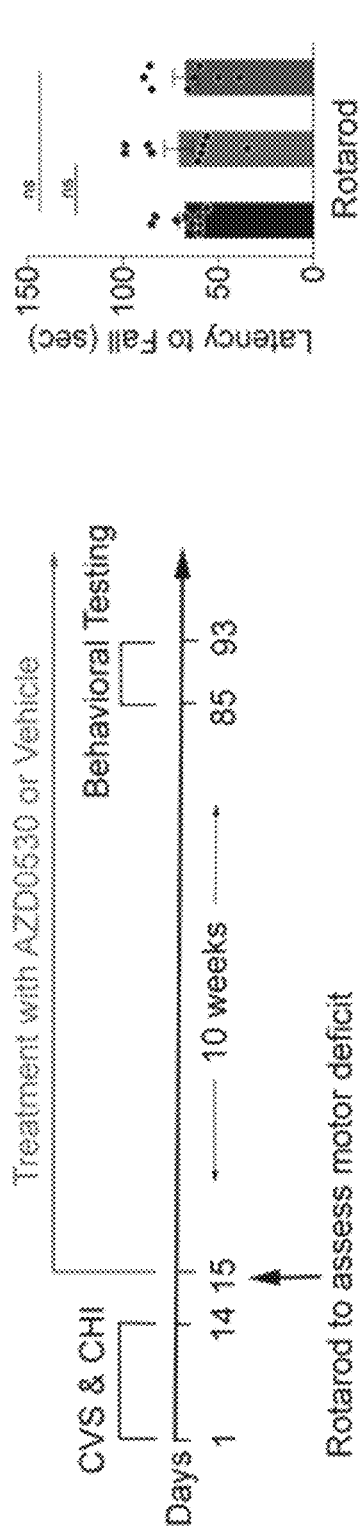
FIG. 15B
FIG. 15C
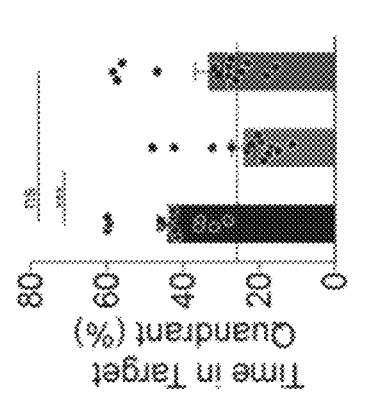
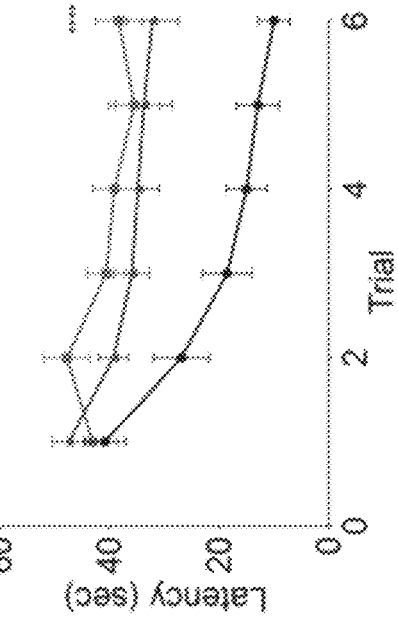
FIG. 15D
FIG. 15E
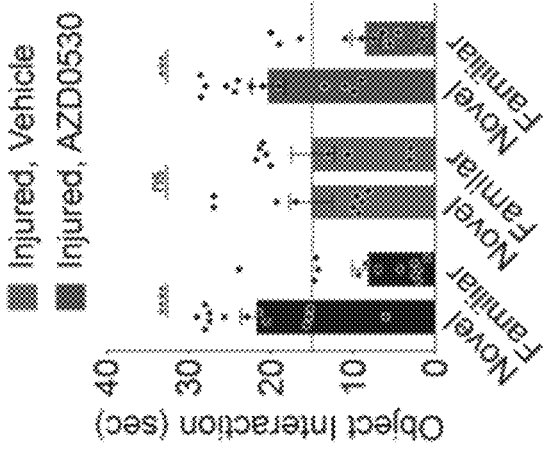

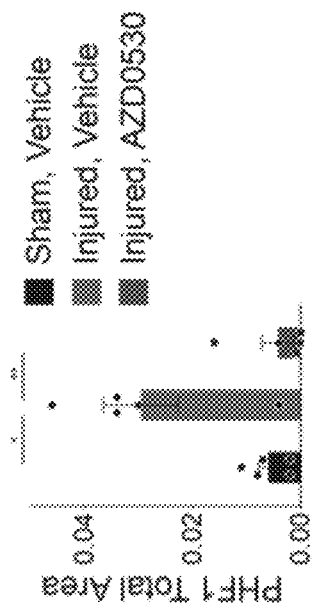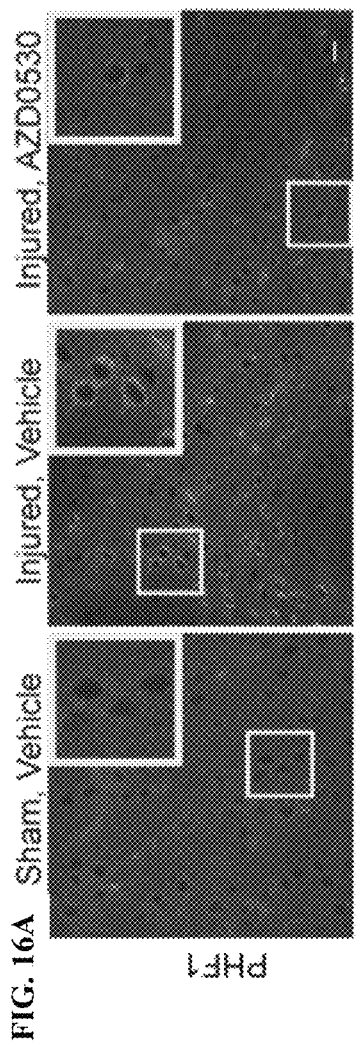
FIG. 16A  FIG. 16B
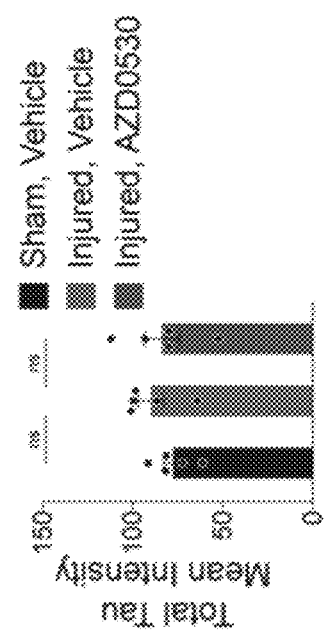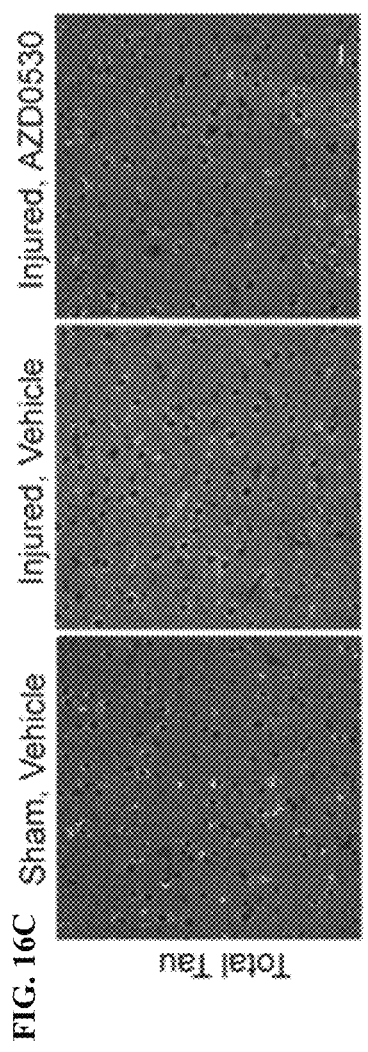
FIG. 16C  FIG. 16D
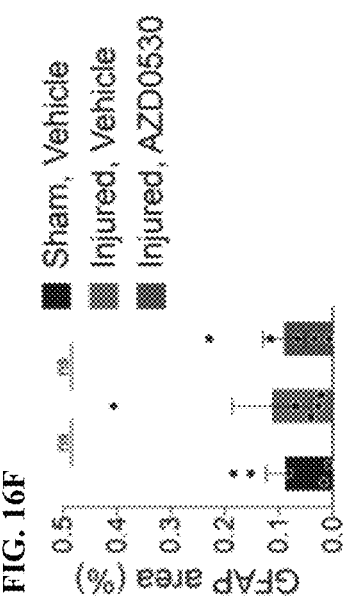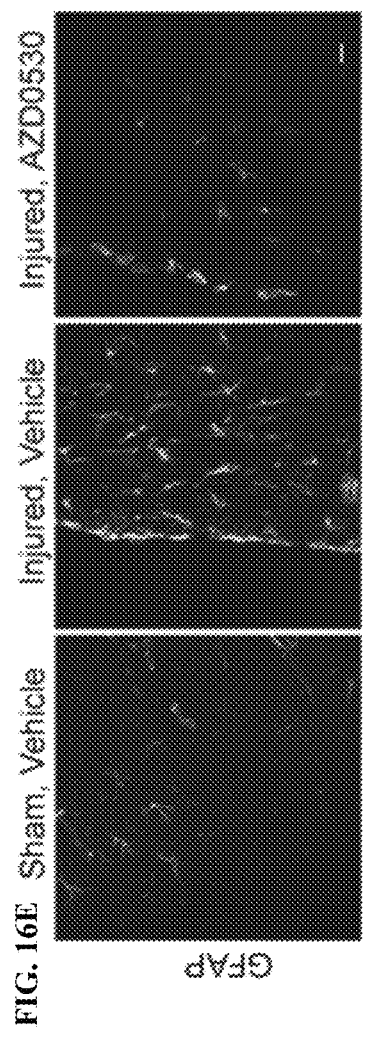
FIG. 16E  FIG. 16F

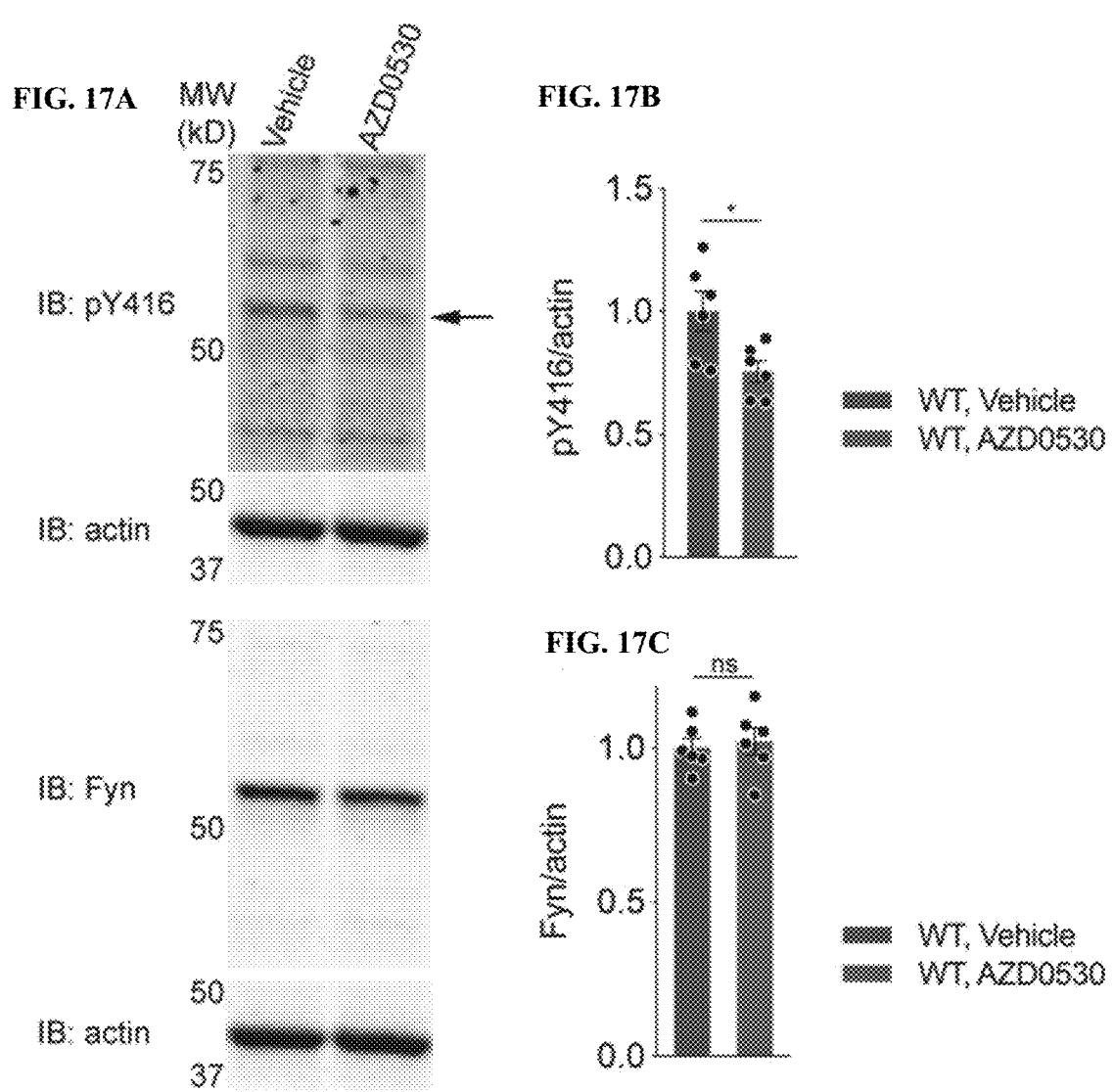

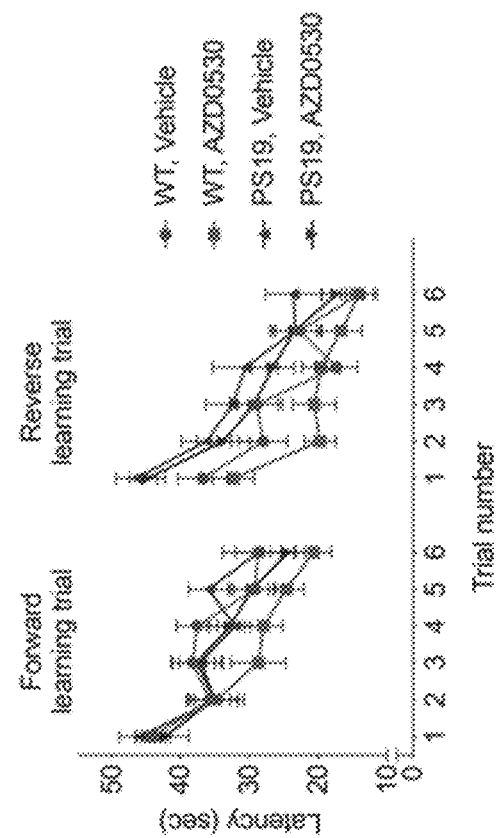
FIG. 18A
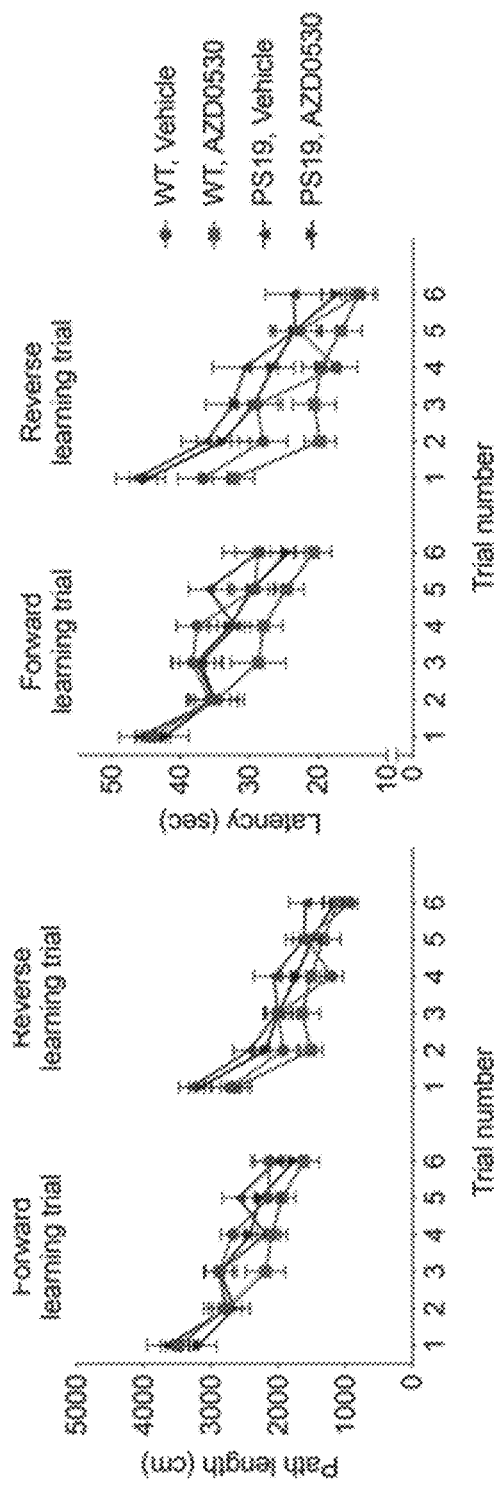
FIG. 18B
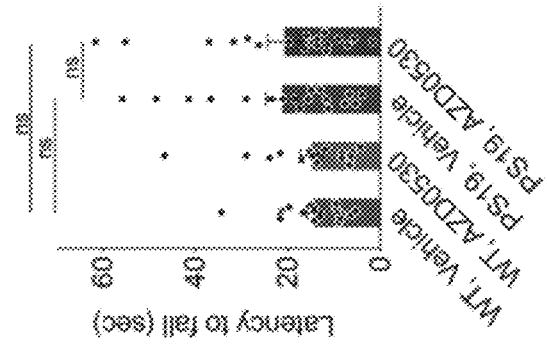
FIG. 18C  Visible platform
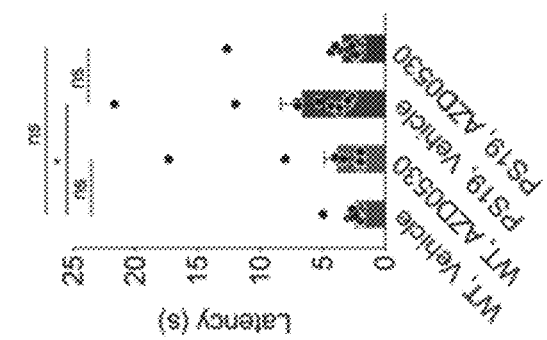
FIG. 18D  Rotarod

COMPOSITIONS AND METHODS FOR IMPROVING COGNITION IN A SUBJECT

CROSS-REFERENCE TO RELATED APPLICATIONS

The present application is a continuation-in-part and claims priority to U.S. application No. 14/272,874, filed May 8, 2014, now issued as U.S. Pat. No. 10,660,957, which claims priority under 35 U.S.C. § 119(e) to U.S. Provisional Application No. 61/834,595, filed Jun. 13, 2013, all of which applications are hereby incorporated by reference in their entireties herein.

STATEMENT REGARDING FEDERALLY SPONSORED RESEARCH OR DEVELOPMENT

This invention was made with government support under AG034924, AG053000, and TR000967 awarded by National Institutes of Health. The government has certain rights in the invention.

BACKGROUND OF THE INVENTION

Alzheimer's Disease (AD) is the most common dementing illness and afflicts over 5 million people in the USA currently, with an annual health care burden near $200 billion (Alzheimer's Association, 2012, Alzheimer's Dement 8:131-168). Unfortunately, no current therapy modifies the course of AD. The clinical dementia of AD is coupled with a distinct pathology, with senile plaques consisting of amyloid-β (Aβ) peptide, and with neurofibrillary tangles consisting of hyperphosphorylated microtubule-associated protein Tau (MAPT) protein.

The existence of rare autosomal dominant cases of AD caused by mutations of the amyloid-β precursor protein (APP) or the presenilin (PS1 and PS2) processing enzymes that produce Aβ provides genetic proof that APP/Aβ pathways can trigger clinical AD (Hardy et al., 2002, Science 297:353-356; Tanzi et al, 2005, Cell 120:545-555; Holtzman et al., 2011, Science Transl Med 3:77sr71; Lu et al., 1997, J Neurosci 17:5196-5205). Other APP mutations reduce AD risk (Jonsson et al., 2012, Nature 488:96-99).

Tau mutations cause dementia in frontotemporal lobar degeneration (Mackenzie et al., 2010, Acta Neuropathol 119:1-4). The hyperphosphorylated Tau protein accumulates at multiple sites and misfolds to create paired helical filaments in neurofibrillary tangles. This accumulation is accompanied by synapse loss, gliosis, neurodegeneration, and deficits of neurological function, including learning and memory and locomotion. Furthermore, reduction of Tau expression is protective in several neurodegenerative models. In recent years, Tau pathology has been recognized as a key feature of chronic late developing dementia after repetitive mild head trauma, in the syndrome of CTE.

Biomarker studies of late onset non-familial AD span the progression of disease from presymptomatic stage, to mild cognitive impairment, to AD (Holtzman et al., 2011, Science Transl Med 3:77sr71; Shaw et al., 2009, Ann Neurol 65:403-413; Jack et al., 2010, Lancet Neurol 9:119-128). Such observations have revealed that Aβ dysregulation, as detected by CSF levels or by positron emission tomography, is the earliest detectable change of the AD process, consistent with Aβ serving as the trigger for the disease.

Large extracellular and inert plaques of amyloid mark the pathology, but attention has focused on conformationally distinct soluble oligomers of Aβ (Aβo) as being neurotoxic (Lesne et al., 2006, Nature 440:352-357; Shankar et al., 2008, Nat Med 14:837-842; Walsh et al., 2002, Nature 416:535-539; Lambert et al., 1998, Proc Natl Acad Sci USA 95:6448-6453). Specifically, neurotoxicity is characterized by synaptic malfunction, and is accompanied by loss of dendritic spines. Chronically, synaptic changes are followed by neurofibrillary tangles, neuro-inflammation, and neuronal cell loss.

In the only reported genome-wide unbiased screen for Aβo binding sites, cellular prion protein ($PrP^C$) was identified (Lauren et al., 2009, Nature 457:1128-1132). Aβ binds with high affinity to $PrP^C$ and is oligomer specific, with little or no affinity for fibrillary or monomeric states (Lauren et al., 2009, Nature 457:1128-1132; Chen et al., 2010, J Biol Chem 285:26377-26383; Calella et al., 2010, EMBO Mol Med 2:306-314; Balducci et al., 2010, Proc Natl Acad Sci USA 107:2295-2300). In vivo, $PrP^C$ is not essential for certain Aβ-related phenotypes (Calella et al., 2010, EMBO Mol Med 2:306-314; Balducci et al., 2010, Proc Natl Acad Sci USA 107:2295-2300; Kessels et al., 2010, Nature 466: E3-4: discussion E4-5; Cisse et al., 2011, J Neurosci 31:10427-10431), but is required for cell death in vitro, for reduced survival of APP/PS1 transgenic lines, for epileptiform discharges, for synapse loss, for serotonin axon degeneration and for spatial learning and memory deficits (Um et al., 2012, Nat Neurosci 15:1227-1235; Resenberger et al., 2011, EMBO J 30:2057-2070; Bate et al., 2011, J Biol Chem 286:37955-37963; Alier et al., 2011, J Neurosci 31:16292-16297; Chung et al, 2010, BMC Neurosci 11:130; Gimbel et al., 2010, J Neurosci 30:6367-6374; Kudo et al., 2012; Hum Mol Genet 21:1138-1144; You et al., 2012, Proc Natl Acad Sci USA 109:1737-1742). Critically, the ability of human AD brain-derived Aβ species to suppress hippocampal synaptic plasticity requires $PrP^C$, and human AD contains $PrP^C$-interacting Aβo species and Aβ-$PrP^C$ complexes (Um et al., 2012, Nat Neurosci 15:1227-1235; Zou et al., 2011, J Biol Chem 286:15095-15105; Freir et al., 2011, Nat Commun 2:336; Barry et al., 2011, J Neurosci 31:7259-7263).

Despite the enormous and growing burden of AD, there remains no effective disease-modifying therapy today. The approaches now in clinical trials are mostly centered on efforts to alter Aβ itself (e.g., its production or clearance or aggregation). No major trial has centered on the signal transduction downstream of toxic Aβ species. In fact, there has been no successful clinical trial targeting Tau and/or Tau kinases in AD to this date.

There are nine members of Src family of intracellular non-receptor tyrosine kinases. Five of them (Src, Fyn, Lck, Lyn, and Yes) are expressed in the central nervous system, but Src and Fyn are most highly expressed in the brain. Fyn activity, like that of other Src family kinases, is regulated by intramolecular interactions that depend on an equilibrium between tyrosine phosphorylation and dephosphorylation (Thomas et al., 1997, Ann. Rev. Cell & Dev. Biol. 13:513-609). In the basal state, catalytic activity is constrained by intramolecular interactions, such as engagement of the SH2 domain by a phosphorylated C-terminal Tyr 527. Disruption of these interactions by phosphorylation at Tyr 416 in the activation loop of the kinase domain and/or by dephosphorylation of Tyr 527 results in Fyn activation (Hunter, 1987, Cell, 49: 1-4).

Fyn has been localized to the post-synaptic density (PSD) fraction of the brain and amongst its substrates are receptors for the major excitatory transmitter glutamate. Fyn regulates glutamate receptor trafficking and synaptic plasticity (Nakazawa et al., 2001, J Biol Chem 276:693-699; Kojima et al., 1998, Learning & Memory (Cold Spring Harbor N.Y.)

5:429-445; Grant et al., 1992, Science 258:1903-1910; Prybylowski et al., 2005, Neuron 47:845-857). Specifically, Fyn phosphorylates the NMDA-type glutamate receptor subunits, NR2A and NR2B (Suzuki et al., 1995, Biochem Biophys Res Commun 216:582-588).

There remains an unmet need in the art for novel methods of treating an Aβ-modulated disease or disorder, such as AD, and/or improving cognition in a subject. There also remains an unmet need in the art for novel methods of treating certain Tauopathies. The present invention satisfies these unmet needs.

BRIEF SUMMARY OF THE INVENTION

The present invention provides a pharmaceutical composition comprising an effective amount of saracatinib, or a pharmaceutically acceptable salt, prodrug or solvate thereof.

The present invention further provides a method of treating or preventing an Aβ-modulated disease or disorder in a mammal in need thereof, the method comprising administering to the mammal a therapeutically effective amount of a Fyn inhibitor.

The present invention further provides a method of improving, or preventing further loss of, cognition in a mammal in need thereof, the method comprising administering to the mammal a therapeutically effective amount of a Fyn inhibitor.

The present invention further provides a method of treating, ameliorating, or inhibiting further development of a Tauopathy in a mammal in need thereof. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof. In certain embodiments, accumulation of hyperphosphorylated Tau protein is reversed, inhibited, or minimized in the mammal.

The present invention further provides a method of improving memory, ameliorating loss of memory, or preventing further loss of memory in a mammal afflicted with a Tauopathy. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof.

The present invention further provides a method of treating, ameliorating, or preventing further development of at least one of hyperphosphorylated Tau accumulation, synapse loss, and memory deficit in a mammal afflicted with traumatic brain injury. In certain embodiments, the method comprises administering to the mammal a therapeutically effective amount of a Fyn inhibitor after the mammal suffers the traumatic brain injury. In certain embodiments, the administering minimizes, reduces, or reverses at least one of gliosis, neurodegeneration, and neurological function deficits (such as in, but not limited to, learning, reasoning, memory, and/or locomotion) in the afflicted mammal. In certain embodiments, the administering takes place 16 weeks or less after the traumatic brain injury.

The present invention further provides a kit for preventing or treating an Aβ-modulated disease, or improving cognition, in a mammal, wherein the kit comprises a pharmaceutical composition of the invention, an applicator, and an instructional material for use thereof. In certain embodiments, the instructional material recites the amount of, and frequency with which, the composition is to be administered to the mammal.

In certain embodiments, administration to a mammal of the effective amount of saracatinib, or a pharmaceutically acceptable salt, prodrug or solvate thereof, affords a trough CSF concentration of saracatinib in the mammal of at least about 0.9 nM. In other embodiments, the trough CSF concentration of saracatinib in the mammal is at least about 2.1 nM. In yet other embodiments, the trough CSF concentration of saracatinib in the mammal is at least about 2.5 nM.

In certain embodiments, the trough CSF concentration of saracatinib in the mammal ranges from about 0.9 to about 14.0 nM. In other embodiments, the trough CSF concentration of saracatinib in the mammal ranges from about 0.9 nM to about 2.2 nM. In yet other embodiments, the trough CSF concentration of saracatinib in the mammal ranges from about 2.1 nM to about 8.3 nM. In yet other embodiments, the trough CSF concentration of saracatinib in the mammal ranges from about 2.5 nM to about 14.0 nM.

In certain embodiments, the average brain concentration of saracatinib in the mammal is selected from the group consisting of: at least about 3 nM, at least about 7 nM, and at least about 8 nM. In other embodiments, the average brain concentration of saracatinib in the mammal ranges from about 3 to about 46 nM. In yet other embodiments, the average brain concentration range of saracatinib in the mammal is selected from the group consisting of: from about 3 to about 7 nM, from about 7 to about 27 nM, and from about 8 to about 46 nM.

In certain embodiments, the saracatinib is saracatinib free base. In other embodiments, the saracatinib is saracatinib difumarate. In yet other embodiments, the saracatinib is selected from the group consisting of saracatinib free base, saracatinib difumarate, and any combinations thereof.

In yet other embodiments, the pharmaceutical composition is coformulated with at least one additional agent that treats or prevents an Aβ-modulated disease in a mammal. In yet other embodiments, the pharmaceutical composition is coformulated with at least one additional agent that improves, or prevents further loss of, cognition in a mammal. In yet other embodiments, the pharmaceutical composition is coformulated with at least one additional agent that treats or prevents a Tauopathy in a mammal.

In certain embodiments, the mammal is human. In other embodiments, the free concentration of saracatinib in the plasma of the human ranges from about 2.6 to about 41.2 nM. In yet other embodiments, the free concentration of saracatinib in the plasma of the human is selected from the group consisting of: from about 2.6 to about 6.5 nM, from about 6.2 to about 24.4 nM, and from about 7.4 to about 41.2 nM.

In certain embodiments, the Aβ-modulated disease or disorder is selected from the group consisting of Alzheimer's Disease (AD), prodromal Alzheimer's Disease, amnestic mild cognitive impairment (MCI), Down syndrome dementia, traumatic brain injury, Lewy body dementia, Parkinson's Disease with dementia, fronto-temporal dementia (including fronto-temporal lobar dementia), after stroke aphasia, and any combinations thereof.

In certain embodiments, the disease or disorder is Alzheimer's Disease (AD). In certain embodiments, the disease or disorder is prodromal Alzheimer's Disease. In certain embodiments, the disease or disorder is amnestic mild cognitive impairment (MCI). In certain embodiments, the disease or disorder is Down syndrome dementia. In certain embodiments, the disease or disorder is traumatic brain injury. In certain embodiments, the disease or disorder is Lewy body dementia. In certain embodiments, the disease or disorder is Parkinson's Disease with dementia. In certain embodiments, the disease or disorder is fronto-temporal dementia. In certain embodiments, the disease or disorder is fronto-temporal lobar dementia. In certain embodiments, the disease or disorder is after stroke aphasia.

In certain embodiments, Aβ oligomer-induced signaling is inhibited in the mammal.

In certain embodiments, the Fyn inhibitor is selected from the group consisting of a nucleic acid, siRNA, antisense nucleic acid, ribozyme, peptide, antibody, small molecule, antagonist, aptamer, peptidomimetic, and any combinations thereof. In other embodiments, the Fyn small molecule inhibitor is selected from the group consisting of saracatinib, bosutinib, dasatinib, ponatinib, PP2, a salt, prodrug or solvate thereof, a derivative thereof, and any combinations thereof.

In certain embodiments, the Fyn small molecule inhibitor is saracatinib, or a pharmaceutically acceptable salt, prodrug or solvate thereof. In other embodiments, the Fyn inhibitor is saracatinib, or a pharmaceutically acceptable salt, prodrug or solvate thereof. In yet other embodiments, the Fyn inhibitor is saracatinib free base. In yet other embodiments, the Fyn inhibitor is saracatinib difumarate.

In certain embodiments, the administration of the composition to the mammal affords a trough CSF concentration of saracatinib in the mammal of at least about 0.9 nM. In other embodiments, the trough CSF concentration of saracatinib in the mammal is at least about 2.1 nM. In yet other embodiments, the trough CSF concentration of saracatinib in the mammal is at least about 2.5 nM. In yet other embodiments, the trough CSF concentration of saracatinib ranges from about 0.9 to about 14.0 nM. In yet other embodiments, the trough CSF concentration of saracatinib is in the range selected from the group consisting of from about 0.9 nM to about 2.2 nM, from about 2.1 nM to about 8.3 nM, and from about 2.5 nM to about 14.0 nM.

In certain embodiments, the average brain concentration of saracatinib in the mammal is selected from the group consisting of at least 3 nM, at least 7 nM, and at least 8 nM. In other embodiments, the average brain concentration of saracatinib in the mammal ranges from about 3 to about 46 nM. In yet other embodiments, the average brain concentration range of saracatinib in the mammal is selected from the group consisting of: from about 3 to about 7 nM, from about 7 to about 27 nM, and from about 8 to about 46 nM In certain embodiments, the composition is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

In certain embodiments, the method further comprises administering to the mammal at least one additional agent that treats or prevents the Aβ-modulated disease or disorder in the mammal. In other embodiments, the method further comprises administering to the mammal at least one additional agent that improves or prevents further loss of cognition in the mammal. In yet other embodiments, the method further comprises administering to the mammal at least one additional agent that treats, ameliorates, or inhibits further development of the Tauopathy in the mammal. In yet other embodiments, the composition and at least one additional agent are coformulated. In yet other embodiments, the mammal is human.

In certain embodiments, the human is administered a daily dose of saracatinib, or a pharmaceutically acceptable salt thereof, that comprises an amount of at least 50 mg of saracatinib free base. In other embodiments, the human is administered a daily dose of saracatinib, or a pharmaceutically acceptable salt thereof, that comprises an amount of at least 100 mg of saracatinib free base. In yet other embodiments, the human is administered a daily dose of saracatinib, or a pharmaceutically acceptable salt thereof, that comprises an amount of at least 125 mg of saracatinib free base.

In certain embodiments, the human is administered a daily dose of saracatinib, or a pharmaceutically acceptable salt thereof, that comprises an amount of about 50 mg of saracatinib free base. In other embodiments, the human is administered a daily dose of saracatinib, or a pharmaceutically acceptable salt thereof, that comprises an amount of about 100 mg of saracatinib free base. In yet other embodiments, the human is administered a daily dose of saracatinib, or a pharmaceutically acceptable salt thereof, that comprises an amount of about 125 mg of saracatinib free base.

In certain embodiments, the human is administered a daily dose of saracatinib, or a pharmaceutically acceptable salt thereof, that comprises an amount ranging from about 45 to about 55 mg of saracatinib free base. In other embodiments, the human is administered a daily dose of saracatinib, or a pharmaceutically acceptable salt thereof, that comprises an amount ranging from about 90 to about 110 mg of saracatinib free base. In yet other embodiments, the human is administered a daily dose of saracatinib, or a pharmaceutically acceptable salt thereof, that comprises an amount ranging from about 112.5 to about 137.5 mg of saracatinib free base.

In certain embodiments, the human is administered a daily dose of about 50 mg of saracatinib free base. In yet other embodiments, the human is administered a daily dose of about 100 mg of saracatinib free base. In yet other embodiments, the human is administered a daily dose of about 125 mg of saracatinib free base.

In certain embodiments, the human is administered a daily dose of saracatinib free base ranging from about 45 to about 55 mg. In yet other embodiments, the human is administered a daily dose of saracatinib free base ranging from about 90 to about 110 mg. In yet other embodiments, the human is administered a daily dose of saracatinib free base ranging from about 112.5 to about 137.5 mg.

In certain embodiments, the human is administered a daily dose of about 71.4 mg of saracatinib difumarate. In yet other embodiments, the human is administered a daily dose of about 142.9 mg of saracatinib difumarate. In yet other embodiments, the human is administered a daily dose of about 178.6 mg of saracatinib difumarate.

In certain embodiments, the human is administered a daily dose of saracatinib difumarate ranging from about 64.3 to about 78.6 mg. In yet other embodiments, the human is administered a daily dose of saracatinib difumarate ranging from about 128.6 to about 157.2 mg. In yet other embodiments, the human is administered a daily dose of saracatinib difumarate ranging from about 160.7 to about 196.5 mg.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 1A: Aβo increases NR2B phosphorylation via $PrP^C$ and Fyn. Cortical neurons from WT mouse embryos after 21 DIV were treated with Aβo for 20 min. Cell lysates were analyzed by immunoblot as indicated. FIG. 1B: WT, $Prnp^{-/-}$ or $Fyn^{-/-}$ cortical neurons were pre-incubated with or without 10 µg/ml of 6D11 antibody, and then treated with Aβo for 20 min to 4 h. Biotinylated cell surface proteins and total lysate proteins were assessed by immunoblot. FIG. 1C: WT cortical neurons were treated with Aβo for 15 or 60 min. The intracellular calcium response to NMDA (50 µM) or calcium ionophore ionomycin (500 nM) was monitored with FLIPR Calcium 4. FIG. 1D: WT, $Prnp^{-/-}$ or $Fyn^{-/-}$ cortical neurons were treated with Aβo for 1.5 h, prior to measurement of LDH release. The indicated cultures were pre-incubated with 6D11 antibody, or were treated with Aβ monomer (Aβm) in place of Aβo. FIG. 1E: Hippocampal neurons were transfected with a Myr-EGFP expression vector and then imaged. Aβo was added and observations were continued for 5 hours. Lost dendritic spines after Aβo addition in the WT neurons are indicated with arrowheads. Scale bar, 1 µm. FIG. 1F: Mechanistic AD model illustrates the dendritic spine and the PSD. Aβ oligomers bind to $PrP^C$ and cause Fyn activation and NMDA-R redistribution. Dendritic Tau delivers Fyn to the PSD and is hyper-phosphorylated by Aβo signaling. Date are mean±s.e.m.*, P<0.05; **, P<0.01; one-way ANOVA.

FIG. 2A: DIV21 cortical neurons from wild type or Prnp-/- mice were treated with or without Aβo for 5 min. Whole cell lysates were analyzed by anti-phospho-eEF2, anti-eEF2, or anti-$PrP^C$ immunoblot. Aβo increased p-eEF2/eEF2 ratio to 210±20% of baseline in WT cultures (mean±sem, n=3), but there was no significant increase in Prnp-/- cultures. FIG. 2B: DIV21 cortical neurons from wild type mice were treated with the indicated human control or AD brain extracts (30 µg total protein/ml) for 5 min. Whole cell lysates were analyzed by anti-phospho-eEF2 or anti-eEF2 immunoblot. AD, but not control (Con), brain extracts increased p-eEF2/eEF2 ratio to 200±10% of untreated cultures (mean±sem, n=4). FIG. 2C: Wild type cortical neurons were treated with or without Aβo for 15 min. The indicated samples were treated with saracatinib for 1 hour prior to Aβo exposure. Whole cell lysates were analyzed by anti-phospho-SFK, anti-Fyn, anti-phospho-eEF2, or anti-eEF2 immunoblot. GAPDH served as a loading control. FIG. 2D: Quantification of phospho-eEF2 level normalized to eEF2 immunoreactivity from four independent experiments. Mean±sem; *, P<0.05, n.s., not significant; One-way ANOVA, with Tukey post-hoc pairwise comparisons.

FIG. 10A: Representative sections from the labeled groups were stained with anti-PSD-95 antibody and the molecular layer of the dentate gyrus was imaged with a confocal microscope with a 60× objective lens. Scale bar, 3 µm. FIG. 10B: Fractional area of immunoreactive puncta for PSD-95. p<0.05, ANOVA with post-hoc pairwise Tukey comparisons. Mean±SEM, n=5-10 mice per group, two images per mouse. FIG. 10C: Fractional area of immunoreactive puncta for SV2. p<0.05, ANOVA with post-hoc pairwise Fisher's least significant difference (LSD). Mean±SEM, n=5-10 mice per group, two images per mouse.

FIG. 11A: Timeline of PS19 mouse treatment. FIG. 11B: Morris water maze probe trial for 8-month-old PS19 or WT mice after 6 months of AZD0530 or Vehicle treatment. Twenty four hours after the reverse learning trials in the Morris water maze, the submerged platform was removed and the fraction of 60 sec spent in the target quadrant where the hidden platform had been located previously was recorded. n=11-15/group, each dot is one mouse. Data are mean±SEM. Dashed line indicates random chance performance. Two-way ANOVA reveal an interaction between genotype and treatment (p=0.014). *p<0.05; Sidak's post-hoc multiple comparisons test. FIG. 11C: Passive avoidance test for 8-month-old PS19 and WT mice after 6 months of treatment with AZD0530 or Vehicle. Latency was measured as the time for the mouse to cross to the opaque box. n=16-18/group. Wilcoxon match-pairs signed test; (WT, Vehicle: p=0.0007; WT, AZD0530: p<0.0001; PS19, AZD0530: p=0.1167; PS19, AZD0530: p=0.0126.)

FIG. 12A-12F illustrate reduced phospho-Tau accumulation in transgenic mice treated with AZD0530. FIG. 12A: Representative images of AT8 immunoreactivity in the dentate gyrus (DG) of the hippocampus in 9-month-old PS19 mice after 7 months of treatment with AZD0530 or Vehicle. Scale bar, 20 m. FIG. 12B: Quantification of AT8-positive area (%) in the dentate gyrus of the hippocampus in 9-month-old PS19 and WT mice after 7 months of treatment. Data are mean±SEM. n=7-10/group, each dot is one mouse. Two-way ANOVA revealed an interaction between genotype and treatment (p=0.0487). *p<0.05; Sidak's post hoc multiple comparison's test. FIG. 12C: Representative images of immunofluorescent staining for AT8 in the CA1 of the hippocampus in 9-month-old PS19 and WT mice after 7 months of treatment. Scale bar, 20 m. FIG. 12D: Quantification of AT8-positive area in the CA1 of the hippocampus in 9-month-old PS19 and WT mice after 7 months of treatment. Data are mean±SEM. n=7-10/group, each dot is one mouse. Two-way ANOVA revealed an interaction between genotype and treatment (p=0.03). *p<0.05; Sidak's post hoc multiple comparison's test. FIG. 12E: Representative images of immunofluorescent staining for PHF1 in the CA1 of the hippocampus in 9-month-old PS19 and WT mice after 7 months of treatment. Scale bar, 20 m. FIG. 12F: Quantification of PHF1-positive area in the CA1 of the hippocampus in 9-month-old PS19 and WT mice after 7 months of treatment. Data are mean±SEM. n=7-10/group, each dot is one mouse. Two-way ANOVA revealed an interaction between genotype and treatment (p=0.0341). **p<0.01; Sidak's post hoc multiple comparison's test.

FIGS. 13A-13D illustrate that chronic Fyn inhibition prevents glial activation in mutant Tau transgenic mice. FIG. 13A: Representative images of CD68 and Ibal double immunostaining in the CA3 region of the hippocampus from 9-month-old PS19 and WT mice after 7 months of treatment with AZD0530 or Vehicle. Scale bar, 20 μm. FIG. 13B: Quantification of CD68-positive area (%) within Ibal-immuoreative area in the CA3 segment of the hippocampus from 9-month-old PS19 and WT mice after 7 months of treatment. Data are as mean±SEM. n=7-10/group, each dot is one mouse. *p<0.05; One-way ANOVA with Dunnett's multiple comparisons test. FIG. 13C: Representative images of immunofluorescent staining GFAP in the dentate gyrus (DG) of the hippocampus in 9-month-old PS19 and WT mice after 7 months of treatment. Scale bar, 20 μm. FIG. 13D: Quantification of GFAP-positive area (%) in the dentate gyrus of the hippocampus in 9-month-old PS19 and WT mice after 7 months of treatment. n=7-10/group, each dot is one mouse. Data are mean±SEM. *p<0.05; One-way ANOVA with Dunnett's multiple comparisons test.

FIGS. 14A-14B illustrate the finding that loss of presynaptic marker SV2A in P301S Tau transgenic mice is rescued by Fyn inhibition. FIG. 14A: Representative images of immunofluorescent staining for SV2A in the CA3 region of the hippocampus from 9-month-old PS19 and WT mice after 7 months of treatment with AZD0530 or Vehicle. Dashed lines represent the divide between the cell body layer and synaptic region. The cell bodies in the image were used to capture similar ROI from each section. Scale bar, 20 μm. FIG. 14B: Quantification of SV2A-positive area (%) in the CA3 of the hippocampus in 9-month-old PS19 and WT mice after 7 months of treatment. Data are mean±SEM. n=7-10/group, each dot is one mouse. Two-way ANOVA revealed an interaction between genotype and treatment (p=0.0015). *p<0.05; Sidak's post hoc multiple comparison's test.

FIGS. 15A-15H illustrate the finding that Fyn inhibition rescues memory deficits after repeated mild head injury combined with chronic stress. FIG. 15A: Timeline for mice undergoing 14 days of chronic variable stress (CVS) and closed head injury (CHI) or Sham CVS & CHI paradigm. On Day 15, Rotarod testing was done to assess motor impairment in a subset of mice. The mice were treated with either AZD0530 (5 mg/kg/d) or Vehicle treatment for 10 weeks starting 24 hours after the final day of injury. This was followed by one week of behavioral testing, including novel object recognition test and Morris water maze prior to perfusion and immunohistochemistry. FIG. 15B: Rotarod prior to the treatment using the Sham and Injured groups. One-way ANOVA, p>0.05. Data are mean±SEM. n=8-9/group, each dot is one mouse. FIG. 15C: Novel object recognition test using the Sham mice and Injured mice with and without AZD0530 treatment. Two-way ANOVA, F(2, 64)=5.258 p=0.007 for interaction of group with object, Sidak's multiple comparison test: Novel vs Familiar for Sham Vehicle (SV): p<0.0001, for Injured Vehicle (IV): p=0.99, for Injured AZD (IA): p=0.0002. Data are mean±SEM. n=9-13/group, each dot represents one mouse. FIG. 15D: Latency to reach a hidden platform in Morris water maze across 6 blocks of 4 swims for Sham mice and Injured mice with and without AZD0530 treatment. Data are mean±SEM. n=14-17/group. Two-way ANOVA for time and group with main effect of group, p<0.0001, F (2, 41)=47.24. Tukey's multiple comparison test: SV vs IV: p<0.0001, IV vs IA: p=0.98, SV vs IA: p<0.0001. FIG. 15E: Morris water maze probe trial for Sham or Injured mice treated with Vehicle or AZD0530, showing time in the Target quadrant. One way ANOVA: F(2,39)=9.410, p=0.0005, Tukey's multiple comparison test: SV vs IV: p=0.0003, IV vs IA: p=0.12, SV vs IA: p=0.05. Data are mean±SEM. n=13-15/group, each dot is one mouse. Dashed line indicates random chance performance. FIG. 15F: A second group of mice underwent a similar 14 days of chronic variable stress (CVS) plus closed head injury (CHI) or Sham CVS & CHI paradigm, and then starting on Day 121 were treated with either AZD0530 (5 mg/kg/d) or Vehicle for 10 weeks. The mice subsequently underwent Morris water maze testing. FIG. 15G: Both Injured groups from F exhibited longer latency to the hidden platform during learning trials of the reverse MWM compared to the Sham group (two-way ANOVA, p<0.0001), but the two Injured groups were not significantly different from one another. Data are mean±SEM. n=8-26/group. FIG. 15H: During a probe performed 24 hours after the learning trials of H, neither the Inj (Veh) nor the Inj (AZD) demonstrated preference towards the target quadrant. Data are mean±SEM. n=8-26/group, each dot is one mouse.

FIGS. 16A-16F illustrate the finding that AZD0530 treatment prevents phospho-Tau accumulation after head injury plus stress. FIG. 16A: PHF-1 immunohistochemistry of coronal cerebral cortex sections, within 0.5-1 mm medial to the site of injury showed increased peri-nuclear PHF-1 signal in the Injured Vehicle treated group (IV) brain section, but reduced in the Injured AZD treated group (IA). Boxed area is shown at higher magnification inset. Scale bar, m. FIG. 16B: PHF-1 IHC quantification using ImageJ software measuring total stained area, yielded significant differences amongst the three groups. Data are mean±SEM. n=5/group, each dot is one mouse. One way ANOVA: $F(2,12)=9.967$, $p=0.0028$, Tukey's multiple comparison test: SV vs IV: $p=0.0077$, IV vs IA: $p=0.0046$. FIG. 16C: Total Tau IHC staining of the cortical sections in the same region did not demonstrate differences amongst the three groups. Scale bar, 20 μm. FIG. 16D: Total Tau IHC quantification analysis based on mean intensity did not show significant differences between the three groups. Data are mean±SEM. n=5/group, each dot is one mouse. FIG. 16E: GFAP IHC staining of cortical sections in the same region did not demonstrate group differences with more intragroup variability present. Scale bar, 20 μm. FIG. 16F: GFAP IHC quantification analysis based on % area did not result in groups differences, with greater degree of variability within groups. Data are mean±SEM. n=5/group, each dot is one mouse.

FIGS. 17A-17C illustrate reduced Fyn activation in mice fed AZD0530-containing food. FIG. 17A: Representative blots using anti-pY416, Fyn, and 8-actin antibodies of the RIPA-soluble fraction of the hippocampus of WT mice treated with Vehicle or AZD0530 for 9 months. FIG. 17B: Quantification of pY416-immunoreactive bands from the immunoblot from FIG. 17A by densitometric analysis. The bands indicated by an arrow in FIG. 17A were quantified. The band intensity was normalized to that of 8-actin and then normalized to the mean of the Vehicle-treated WT group. Data are represented as mean±SEM. n=6/group. *$p<0.05$; t-test. FIG. 17C: Quantification of Fyn-immunoreactive bands from the immunoblot in FIG. 17A by densitometric analysis. The band intensity was normalized to that of β-actin and then normalized to the mean of the Vehicle-treated WT group. Data are represented as mean±SEM. n=6/group. t-test.

FIGS. 18A-18D illustrate behavioral tests of PS19 or WT mice treated with AZD0530 or vehicle. FIG. 18A: Morris water maze latency to target for forward and reverse swims in 8-month-old PS19 and WT mice after 6 months of treatment. The latency was measured as the time for the mouse to find a submerged platform in a forward and a reverse swim after a platform relocation. Data are mean±SEM. n=11-15/group. One-way ANOVA. FIG. 18B: Morris water maze distance traveled for forward and reverse swims in 8-month-old PS19 and WT mice after 6 months of treatment. Pathlength is measured as the total distance traveled (in cm) before the mouse reaches the submerged platform. Data are mean±SEM. n=11-15/group. One-way ANOVA. FIG. 18C: Morris water maze visible platform trial after reverse swim. Latency is measured as the average amount of time the mouse takes to reach the flagged platform in an average of 12 trials or until the latency has plateaued for 3 trials, whichever comes first. Data are mean±SEM. n=11-15/group, each dot from one mouse. *$p<0.05$, One-way ANOVA with Holm-Sidak's multiple comparisons test. FIG. 18D: Rotarod trials in 8-month-old PS19 and WT mice of the prophylactic cohort. Latency to fall is measured as the time it takes to fall from the rotating, accelerating rod. Each data represents the average of 5 trials for one mouse. Data are mean±SEM. n=18-19/group. One-way ANOVA.

FIG. 19A: Representative images of Ibal immunostaining in the hippocampus in 9-month-old PS19 and WT mice after 7 months of treatment. Scale bar, 100 m. FIG. 19B: Quantification of Ibal-positive area (%) in the hippocampus in 9-month-old PS19 and WT mice collected after 7 months of treatment. Data are mean±SEM. n=7-10/group. One-way ANOVA. FIG. 19C: Representative images of immunofluorescent staining GFAP in the hippocampus in 9-month-old PS19 and WT mice after 7 months of treatment. Scale bar, 100 μm. FIG. 19D: Quantification of GFAP-positive area (%) in the hippocampus in 9-month-old PS19 and WT mice collected after 7 months of treatment. Data are mean±SEM. n=7-10/group. One-way ANOVA.

DETAILED DESCRIPTION OF THE INVENTION

Figure 1A:
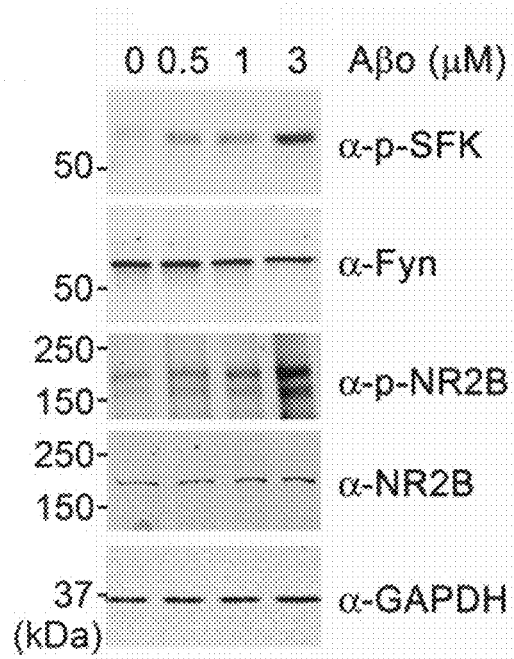
FIGS. 1A-1F illustrate the results of experiments demonstrating that oligomers of Aβ bound to $PrP^C$ activate Fyn to damage neurons in AD.

The present invention relates in part to the discovery that Fyn tyrosine kinase (referred to herein as "Fyn") takes part in mediating the pathological signaling associated with Aβ oligomers (Aβo). In certain embodiments, inhibition of Fyn inhibits Aβo signaling, including phosphorylation of Fyn and eEF2. Thus, the present invention relates generally to compositions and methods for treating and preventing an Aβ-modulated disease. Non-limiting examples of Aβ-modulated disease that are treatable or preventable with the compositions and methods of the present invention include, but are not limited to, Alzheimer's Disease (AD), prodromal Alzheimer's Disease, amnestic mild cognitive impairment (MCI), Down syndrome dementia, traumatic brain injury, Lewy body dementia, Parkinson's Disease with dementia, frontotemporal dementia, and after stroke aphasia.

Accumulation of misfolded phosphorylated Tau (Tauopathy) can be triggered by mutations or by trauma, and is associated with synapse loss, gliosis, neurodegeneration and memory deficits. Fyn kinase physically associates with Tau and regulates subcellular distribution. As demonstrated herein, the present studies assessed whether pharmacological Fyn inhibition alters Tauopathy. In P301S transgenic mice, chronic Fyn inhibition prevented deficits in spatial memory and passive avoidance learning. The behavioral improvement was coupled with reduced accumulation of phospho-Tau in the hippocampus, with reductions in glial activation and with recovery of presynaptic markers. This analysis was extended to a trauma model in which very mild repetitive closed head injury was paired with chronic variable stress over 2 weeks to produce persistent memory deficits and Tau accumulation. In this model, Fyn inhibition beginning 24 hours after the trauma ended rescued memory performance and reduced Tau accumulation. Thus, inhibition of Fyn kinase can have therapeutic benefit in clinical Tauopathies.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

Generally, the nomenclature used herein and the laboratory procedures in cell culture, molecular genetics, pharmacology and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. In certain embodiments, the term "about" encompasses variations of ±10%.

As used herein, an "Aβ-modulated disease" or "Aβ-modulated disorder" refers to a neurological disease that is associated with pathological Aβ accumulation or Aβ-mediating signaling. Non-limiting examples of such diseases encompass, but are not limited to, Alzheimer's Disease (AD), prodromal Alzheimer's Disease, amnestic mild cognitive impairment (MCI), Down syndrome dementia, traumatic brain injury, Lewy body dementia, Parkinson's Disease with dementia, frontotemporal dementia, and after stroke aphasia.

As used herein, the term "AD" refers to Alzheimer's Disease.

A disease or disorder is "alleviated" if the severity or frequency of at least one sign or symptom of the disease or disorder experienced by a patient is reduced.

As used herein, the terms "analog," "analogue," or "derivative" are meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically.

The term "antibody" as used herein refers to an immunoglobulin molecule that is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, the term "AZD0530" or "saracatinib" refers to N-(5-chloro-benzo[d][1,3]dioxol-4-yl)-7-(2-(4-methyl piperazin-1-yl)ethoxy)-5-(tetrahydro-2H-pyran-4-yloxy)quinazolin-4-amine, or a pharmaceutically acceptable salt or solvate thereof. Saracatinib and therapeutic salts thereof are described for example in PCT Application Publications No. WO 01/94341 and WO 06/064217, both of which are hereby incorporated herein by reference in their entireties.

As used herein, the term "saracatinib free base" refers to N-(5-chloro-benzo[d][1,3]dioxol-4-yl)-7-(2-(4-methyl piperazin-1-yl)ethoxy)-5-(tetrahydro-2H-pyran-4-yloxy)quinazolin-4-amine, which is not part of an acid- or base-addition salt. Saracatinib free base has the molecular mass of 542.04 g/mole.

As used herein, the term "saracatinib difumarate" refers to the salt comprising one molecule of N-(5-chloro-benzo[d][1,3]dioxol-4-yl)-7-(2-(4-methyl piperazin-1-yl)ethoxy)-5-(tetrahydro-2H-pyran-4-yloxy)quinazolin-4-amine and two molecules of fumaric acid. Saracatinib difumarate has the molecular mass of 774.18 g/mole. It follows that 1.00 g of saracatinib difumarate comprises 0.700 g of saracatinib free base, and 1.00 g of saracatinib free base corresponds to 1.429 g of saracatinib difumarate.

As used herein, unless stated otherwise, numeric dose values of AZD0530 or saracatinib correspond to the free base of saracatinib. However, one skilled in the art will note that a concentration of saracatinib expressed in molar units relates to both saracatinib free base and a saracatinib salt comprising one molecule of saracatinib free base. For example, a 1 mM saracatinib difumarate solution, a 1 mM saracatinib dihydrochloride solution, a 1 mM saracatinib sulfate solution, and a 1 mM saracatinib free base solution are all 1 mM in saracatinib.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "constitutive" promoter is a nucleotide sequence which, when operably linked with a polynucleotide which encodes or specifies a gene product, causes the gene product to be produced in a cell under most or all physiological conditions of the cell.

As used herein, the term "CSF" refers to cerebrospinal fluid, which is a clear colorless bodily fluid found in the brain and spine.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The phrase "Fyn inhibitor," or "inhibitor of Fyn" as used herein, refers to a composition or compound that inhibits at least in part, as compared to the control system that lacks the inhibitor, Fyn activity, Fyn expression and/or both, either directly or indirectly, using any method known to the skilled artisan. A Fyn inhibitor may be any type of compound, including but not limited to, a nucleic acid, peptide, antibody, small molecule, antagonist, aptamer, or peptidomimetic.

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

An "inducible" promoter is a nucleotide sequence which, when operably linked with a polynucleotide which encodes or specifies a gene product, causes the gene product to be produced substantially only when an inducer which corresponds to the promoter is present.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide," refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, a "peptidomimetic" is a compound containing non-peptidic structural elements that is capable of mimicking the biological action of a parent peptide. A peptidomimetic may or may not comprise peptide bonds.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" or "therapeutically acceptable salt" refers to a salt of the administered compounds prepared from pharmaceutically acceptable non-toxic acids, including inorganic acids, organic acids, solvates, hydrates, or clathrates thereof.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein, the terms "polypeptide," "protein" and "peptide" are used interchangeably and refer to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

Conventional notation is used herein to portray polypeptide sequences: the left-hand end of a polypeptide sequence is the amino-terminus; the right-hand end of a polypeptide sequence is the carboxyl-terminus.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

As used herein, the term "promoter/regulatory sequence" means a nucleic acid sequence that is required for expression of a gene product operably linked to the promoter/regulator sequence. In some instances, this sequence may be the core promoter sequence and in other instances, this sequence may also include an enhancer sequence and other regulatory elements that are required for expression of the gene product. The promoter/regulatory sequence may, for example, be one which expresses the gene product in an inducible manner.

As used herein, a "recombinant cell" is a host cell that comprises a recombinant polynucleotide.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods. A host cell that comprises a recombinant polynucleotide is referred to as a "recombinant host cell." A gene which is expressed in a recombinant host cell wherein the gene comprises a recombinant polynucleotide, produces a "recombinant polypeptide."

By the term "specifically binds," as used herein, is meant a molecule, such as an antibody, which recognizes and binds to another molecule or feature, but does not substantially recognize or bind other molecules or features in a sample.

The terms "subject" or "patient" or "individual" for the purposes of the present invention includes humans and other animals, particularly mammals, and other organisms. Thus the methods are applicable to both human therapy and veterinary applications. In a specific embodiment the patient is a mammal, and in another specific embodiment the patient is human.

As used herein, the term "therapeutically effective amount" is an amount of a compound of the invention, that when administered to a patient, ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "trough," as relating to a drug that is administered periodically to a subject, corresponds to the drug concentration that is observed in the subject just before the administration of the next dose of drug to the subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates generally to compositions and methods for treating and preventing an Aβ-modulated disease in a subject in need thereof. The invention is useful, for example, for slowing or halting the progression of an Aβ-modulated disease. In certain embodiments, the disease or disorder contemplated within the invention is associated with pathological Aβ accumulation or Aβ-mediating signaling.

The present invention relates generally to compositions and methods for treating and preventing a Tauopathy in a subject in need thereof. The invention is useful, for example, for slowing or halting the progression of a Tauopathy.

Non-limiting examples of Aβ-modulated disease that are treatable or preventable with the compositions and methods of the present invention include, but are not limited to, Alzheimer's Disease (AD), prodromal Alzheimer's Disease, amnestic mild cognitive impairment (MCI), Down syndrome dementia, traumatic brain injury, Lewy body dementia, Parkinson's Disease with dementia, fronto-temporal dementia (including fronto-temporal lobar dementia), and after stroke aphasia. It should be noted that the present invention is not limited to a particular type of Aβ-modulated disease.

In one aspect, the present invention relates to the discovery of the role of Fyn tyrosine kinase (referred to herein as "Fyn") in mediating the pathological signaling associated with Aβ oligomers (Aβo). As demonstrated herein, inhibition of Fyn inhibits Aβo signaling, including phosphorylation of Fyn and eEF2.

In another aspect, the present invention provides a composition for treating an Aβ-modulated disease in a subject, wherein the composition comprises an inhibitor of Fyn activity. In other embodiments, the present invention provides a composition for treating an Aβ-modulated disease in a subject, wherein the composition comprises an inhibitor of Fyn expression.

In another aspect, the present invention provides a composition for treating a Tauopathy in a subject, wherein the composition comprises an inhibitor of Fyn activity. In other embodiments, the present invention provides a composition for treating a Tauopathy in a subject, wherein the composition comprises an inhibitor of Fyn expression.

In certain embodiments, the composition comprises an inhibitor of Fyn expression. For example, in certain embodiments, the composition comprises an isolated nucleic acid (e.g., siRNA, ribozyme, antisense RNA, etc.) that reduces the expression level of Fyn in a cell.

In certain embodiments, the composition comprises an inhibitor of Fyn activity. For example, in certain embodiments, the composition comprises an isolated nucleic acid, isolated peptide, antibody, small molecule, antagonist, aptamer, or peptidomimetic that reduces the activity of Fyn.

In certain embodiments, small molecules or peptidomimetics contemplated herein are prepared as prodrugs. A prodrug is an agent converted into the parent drug in vivo. In one embodiment, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound. Prodrugs are known to those skilled in the art, and may be prepared using methodology described in the art.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include are not limited to $^2$H, $^3$H, $^{13}$C, $^{14}$C, $^{36}$C $^{18}$F, $^{123}$I, $^{125}$I, $^{13}$N, $^{15}$N, $^{15}$O, $^{17}$O, $^{18}$O, $^{32}$P, and $^{35}$S. In one embodiment, the isotope comprises deuterium. In certain embodiments, isotopically labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

In certain embodiments, the composition comprises AZD0530 (also known as saracatinib, or N-(5-chlorobenzo[d][1,3]dioxol-4-yl)-7-(2-(4-methyl piperazin-1-yl)ethoxy)-5-(tetrahydro-2H-pyran-4-yloxy)quinazolin-4-amine), or pharmaceutically acceptable salts, prodrugs, solvates or derivatives thereof.

In certain embodiments, the invention provides a pharmaceutical composition comprising an effective amount of saracatinib, or a pharmaceutically acceptable salt, solvate or prodrug thereof, such that administration to a mammal of the effective amount of saracatinib, or a pharmaceutically acceptable salt or solvate thereof, affords a trough CSF concentration of saracatinib in the mammal of at least about 0.9 nM. In other embodiments, the trough CSF concentration of saracatinib in the mammal is at least about 2.1 nM. In yet other embodiments, the trough CSF concentration of saracatinib in the mammal is at least about 2.5 nM. In yet other embodiments, the trough CSF concentration of saracatinib in the mammal ranges from about 0.9 nM to about 2.2 nM. In yet other embodiments, the trough CSF concentration of saracatinib in the mammal ranges from about 2.1 nM to about 8.3 nM. In yet other embodiments, the trough CSF concentration of saracatinib in the mammal ranges from about 2.5 nM to about 14.0 nM. In yet other embodiments, the trough CSF concentration of saracatinib in the mammal ranges from about 0.9 nM to about 14.0 nM. In yet other embodiments, the average brain concentration of saracatinib in the mammal is selected from the group consisting of at least about 3 nM, at least about 7 nM, and at least about 8 nM. In yet other embodiments, the average brain concentration of saracatinib in the mammal ranges from about 3 to about 46 nM.

In certain embodiments, the pharmaceutical composition is coformulated with at least one additional agent that treats or prevents an Aβ-modulated disease in a mammal, and/or that improves or prevents further loss of cognition in a mammal.

In certain embodiments, the saracatinib is saracatinib free base. In other embodiments, the saracatinib is saracatinib difumarate. In yet other embodiments, the saracatinib is selected from the group consisting of saracatinib free base, saracatinib difumarate, and any combinations thereof.

In certain embodiments, the present invention provides a method for treating or preventing an Aβ-modulated disease in a subject. In certain embodiments, the method comprises administering to the subject an effective amount of an inhibitor of Fyn. For example, in certain embodiments, the method comprises administering to a subject an effective amount of saracatinib, or salts, prodrugs or derivatives thereof. In other instances, administration of a Fyn inhibitor reduces pathological Aβ mediated signaling and/or reduces the progression of an Aβ-modulated disease.

In certain embodiments, the present invention provides a method for improving or preventing further loss of cognition in a subject. In certain embodiments, the method comprises administering to the subject an effective amount of an inhibitor of Fyn. For example, in certain embodiments, the method comprises administering to a subject an effective amount of saracatinib, or salts, prodrugs or derivatives thereof. In other instances, administration of a Fyn inhibitor restores or prevents further loss of synapse density in the subject.

In certain embodiments, the present invention provides a method of treating, ameliorating, or inhibiting further development of a Tauopathy in a mammal in need thereof. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof. In certain embodiments, accumulation of hyperphosphorylated Tau protein is reversed, inhibited, or minimized in the mammal. In certain embodiments, the method further comprises administering to the mammal at least one additional agent that treats, ameliorates, or inhibits further development of the Tauopathy in the mammal. In certain embodiments, the inhibitor and at least one additional agent are coformulated.

In certain embodiments, the present invention provides a method of improving memory, ameliorating loss of memory, or preventing further loss of memory in a mammal afflicted with a Tauopathy. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof.

In certain embodiments, the present invention provides a method of treating, ameliorating, or preventing further development of at least one of hyperphosphorylated Tau accumulation, synapse loss, and memory deficit in a mammal afflicted with traumatic brain injury. In certain embodiments, the method comprises administering to the mammal a therapeutically effective amount of a Fyn inhibitor after the mammal suffers the traumatic brain injury. In certain embodiments, the administering minimizes, reduces, or reverses at least one of gliosis, neurodegeneration, and neurological function deficits in the afflicted mammal. In certain embodiments, the administering takes place 16 weeks or less after the traumatic brain injury. In certain embodiments, the administering takes place 15 weeks or less after the traumatic brain injury. In certain embodiments, the administering takes place 14 weeks or less after the traumatic brain injury. In certain embodiments, the administering takes place 13 weeks or less after the traumatic brain injury. In certain embodiments, the administering takes place 12 weeks or less after the traumatic brain injury. In certain embodiments, the administering takes place 11 weeks or less after the traumatic brain injury. In certain embodiments, the administering takes place 10 weeks or less after the traumatic brain injury. In certain embodiments, the administering takes place 9 weeks or less after the traumatic brain injury. In certain embodiments, the administering takes place 8 weeks or less after the traumatic brain injury. In certain embodiments, the administering takes place 7 weeks or less after the traumatic brain injury. In certain embodiments, the administering takes place 6 weeks or less after the traumatic brain injury. In certain embodiments, the administering takes place 5 weeks or less after the traumatic brain injury. In certain embodiments, the administering takes place 4 weeks or less after the traumatic brain injury. In certain embodiments, the administering takes place 3 weeks or less after the traumatic brain injury. In certain embodiments, the administering takes place 21 days or less after the traumatic brain injury. In certain embodiments, the administering takes place 20 days or less after the traumatic brain injury. In certain embodiments, the administering takes place 19 days or less after the traumatic brain injury. In certain embodiments, the administering takes place 18 days or less after the traumatic brain injury. In certain embodiments, the administering takes place 17 days or less after the traumatic brain injury. In certain embodiments, the administering takes place 16 days or less after the traumatic brain injury. In certain embodiments, the administering takes place 15 days or less after the traumatic brain injury. In certain embodiments, the administering takes place 14 days or less after the traumatic brain injury. In certain embodiments, the administering takes place 13 days or less after the traumatic brain injury. In certain embodiments, the administering takes place 12 days or less after the traumatic brain injury. In certain embodiments, the administering takes place 11 days or less after the traumatic brain injury. In certain embodiments, the administering takes place 10 days or less after the traumatic brain injury. In certain embodiments, the administering takes place 9 days or less after the traumatic brain injury. In certain embodiments, the administering takes place 8 days or less after the traumatic brain injury. In certain embodiments, the administering takes place 7 days or less after the traumatic brain injury. In certain embodiments, the administering takes place 6 days or less after the traumatic brain injury. In certain embodiments, the administering takes place 5 days or less after the traumatic brain injury. In certain embodiments, the administering takes place 4 days or less after the traumatic brain injury. In certain embodiments, the administering takes place 3 days or less after the traumatic brain injury. In certain embodiments, the administering takes place 2 days or less after the traumatic brain injury. In certain embodiments, the administering takes place 1 day or less after the traumatic brain injury. In certain embodiments, the administering takes place 24 hours or less after the traumatic brain injury. In certain embodiments, the administering takes place 22 hours or less after the traumatic brain injury. In certain embodiments, the administering takes place 20 hours or less after the traumatic brain injury. In certain embodiments, the administering takes place 18 hours or less after the traumatic brain injury. In certain embodiments, the administering takes place 16 hours or less after the traumatic brain injury. In certain embodiments, the administering takes place 14 hours or less after the traumatic brain injury. In certain embodiments, the administering takes place 12 hours or less after the traumatic brain injury. In certain embodiments, the administering takes place 10 hours or less after the traumatic brain injury. In certain embodiments, the administering takes place 8 hours or less after the traumatic brain injury. In certain embodiments, the administering takes place 6 hours or less after the traumatic brain injury. In certain embodiments, the administering takes place 5 hours or less after the traumatic brain injury. In certain embodiments, the administering takes place 4 hours or less after the traumatic brain injury. In certain embodiments, the administering takes place 3 hours or less after the traumatic brain injury. In certain embodiments, the administering takes place 2 hours or less after the traumatic brain injury. In certain embodiments, the administering takes place 1 hour or less after the traumatic brain injury. In certain embodiments, the administering takes place 60 minutes or less after the traumatic brain injury. In certain embodiments, the administering takes place 45 minutes or less after the traumatic brain injury. In certain embodiments, the administering takes place 30 minutes or less after the traumatic brain injury. In certain embodiments, the administering takes place 15 minutes or less after the traumatic brain injury.

Inhibitors

In certain embodiments, the present invention provides a composition for treating or preventing an Aβ-modulated disease in a subject. In other embodiments, the composition inhibits the expression and/or activity of Fyn in a cell of the subject. For example, in certain embodiments, the inhibitor reduces the level of Aβo-induced Fyn activation in the subject.

In certain embodiments, the composition of the invention comprises an inhibitor of Fyn. An inhibitor of Fyn is any compound, molecule, or agent that reduces, inhibits, or prevents the function of Fyn. For example, an inhibitor of Fyn is any compound, molecule, or agent that reduces Fyn expression and/or activity. In certain embodiments, an inhibitor of Fyn comprises an isolated nucleic acid, isolated peptide, small molecule, siRNA, ribozyme, antisense nucleic acid, antagonist, aptamer, peptidomimetic, or any combinations thereof.

In certain embodiments, the inhibitor of the invention is an antagonist of Fyn. For example, in certain embodiments, the inhibitor specifically binds to Fyn, thus preventing access of Fyn to a target substrate.

Small Molecule Inhibitors

In certain embodiments, the inhibitor comprises a small molecule. When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In certain embodiments, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

Small molecule inhibitors of Fyn are known in the art. Non-limiting examples of small molecule inhibitors of Fyn include, but are not limited to, saracatinib, SKI-606 (bosutinib, or 4-[(2,4-dichloro-5-methoxyphenyl)amino]-6-methoxy-7-[3-(4-methylpiperazin-1-yl)propoxy]quinoline-3-carbonitrile), BMS-354825 (dasatinib, or N-(2-chloro-6-methyl phenyl)-2-[[6-[4-(2-hydroxyethyl)-1-piperazinyl]-2-methyl-4-pyrimidinyl]amino]-5-thiazole carboxamide), AP24534 (ponatinib, or 3-(2-imidazo[1,2-b]pyridazin-3-yl-ethynyl)-4-methyl-N-[4-[(4-methylpiperazin-1-yl)methyl]-3-(trifluoromethyl)phenyl]benzamide), PP2 (4-amino-5-(4-chlorophenyl)-7-(dimethylethyl)pyrazolo[3,4-d]pyrimidine, CAS #172889-27-9), any salt, prodrug or solvate thereof, or any combinations thereof.

The small molecule and small molecule compounds described herein may be present as salts even if salts are not depicted and it is understood that the invention embraces all salts, prodrugs and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted.

The invention also includes any or all of the stereochemical forms, including any enantiomeric or diastereoisomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In certain embodiments, the small molecule inhibitor of the invention comprises an analog or derivative of an inhibitor described herein. In other embodiments, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analogued as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

In certain embodiments, the small molecule inhibitors described herein can independently be derivatized/analogued by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In certain embodiments, the inhibitor comprises an isolated nucleic acid. In other embodiments, the inhibitor is an siRNA or antisense molecule, which inhibits Fyn. In yet other embodiments, the nucleic acid comprises a promoter/regulatory sequence such that the nucleic acid is preferably capable of directing expression of the nucleic acid. Thus, the invention provides expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In certain embodiments, Fyn can be inhibited by way of inactivating and/or sequestering Fyn. As such, inhibiting the activity of Fyn can be accomplished by using a transdominant negative mutant.

In certain embodiments, siRNA is used to decrease the level of Fyn protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; Engelke, Ed., RNA Interference (RNAi) Nuts & Bolts of RNAi Technology, DNA Press, Eagleville, P A (2003); and Hannon, Ed., RNAi A Guide to Gene Silencing, Cold Spring Harbor Laboratory Press, Cold Spring Harbor, N.Y. (2003). Soutschek et al. (2004, Nature 432:173-178) describes a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of Fyn using RNAi technology.

In certain embodiments, the invention provides a vector comprising an siRNA or antisense polynucleotide. In other embodiments, the siRNA or antisense polynucleotide inhibits the expression of Fyn. The incorporation of a desired polynucleotide into a vector and the choice of vectors is well-known in the art.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In certain embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In certain embodiments, the vector of the invention is an expression vector. Suitable host cells include a wide variety of prokaryotic and eukaryotic host cells. In certain embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid that is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In certain embodiments, the vector is a vector useful for transforming animal cells.

In certain embodiments, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

It will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the siRNA polynucleotide, a skilled artisan will understand that the siRNA polynucleotide has certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl- methyl-, thio- and other modified forms of adenine, cytidine, guanine, thymine, and uridine.

In certain embodiments, an antisense nucleic acid sequence expressed by a plasmid vector is used to inhibit Fyn protein expression. The antisense expressing vector is used to transfect a mammalian cell or the mammal itself, thereby causing reduced endogenous expression of Fyn.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In certain embodiments, a ribozyme is used to inhibit Fyn protein expression. Ribozymes useful for inhibiting the expression of a target molecule may be designed by incorporating target sequences into the basic ribozyme structure which are complementary, for example, to the mRNA sequence encoding Fyn. Ribozymes targeting Fyn, may be synthesized using commercially available reagents (Applied Biosystems, Inc., Foster City, Calif.) or they may be genetically expressed from DNA encoding them.

Polypeptide Inhibitors

In certain embodiments, the invention includes an isolated peptide inhibitor that inhibits Fyn. For example, in certain embodiments, the peptide inhibitor of the invention inhibits Fyn directly by binding to Fyn, thereby preventing the normal functional activity of Fyn. In other embodiments, the peptide inhibitor of the invention inhibits Fyn by competing with endogenous Fyn. In yet other embodiments, the peptide inhibitor of the invention inhibits the activity of Fyn by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

The invention also provides an inhibitor of Fyn comprising an antibody, or antibody fragment, specific for Fyn. That is, the antibody can inhibit Fyn to provide a beneficial effect.

The antibodies may be intact monoclonal or polyclonal antibodies, and immunologically active fragments (e.g., a Fab or (Fab)$_2$ fragment), an antibody heavy chain, an antibody light chain, humanized antibodies, a genetically engineered single chain Fv molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art.

Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, P3-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Pharmaceutical Compositions

The present invention includes pharmaceutical compositions comprising one or more inhibitors of Fyn. The formulations of the pharmaceutical compositions described herein may be prepared by any method known or hereafter developed in the art of pharmacology. In general, such preparatory methods include the bringing the active ingredient into association with a carrier or one or more other accessory ingredients, and then, if necessary or desirable, shaping or packaging the product into a desired single- or multi-dose unit.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from ng/kg/day and 100 mg/kg/day. In certain embodiments, the invention envisions administration of a dose which results in a concentration of the compound of the present invention from 1 µM and 10 µM in a mammal. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-AD agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

In one embodiment, the tablets of the invention comprise saracatinib difumarate, mannitol, dibasic calcium phosphate anhydrous, crospovidone, hypromellose and magnesium stearate, with a film-coat containing hypromellose, macrogol 400, red iron oxide, black iron oxide and titanium dioxide. In other embodiments, the tablets of the invention comprise about 50 or 125 mg of saracatinib expressed as free base. In yet other embodiments, the tablets of the invention comprise about 71.4 or 178.6 mg of saracatinib expressed as difumarate salt.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Combination Therapies

In certain embodiments, the compounds of the invention are useful in the methods of the invention in combination with at least one additional agent useful for treating or preventing an Aβ-modulated disease, and/or improving or preventing further loss in cognition, in a mammal in need thereof. This additional agent may comprise compounds identified herein or compounds, e.g., commercially available compounds, known to treat, prevent or reduce the symptoms of an Aβ-modulated disease in a subject.

In certain embodiments, the at least one additional compound useful for treating or preventing an Aβ-modulated disease comprises acetylcholinesterase inhibitors, such as, but not limited to donepezil ((RS)-2-[(1-benzyl-4-piperidyl) methyl]-5,6-dimethoxy-2,3-dihydroinden-1-one) or memantine (3,5-dimethyladamantan-1-amine). In other embodiments, the at least one additional compound useful for treating or preventing an Aβ-modulated disease comprises an anti-amyloid agent, such as an antibody or a small molecule.

In certain embodiments, the at least one additional compound useful for improving or preventing further loss in cognition comprises a drug approved for treating Alzheimer's Disease, such as acetylcholinesterase inhibitors (such as donepezil) or memantine.

A synergistic effect may be calculated, for example, using suitable methods such as, for example, the Sigmoid-$E_{max}$ equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

The invention includes a kit comprising at least one Fyn inhibitor, an applicator, and an instructional material for use thereof. In certain embodiments, the Fyn inhibitor comprises at least one selected from the group consisting of saracatinib free base and saracatinib difumarate.

The instructional material included in the kit comprises instructions for preventing or treating an Aβ-modulated disease in a mammal. The instructional material recites the amount of, and frequency with which, the Fyn inhibitor should be administered to the mammal. In other embodiments, the kit further comprises at least one additional agent that prevents or treats an Aβ-modulated disease in a mammal. In other embodiments, the kit further comprises at least one additional agent that improves and/or prevent further loss of cognition in a mammal.

Methods

The present invention provides methods of treating or preventing an Aβ-modulated disease. In certain embodiments, the method comprises administering an effective amount of a composition that inhibits Fyn expression and/or Fyn activity. In certain embodiments, the method of the invention comprises administering to a subject an effective amount of a composition that inhibits the expression and/or activity of Fyn in a neuron of the subject.

The present invention provides a method of treating or preventing an Aβ-modulated disease or disorder in a mammal in need thereof, the method comprising administering to the mammal a therapeutically effective amount of a pharmaceutical composition comprising a Fyn inhibitor.

The present invention provides a method of treating, ameliorating, or inhibiting further development of a Tauopathy in a mammal in need thereof. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof. In certain embodiments, accumulation of hyperphosphorylated Tau protein is reversed, inhibited, or minimized in the mammal.

In certain embodiments, the present invention provides a method of improving memory, ameliorating loss of memory, or preventing further loss of memory in a mammal afflicted with a Tauopathy. In certain embodiments, the method comprises administering to the mammal a therapeutically effective amount of a Fyn inhibitor. In certain embodiments, the Tauopathy comprises at least one of traumatic brain injury, fronto-temporal dementia, after stroke aphasia, and any combinations thereof.

In certain embodiments, the present invention provides a method of treating, ameliorating, or preventing further development of at least one of hyperphosphorylated Tau accumulation, synapse loss, and memory deficit in a mammal afflicted with traumatic brain injury. In certain embodiments, the method comprises administering to the mammal a therapeutically effective amount of a Fyn inhibitor after the mammal suffers the traumatic brain injury. In certain embodiments, the administering minimizes, reduces, or reverses at least one of gliosis, neurodegeneration, and neurological function deficits in the afflicted mammal. In certain embodiments, the administering takes place 16 weeks or less after the traumatic brain injury.

In certain embodiments, the Aβ-modulated disease or disorder is selected from the group consisting of Alzheimer's Disease (AD), prodromal Alzheimer's Disease, amnestic mild cognitive impairment (MCI), Down syndrome dementia, traumatic brain injury, Lewy body dementia, Parkinson's Disease with dementia, fronto-temporal dementia (including fronto-temporal lobar dementia), after stroke aphasia, and any combinations thereof.

In certain embodiments, Aβ oligomer-induced signaling is inhibited in the mammal.

In certain embodiments, the Fyn inhibitor is selected from the group consisting of a nucleic acid, siRNA, antisense nucleic acid, ribozyme, peptide, antibody, small molecule, antagonist, aptamer, peptidomimetic, and any combinations thereof. In other embodiments, the Fyn small molecule inhibitor is selected from the group consisting of saracatinib, bosutinib, dasatinib, ponatinib, PP2, a salt, prodrug or solvate thereof, a derivative thereof, and any combinations thereof. In yet other embodiments, the Fyn small molecule inhibitor is saracatinib, or a pharmaceutically acceptable salt, prodrug or solvate thereof.

In certain embodiments, the Fyn inhibitor comprises at least one selected from the group consisting of saracatinib free base and saracatinib difumarate.

In certain embodiments, the administration of the composition to the mammal affords a trough CSF concentration of saracatinib in the mammal of at least about 0.9 nM. In other embodiments, the trough CSF concentration of saracatinib in the mammal is selected from the group consisting of at least about 2.1 nM and at least 2.5 nM. In yet other embodiments, the trough CSF concentration of saracatinib is in the range selected from the group consisting of from about 0.9 nM to about 2.2 nM, from about 2.1 nM to about 8.3 nM, and from about 2.5 nM to about 14.0 nM.

In certain embodiments, the composition is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

In certain embodiments, the method further comprises administering to the mammal at least one additional agent that treats or prevents the Aβ-modulated disease or disorder in the mammal. In other embodiments, the method further comprises administering to the mammal at least one additional agent that treats, ameliorates, or inhibits further development of the Tauopathy in the mammal. In yet other embodiments, the composition and at least one additional agent are coformulated. In yet other embodiments, the mammal is human.

In certain embodiments, the human is administered a daily dose of saracatinib, or a pharmaceutically acceptable salt thereof, that comprises an amount of at least 50 mg of saracatinib free base. In other embodiments, the human is administered a daily dose of saracatinib, or a pharmaceutically acceptable salt thereof, that comprises an amount of at least 100 mg of saracatinib free base. In yet other embodiments, the human is administered a daily dose of saracatinib, or a pharmaceutically acceptable salt thereof, that comprises an amount of at least 125 mg of saracatinib free base.

In certain embodiments, the human is administered a daily dose of saracatinib, or a pharmaceutically acceptable salt thereof, that comprises an amount of about 50 mg of saracatinib free base. In other embodiments, the human is administered a daily dose of saracatinib, or a pharmaceutically acceptable salt thereof, that comprises an amount of about 100 mg of saracatinib free base. In yet other embodiments, the human is administered a daily dose of saracatinib, or a pharmaceutically acceptable salt thereof, that comprises an amount of about 125 mg of saracatinib free base.

In certain embodiments, the human is administered a daily dose of saracatinib, or a pharmaceutically acceptable salt thereof, that comprises an amount ranging from about 45 to about 55 mg of saracatinib free base. In other embodiments, the human is administered a daily dose of saracatinib, or a pharmaceutically acceptable salt thereof, that comprises an amount ranging from about 90 to about 110 mg of saracatinib free base. In yet other embodiments, the human is administered a daily dose of saracatinib, or a pharmaceutically acceptable salt thereof, that comprises an amount ranging from about 112.5 to about 137.5 mg of saracatinib free base.

In certain embodiments, the human is administered a daily dose of about 50 mg of saracatinib free base. In yet other embodiments, the human is administered a daily dose of about 100 mg of saracatinib free base. In yet other embodiments, the human is administered a daily dose of about 125 mg of saracatinib free base.

In certain embodiments, the human is administered a daily dose of saracatinib free base ranging from about 45 to about 55 mg. In yet other embodiments, the human is administered a daily dose of saracatinib free base ranging from about 90 to about 110 mg. In yet other embodiments, the human is administered a daily dose of saracatinib free base ranging from about 112.5 to about 137.5 mg.

In certain embodiments, the human is administered a daily dose of about 71.4 mg of saracatinib difumarate. In yet other embodiments, the human is administered a daily dose of about 142.9 mg of saracatinib difumarate. In yet other embodiments, the human is administered a daily dose of about 178.6 mg of saracatinib difumarate.

In certain embodiments, the human is administered a daily dose of saracatinib difumarate ranging from about 64.3 to about 78.6 mg. In yet other embodiments, the human is administered a daily dose of saracatinib difumarate ranging from about 128.6 to about 157.2 mg. In yet other embodiments, the human is administered a daily dose of saracatinib difumarate ranging from about 160.7 to about 196.5 mg.

Fyn activity can be inhibited using any method known to the skilled artisan. Examples of methods that inhibit Fyn activity, include but are not limited to, inhibiting expression of an endogenous gene encoding Fyn, decreasing expression of mRNA encoding Fyn, and inhibiting the function, activity, or stability of Fyn. A Fyn inhibitor may therefore be a compound that decreases expression of a gene encoding Fyn, decreases RNA half-life, stability, or expression of a mRNA encoding Fyn protein, or inhibits Fyn function, activity or stability. A Fyn inhibitor may be any type of compound, including but not limited to, a peptide, a nucleic acid, an aptamer, a peptidometic, an antibody, and a small molecule, or combinations thereof.

Fyn inhibition may be accomplished either directly or indirectly. For example Fyn may be directly inhibited by compounds or compositions that directly interact with Fyn, such as antibodies. Alternatively, Fyn may be inhibited indirectly by compounds or compositions that inhibit Fyn downstream effectors, or upstream regulators which up-regulate Fyn expression.

Decreasing expression of an endogenous gene includes providing a specific inhibitor of gene expression. Decreasing expression of mRNA or protein includes decreasing the half-life or stability of mRNA or decreasing mRNA expression. Methods of decreasing expression of Fyn include, but are not limited to, methods that use an siRNA, a microRNA, an antisense nucleic acid, a ribozyme, an expression vector encoding a transdominant negative mutant, a peptide, an antibody, a small molecule, and combinations thereof.

Administration of a Fyn inhibitor in a method of treatment can be achieved in a number of different ways, using methods known in the art. It will be appreciated that a Fyn inhibitor of the invention may be administered to a subject either alone, or in conjunction with another therapeutic agent. For example, a Fyn inhibitor may be administered in combination with one or more therapeutic agents known, or hypothesize to, treat an Aβ-modulated disease.

In one embodiment, the Fyn inhibitor is administered to a subject. The inhibitor may also be a hybrid or fusion composition to facilitate, for instance, delivery to target cells or efficacy. In one embodiment, a hybrid composition may comprise a tissue-specific targeting sequence. For example, in one embodiment, the inhibitor is targeted to a neuron.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods:

HPLC Assay for Saracatinib:

Chromatographic Conditions:

Mobile Phase: 60/40% w/v methanol/ammonium formate 10 mM;

Column: Advanced Chromatography Technologies (ACT) ACE C 18, 5 cm×4.6 mm supplied by Hichrom. Part no ACE-111-0546;

Column Temperature: 30° C.;

Flow Rate: 1 ml/min;

Wavelength: 259 nm;

Injection Volume: 10 µl;

Run Time: 20 min;

Typical Retention Time: approx 2 min.

Preparation of Standard Solution.

A stock standard solution was prepared at approximately 0.1 mg/ml in sample and standard diluent using sonication as required. As required, the solution was diluted to within the linear range.

Validation Summary:

Linearity of the method was confirmed over the concentration range 0.001114 mg/ml to 0.1114 mg/ml.

Precision has been confirmed at 0.001114 mg/ml, 0.02227 mg/ml and 0.1114 mg/ml.

The limit of quantitation was 0.001114 mg/ml.

Analysis of Saracatinib:

Plasma samples are analyzed using solid-phase extraction followed by HPLCMS/MS. The lower and upper limits of quantification (LLOQ and ULOQ) for the standard curve were 0.350 and 175 ng/ml for saracatinib. Calibration, quality control (QC) or blank plasma samples (200 µL) are pipetted into a standard 96-well plate. The appropriate internal standard (20 µL) is added to all samples (except the double blank to which 20 µL of methanol is added). 2% ammonium solution (1000 µL) is added to all wells and mixed. Solid-phase extraction is performed using Oasis HLB 30 mg 1 mL 96-well plates. The samples are conditioned with 1 mL methanol then 1 mL 2% ammonium solution. A 1 mL sample is loaded, washed with 1 mL 25:75, v:v methanol:water and eluted with 0.8 mL methanol. The samples are dried under oxygen-free nitrogen at 35° C. The dry residues are reconstituted in 200 µL of mobile phase, vortex mixed and transferred to 96-well plates. The vials are loaded onto HPLC-MS/MS and injected onto the reversed phase HPLC system. Calibration samples are prepared and analyzed in duplicate at LLOQ (lower limit of quantification) and ULOQ (upper limit of quantitation) and singly at all other levels. Independently prepared QC samples covering the calibration range are analyzed in duplicate and in triplicate at the dilution QC level. Plasma concentration data are quantified using an HPLC-MS/MS method and analyzed by standard methods using WinNonLin version 4.1 (Pharsight Corporation, Mountain View, Calif.).

Materials and Methods for Example 4

Animals

Tau P301S PS19 mice (Yoshiyama et al., 2007, Neuron 53:337-351) were obtained from JAX Laboratory and bred at Yale. They express a mutant human MAPT gene which results in a five-fold greater amount of human Tau proteins than the endogenous Tau produced naturally by mice. There were two cohorts generated for these experiments. Twenty wild-type (WT) and twenty Tau P301S PS19 mice were randomly divided into four experimental groups for the first cohort (Genotype, Treatment (Male, Female)): WT, Vehicle (8, 3); WT, AZD0530 (7, 2); PS19, Vehicle (5, 5); PS19, AZD0530 (5, 5). Eighteen WT mice and eighteen PS19 mice were randomly divided into four experimental groups for the second cohort: WT, Vehicle (4, 5); WT, AZD0530 (6, 3); PS19, Vehicle (3, 6); PS19, AZD0530 (2, 7).

Animals were housed in groups with 2-4 animals per cage with access to food and water ad libidium. Mice in the two cohorts were provided with chow formulated with either Vehicle or AZD0530 (depending on the experimental group) at 2 months of age and allowed to eat ad libidium until they were sacrificed at 9 months old and 11 months old, respectively.

Chronic Oral Dose Preparation of AZD0530

AZD0530 (Saracatinib) was prepared as described (Kaufman et al., 2015, Ann Neurol 77, 953-971). To generate chow containing chow for chronic dosing, the compound was incorporated into purified diet pellets by Research Diets, Inc. by dissolving the compound in a solution of 0.5% w/v Hydroxypropylmethylcellulose/0.1% w/v polysorbate 80 at 1.429 mg/ml. Vehicle pellets were purified diet pellets with control Vehicle solution (without drug). The dosage of the drug in the food was calculated to take into account the average amount of food eaten by a mouse in a single day per kg of weight and adjusted to be equivalent to ingesting 5 mg/kg per day.

Brain Tissue Collection

Mice were euthanized with $CO_2$ and perfused with ice-cold PBS for one and a half minutes. The brains were dissected and the hemispheres were divided. The hippocampus and cortex were dissected from the left hemisphere and were individually snap frozen in liquid nitrogen to be used for biochemical analysis. The right hemispheres were fixed in 4% paraformaldehyde in PBS for 24 hours at 4° C. and then placed in PBS with 0.05% Azide to be used for immunohistochemistry.

Brain Protein Extraction

Brain protein extraction was performed as previously described (Takahashi et al., 2017, Acta Neuropathol 133: 785-807) with modifications. The hippocampi were weighed and then homogenized with 20 strokes in ten-fold volume (w/v) of ice-cold 50 mM Tris-HCl, pH 7.5, 150 mM NaCl, PhosSTOP, cOmplete-mini protease inhibitor cocktail (Roche), and 1 mM vanadate. After ultracentrifugation for 20 minutes at 100,000×g at 4° C., the supernatants were collected as TBS-soluble fractions, and the TBS-insoluble pellet was re-suspended in RIPA (25 mM Tris-HCl pH 7.5, 150 mM NaCl, 1% NP40, 0.5% sodium deoxycholate, 0.1% SDS, PhosSTOP, cOmplete-mini (Roche), and 1 mM vanadate) at a volume equivalent to the amount used in the TBS extraction. The samples were incubated in RIPA for 30 minutes at 4° C. and then ultracentrifuged for 20 minutes at 100,000×g at 4° C. The supernatants were collected as RIPA-soluble fractions.

Immunohistochemistry

Immunohistochemistry was performed as previously described (Kaufman et al., 2015, Ann Neurol 77:953-971) with slight modifications. Forty m coronal sections of the right hemisphere were cut with a Leica VT1000S Vibratome. Antigen retrieval was performed on the forty m free-floating sections by incubating three slices from each mouse in 1× Reveal decloaker buffer (Biocare Medical) in 24-well-plates for 10 minutes at 90° C. in an oven and then cooled down at room temperature for 10 minutes. The antigen retrieval step was done for PHF1, AT8, and GFAP stainings. Sections were permeabilized with 0.1% Triton X-100 at room temperature for 5 minutes for PHF1 and SV2A staining and for 30 minutes for CD68/Iba1, AT8, and GFAP. All sections were blocked with 10% donkey, horse, or goat serum in PBS for one hour at room temperature. The sections were then incubated in primary antibody in 4% donkey, horse, or goat serum in PBS overnight at room temperature. For SV2A and PHF1 stainings, primary antibodies were incubated at 4° C. rather than room temperature. The primary antibodies that were used include: PHF1 (gift from Dr. Peter Davies, Albert Einstein College of Medicine, Bronx, N.Y. 1:250), SV2A (Abcam 1:500), CD68 (Biorad 1:900), Iba1 (Wako 1:500), AT8 (Invitrogen 1:500), and GFAP (Abcam 1:1000). The sections were then washed three times with PBS for five minutes each and then incubated for 1-2 hours at room temperature in either donkey anti-rabbit or donkey anti-mouse fluorescent secondary antibodies in PBS (Invitrogen Alexa Fluor 1:500). After incubation, the sections were washed three times with PBS for 5 minutes. To quench autofluorescence for PHF1, AT8, and GFAP stainings, sections were dipped briefly in $dH_2O$ and then incubated in copper sulfate solution (10 mM copper sulfate, 50 mM ammonium acetate, pH 5) for 15 minutes before dipping back into $dH_2O$ and then placed in PBS. All sections were mounted onto glass slides (Superfrost, Fischer Scientific Company L.L.C.) and coverslipped with Vectashield (Vector) antifade mounting medium with DAPI.

Imaging and Analysis of Immunohistochemistry

For imaging and analysis of sections from the transgenic Tauopathy studies, Nikon Eclipse Ti Spinning Disc Confocal Microscope was used with a 40×1.3 NA oil-immersion lens in Cargille immersion oil. For only the low magnification survey of gliosis, a Zeiss Axiolmager Z1 fluorescent microscope was used with a 5× objective. The dentate gyrus, CA1, and CA3 of mice were imaged and the percent positive area for each staining was analyzed with a macro in ImageJ or a pipeline in CellProfiler. For imaging and analysis of sections from the TBI studies, a Zeiss 800 confocal microscope with a 20× objective. All the imaging and analyses were conducted by a researcher who was blinded to the genotype and treatment type.

Immunoblot

Immunoblotting was performed as previously described (Gimbel et al., 2010, J Neurosci 30:6367-6374) with modifications. The RIPA-soluble fraction was mixed in 2× Laemmli Sample Buffer (Bio-Rad) with 0.5% β-mercaptoethanol. The mixture was heated for 5 minutes at 95° C. and then loaded into precast 4-20% Tris-glycine gels (Bio-Rad) to be electrophoresed. The protein was then transferred with an iBlot 2 Transfer Device onto nitrocellulose membranes (Invitrogen IB23001) and then incubated in blocking buffer (Rockland) for 1 hr at room temperature. Membranes were then incubated overnight at 4° C. in blocking buffer with primary antibodies: pSRC (Tyr416) (Cell Signaling 1:1000) and β-actin (Cell Signaling 1:2000). The next day, membranes were washed three times with TBST for 5 minutes and incubated in secondary antibodies (donkey anti-rabbit (800) and donkey anti-mouse (680), Li-Cor IR Dye) for 1 hr at room temperature. Membranes were washed three times with TBST for 5 minutes, visualized with an Odyssey Infrared imaging system (Li-Cor), and then the immunoreactive bands were quantified with ImageJ software.

Morris Water Maze

The Morris water maze paradigm was performed as previously described (Kaufman et al., 2015, Ann Neurol 77:953-971). When conducting all behavioral tests, the investigator was blinded to the mouse's genotype and pharmacological treatment. Prior to behavioral tests, each mouse was handled for 5 minutes for 4 days prior to behavioral tests to reduce anxiety. Mice were placed in a pool with a hidden, clear platform filled with water to 1 cm above the submerged platform. The hidden platform was placed in one of the four quadrants of the pool with the 4 drop zones directly across from the platform. At each of the four cardinal directions, a symbol, such as a plus or a cross, was placed as possible recognition flags. For three consecutive days, two times each day, mice were dropped off facing the wall at four different drop zones (four trials each in the morning and the afternoon). Each trial was performed by alternating two mice (A1, A2, A1, A2, A1, A2 . . . etc). Latency was measured as the time that it took for the mouse to find and spend 1 second on the hidden platform. If there was a failure to reach the platform in 60 seconds, the mouse was guided to the platform and allowed to rest on it for 15 seconds. On the fourth day, a probe trial was performed, in which the platform was removed and mice was allowed to swim in the pool for 60 seconds.

Then in the subsequent trials (reverse learning and probe trials), the order in which the mice were placed in the pool was reversed, and the swim procedure was repeated with the hidden platform relocated diagonally from the initial platform location, and the drop zones were also altered to be directly diagonal from the forward swim drop zones.

After reverse learning and probe trials, a flag was placed atop of the hidden platform and mice were repeatedly placed in the pool. Time taken to reach the visible platform was recorded. When a consistent time for a mouse was reached, the last three times were averaged and the overall average of latency to hidden platform was used to exclude mice that were outliers from analysis due to visual impairments. Latencies and distance traveled for all trials were measured with the Panlab SMART Video Tracking Software.

Passive Avoidance Test

A Passive Avoidance Controller CAT 7551 was used to conduct the passive avoidance test as previously described (Gimbel et al., 2010, J Neurosci 30:6367-6374) with slight modifications. The door delay was set to 90 seconds, and the shock intensity was set to 0.5 mA with a shock duration of 2 seconds. A mouse was placed into the white box with a light source overhead and given 5 minutes to cross through the door and into the opaque, black box after 90 seconds of acquisition in the white box. In trial 1, the mouse received a foot shock once it passed through to the black box. For trial 2, the mouse was placed back in the white box approximately 5 minutes after trial 1 and was shocked if it passed through to the black box. Twenty-four hours after trial 1, trial 3 was conducted with the shock intensity lowered to 0.0 mA. Experimenter was blinded to the genotype of the mouse.

Rotarod Performance Test

The Rotarod test was performed as previously described (Zou et al., 2015, J Neurosci 35:10429-10439). Mice were placed atop a Rotarod (Economex Columbus Instruments) that was set to accelerate at 0.3 rpm/s until 4 rpm. Five trials were performed on each mouse with two-minute rests in between each trial. The time that each mouse stayed on the rod was recorded. Experimenter was blinded to the genotype of the mouse.

Multiple Mild TBI Studies

The injury model was based on the combination of Closed Head Injury (CHI) and Chronic Variable Stress (CVS). The Sham mice received Sham-CHI and Sham-CVS treatments.

Closed Head Injury

Closed Head Injury (CHI) is a well-established mice injury model (Sangobowale et al, 2018, Neurotrauma 35:907-917). Mice were weighed prior to receiving Sham-CHI or CHI. Isoflurane-based anesthesia was induced for 3 minutes with isoflurane (3.5% in oxygen (1.0 L/min) and maintained (3% in oxygen (1.0 L/min) until immediately after the impact. The head of the mouse was shaved and CHI was induced using a 5.0 mm diameter tip operated by an electromagnetic impactor (Leica Microsystems, Buffalo Grove, Ill.). The 5 mm diameter impactor tip was placed 5 mm lateral from the midline and 5 mm caudal from the eyes with preset impact velocity 5 m/sec, impact depth of 1 mm and 1 s dwell time. Sham-CHI mice were shaved and anesthetized in the same manner, but did not undergo impaction. The total anesthesia exposure during each procedure did not exceed 6 minutes. Mice were placed on a heating pad to maintain body temperature while receiving the impact, as well as during the post-injury recovery period. The mice underwent a total of 14 consecutive days of CHI injury, once per day. The site of injury alternated between right and left hemispheres on consecutive days. Each CHI injury was performed 1-3 hours after that day's CVS exposure. Injury severity was assessed using time interval between injury and recovery of the righting reflex (Grin'kina et al., 2013, PLoS One 8, e53775). The mice were placed on a heat pad both while receiving the impact, as well as the period following the impact to preserve their core body temperature. Mice were returned to vivarium after restoration of their righting reflex and this was typically less than 5 minutes.

Chronic Variable Stress

Stress was induced using the chronic variable stress (CVS) model (Ostrander et al., 2006, Endocrinology 147: 2008-2017). The CVS was comprised of exposure to 5 different aversive stimuli over a 14 day period. The stimuli included: 3-minute cold water swim at 16-18° C., overnight food deprivation with access to water ad libitum, three hours in a cage with 300 ml of water added, three hour exposure to a cage tilted at 45 degrees, and 15 minutes immobilization in a flat-bottomed restraint chamber (Braintree Scientific Instruments). The mice were exposed to a set of two pre-randomized aversive stimuli on each given day during the 14 day period, in order to simulate the unpredictable nature of psychological trauma, while limiting habituation.

Schedule for TBI Treatment with AZD0530

In the first treatment experiment, mice began treatment on Day 15 (24 hours following the last injury on Day 14) with AZD0530 at 5 mg/kg/day in two equally divided doses by oral gavage for a 10 week period as described (Zou et al., 2015, J Neurosci 35:10429-10439). The Vehicle for the drug was 0.5% wt/vol hydroxypropyl-methylcellulose (HPMC)/0.1% wt/vol polysorbate 80, and each dosing volume was 250 µl.

In the second treatment experiment, the mice underwent a 10 week treatment starting on Day 121, or 107 days after the last day of injury.

Upon completion of the treatment period, both groups underwent a weeklong period of behavioral assays including Morris Water Maze (MWM), and novel object recognition, as described (Kaufman et al., 2015, Ann Neurol 77:953-971). Each mouse was handled for 5 minutes for the 5 days preceding the behavioral testing. The mice received the continued oral gavage treatment during the testing period.

Quantification and Statistical Analysis

One-way ANOVA with Dunnett's multiple comparisons test, two-way ANOVA with Sidak's multiple comparisons test, t-test, or Wilcoxon match-pairs signed tests were performed as specified in the figure legends using GraphPad Prism 8. All n-values represent individual mice. For IHC, each data point represents the average of three brain sections from one animal. For behavioral tests, the number of trials that each data point represents can be found in the figure legends. Values are represented as mean±SEM. Statistical significance is determined if $p<0.05$.

Example 1: Pharmacological Inhibition of Fyn Kinase Inhibits Progression of AD

The studies presented herein were conducted to examine whether the pharmacological inhibition of Fyn kinase slows or halts the progression of AD.

Fyn Activation by Aβo-PrP$^C$ Alters Synaptic Function

Activation of Src family kinases (SFK) may be monitored by phosphospecific epitopes. Cultures were examined for SFK activation after exposure to Aβo (FIG. 1A). Wild type cortical neurons increased pY416-Fyn (SFK) in response to Aβo. The antibody used detects pY416 in several SFKs, but PrP$^C$-dependent activation is Fyn-specific. In Prnp−/− cultures, activation of Fyn by Aβo was eliminated. It was also assessed whether these assemblies also activate neuronal Fyn. AD brain extracts at 6 µg protein/ml stimulated Fyn activation in mouse cortical cultures, but control brain extracts did not. Thus, TBS-soluble Aβ derived from human AD stimulates neuronal Fyn via PrP$^C$.

Figure 1B:
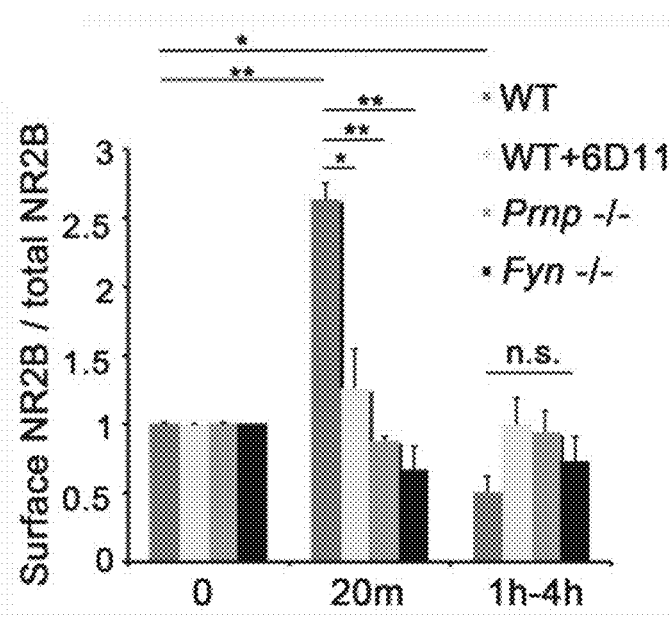

NMDA-Rs play a key role in synaptic plasticity and AD. Intracellular segments of NR2A and NR2B subunits contain tyrosine residues phosphorylated by SFKs. Thus, Aβo/PrP$^C$-mediated Fyn activation may be directed to NMDA-R. Aβo induced a dose-dependent increase in the phosphorylation of NMDA-R, specifically the Fyn-specific phosphorylation of NR2B at Y-1472 (FIG. 1B). Aβo-induced NR2B phosphorylation was eliminated in Prnp−/− cultures, in Fyn−/− cultures, and by 6D11 anti-PrP$^C$ antibody. Moreover, the roles of PrP$^C$ and Fyn are gene-dose-dependent, being reduced in heterozygous neurons. The effect was biphasic, such that NR2B phosphorylation was enhanced during the first 15 minutes with Aβo, but phosphorylation was suppressed after 1-3 hours (FIG. 1B).

Figure 1C:
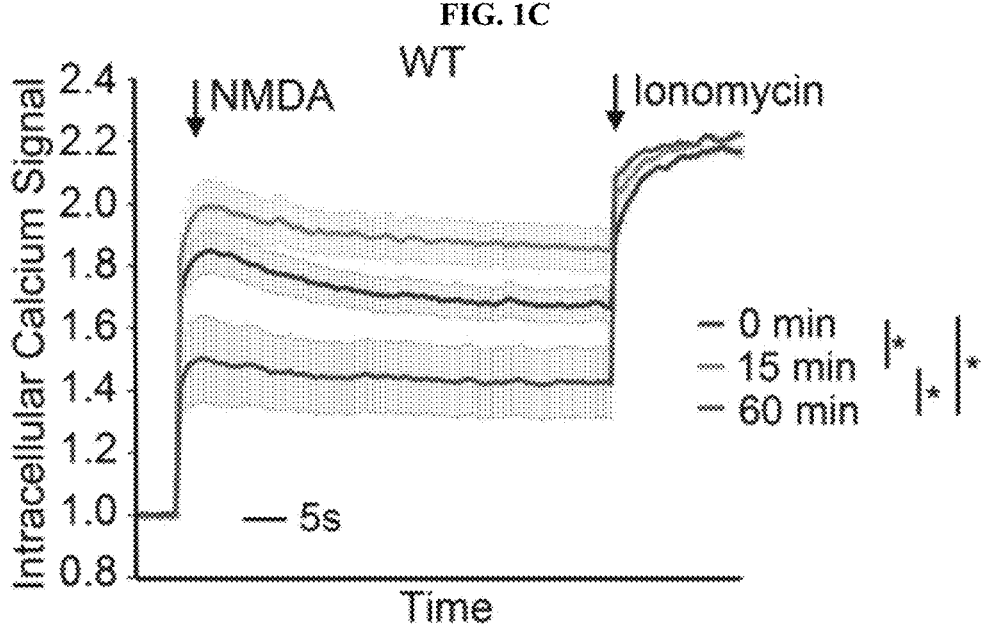

Phosphorylation of NR2B at Y1472 i reduce AP-2 mediated endocytosis. The extent to which NR2B is accessible at the cell surface versus being sequestered intracellularly was examined. In concert with the NR2B-pY-1472 increase, surface NR2B increased shortly after Aβo exposure. A calcium-sensitive fluorescent dye was utilized to monitor intracellular calcium in cortical neurons. NMDA produced increased fluorescence signal (FIG. 1C). Pretreatment with Aβo for 15 minutes generated significantly increased NMDA-induced signal. By 60 minutes, when NR2B receptors were dephosphorylated and internalized, NMDA-induced calcium signals were suppressed. One hour pretreatment with Aβo suppresses glutamate responses in WT, but not in Prnp−/− or Fyn−/− neurons. Thus, Aβo-induced, PrP$^C$-mediated alterations in NMDA-R created transient increases and then decreases in neuronal calcium.

Figure 1D:
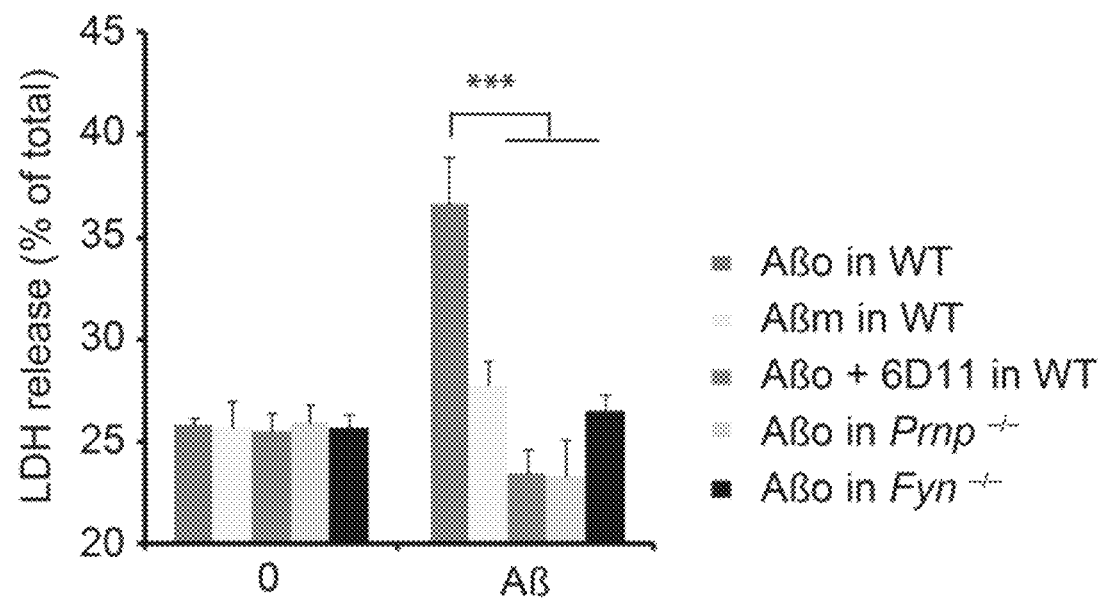

It was investigated whether the transient increase in surface NR2B leads to a brief period of excitotoxicity. Brief exposure to Aβo reduced cell viability, with a release of 10% of cellular LDH (FIG. 1D). Genetic deletion of either Fyn or PrP$^C$ expression rescued neurons from A3o (FIG. 1D). Heterozygosity for null alleles of Prnp or Fyn significantly reduced LDH release. Thus, Aβo requires PrP$^C$ to induce Fyn activation and subsequent NR2B phosphorylation. This phosphorylation is associated with transient increase in NR2B at the cell surface with consequent excitotoxicity.

Figure 1E:
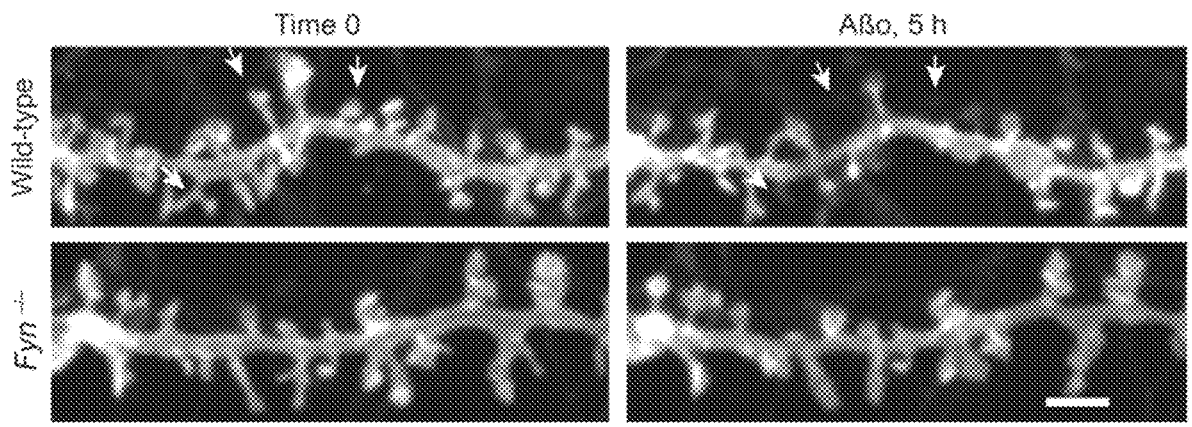
Figure 1F:
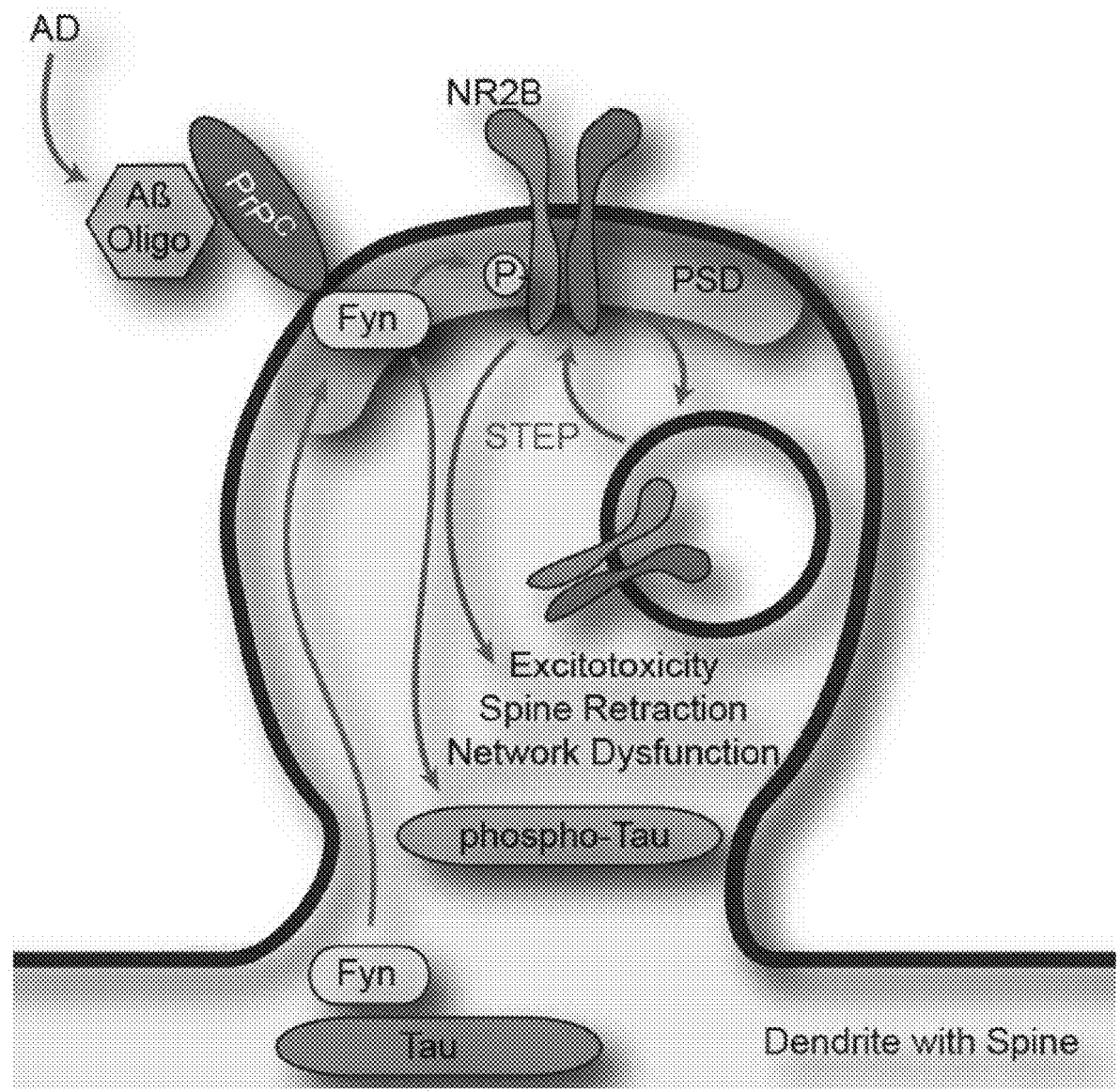

A hallmark of AD is synaptic loss, and dendritic spine loss may occur after acute A3o exposure. To assess the roles of PrP<sup>C</sup> and Fyn in Aβo-induced spine loss, neurons were cultured from embryos homozygous for null alleles (FIG. 1E). Spine destabilization by Aβo was eliminated in Prnp−/− and Fyn−/− neurons. These studies demonstrate that Fyn plays a central role in coupling Aβo and PrP<sup>C</sup> to changes in neuronal function (FIG. 1F). When Fyn mutants were crossed with APP transgenic mice, Fyn gain-of-function enhanced AD-related phenotypes while Fyn loss-of-function ameliorated AD-related phenotypes.

Saracatinib Inhibits Fyn

Saracatinib (AZD0530) is an inhibitor of Src Family kinases (SFKs), blocking Src, Fyn, Yes and Lyn, with 2-10 nM potency (Hennequin et al., 2006, J Med Chem 49:6465-4688).

Saracatinib's specific inhibition of Fyn and SFKs have led to its development as therapy for solid tumors, because Src family kinases regulate tumor cell adhesion, migration and invasion, and also regulate proliferation (Hennequin et al., 2006, J Med Chem, 49: 6465-4688). Clinical tolerability and oral bioavailablity have been demonstrated, but Phase II studies have demonstrated limited benefit as a single agent in specific oncological indications (Gangadhar et al., 2012, Invest New Drugs; Gucalp et al., 2011, Clinical Breast Cancer, 11: 306-311; Mackay et al., 2012, Invest New Drugs, 30: 1158-1163; Fury et al., 2011, Anticancer Res, 31: 249-253; Renouf et al., 2012, Invest New Drugs, 30: 779-786). For tumor cell migration and for oncological applications, it is estimated that >98% kinase inhibition is required so clinical doses have targeted concentrations >20-fold above the kinase $IC_{50}$, in the 200-1000 nM concentration. Importantly, CNS preclinical effects, and therefore AD dosing, are achieved with much lower concentrations in the 5-50 nM range with 50-95% target inhibition.

Figure 2A:
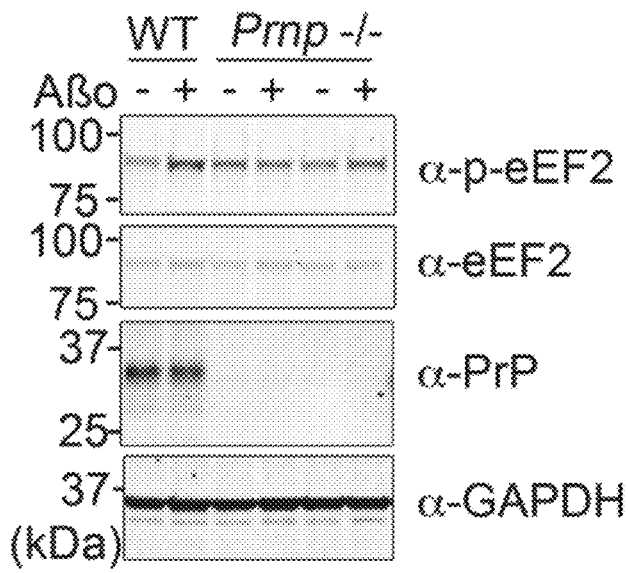
FIGS. 2A-2D illustrate the results of experiments demonstrating that saracatinib inhibits Fyn and Aβo-induced signaling in neurons.

Saracatinib Prevents Fyn Activation and Downstream Signaling by A/o in Cortical Neurons The efficacy of saracatinib in reversing Aβo-induced Fyn kinase pathways in neurons was assessed. In addition to monitoring pY416 activated Fyn itself, a readily detected downstream marker of saracatinib's capacity to abrogate the chronic effect of Aβo in reducing dendritic spine density was sought. Because spine turnover is dependent on protein translation machinery, and because both Aβo and Fyn have been linked to mGluR5, a downstream effector of mGluR5-regulated protein translation, the eukaryotic elongation factor 2 (eEF2), was considered. The eEF2 pathway is regulated by phosphorylation and is dysregulated in AD. A3o treatment of cortical neurons increases eEF2 phosphorylation at 5 min (FIG. 2A). Genetic analysis confirmed that the Aβo effect on eEF2 phosphorylation depends on PrP<sup>C</sup> (FIG. 2A).

Figure 2B:
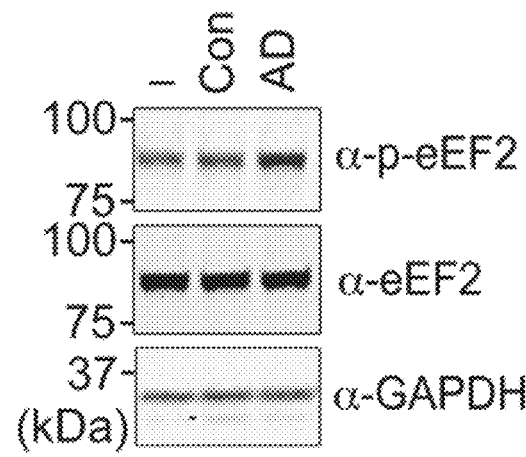

To extend the AD relevance of these observations with synthetic Aβo effects, it was tested whether human AD extracts generated similar eEF2 phosphorylation. Pooled TBS-soluble extracts from AD brain, but not control brain, elevated the phosphorylation of eEF2 in WT mouse 21 DIV neurons (FIG. 2B).

Figure 2C:
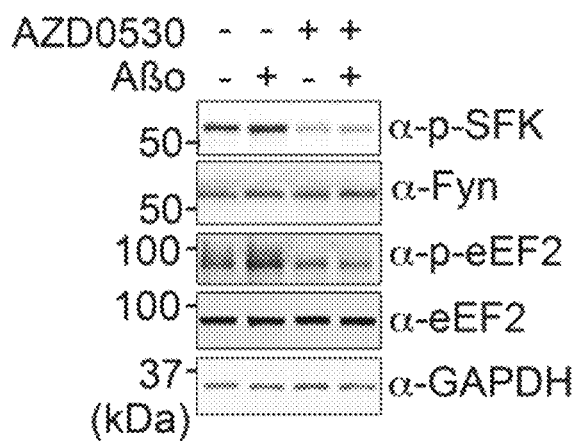
Figure 2D:
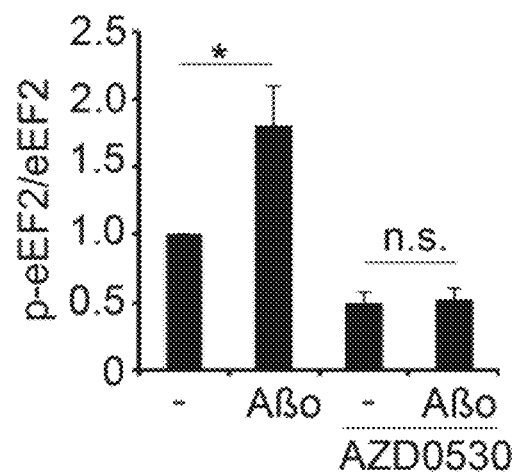

It was assessed whether the SFK inhibitor saracatinib disrupts these biochemical actions of Aβo in cortical neurons. Saracatinib suppressed basal p-SFK levels and fully prevented A3o stimulation of its target kinase (FIG. 2C). It was tested whether phosphorylation of eEF2 induced by Aβo depends on AZD0530-sensitive Fyn kinase activation. Downstream signaling from Aβo to increase eEF2 phosphorylation was fully blocked by AZD0530 treatment (FIG. 2C). Thus, AZD0530 prevented Aβo/PrP-induced, Fyn-dependent neuronal signaling in vitro.

Blocking Fyn Kinase Activity with Saracatinib Prevent AD Progression

The focus on Fyn inhibition is highly innovative in the AD field. There have been no successful clinical efforts focused on targeting Tau and Tau kinases in AD, with none providing a unified approach to Aβ and Tau. Fyn is unique as an AD target, in being central to Aβ signal transduction and having major functional interactions with Tau as well. Thus, the target is innovative in addressing toxicity related to both hallmarks of AD pathology.

The data presented herein demonstrates that AZD05030 blocks Fyn kinase activation and is a disease-modifying therapy for AD. In certain embodiments, an AD-modifying therapeutic revolutionizes the care of millions of US citizens with a major impact on health care costs. Today, there is no existing disease-modifying therapy for mild AD or amnestic MCI.

Example 2: Effect of a Fyn Inhibitor on Alzheimer's Disease Pathophysiology

To test the ability of saracatinib to treat learning and memory deficits caused by AD pathophysiology, WT and APPswe/PS1ΔE9 transgenic mice were treated with a Fyn inhibitor (saracatinib). The treatment was started when mice were 11-12 months of age. At this age, the transgenic mice generally have a pronounced learning and memory deficit. The dosing was on a twice a day schedule by oral gavage and control groups received vehicle. The identity of the active versus vehicle groups and the transgene status was unknown to the researchers handling the mice and collecting the behavioral data. Mice were treated with 0, 2 or 5 mg/kg/d of saracatinib. Both 2 and 5 mg/kg/d doses were tested against vehicle in a first cohort and then (because the initial results suggested that 5 mg/kg/d was required for benefit) a second cohort of mice was tested with 0 versus 5 mg/kg/d. The data from the two cohorts were pooled. Different tests were performed at 1-3 weeks (early) or 4-6 weeks (late) time points. Mice were tested in the Morris water maze at both ages, and also in Novel Object Recognition tests at the later time points. After memory testing was complete, the animals were sacrificed without ceasing their drug regimen for histological analysis.

Figure 3:
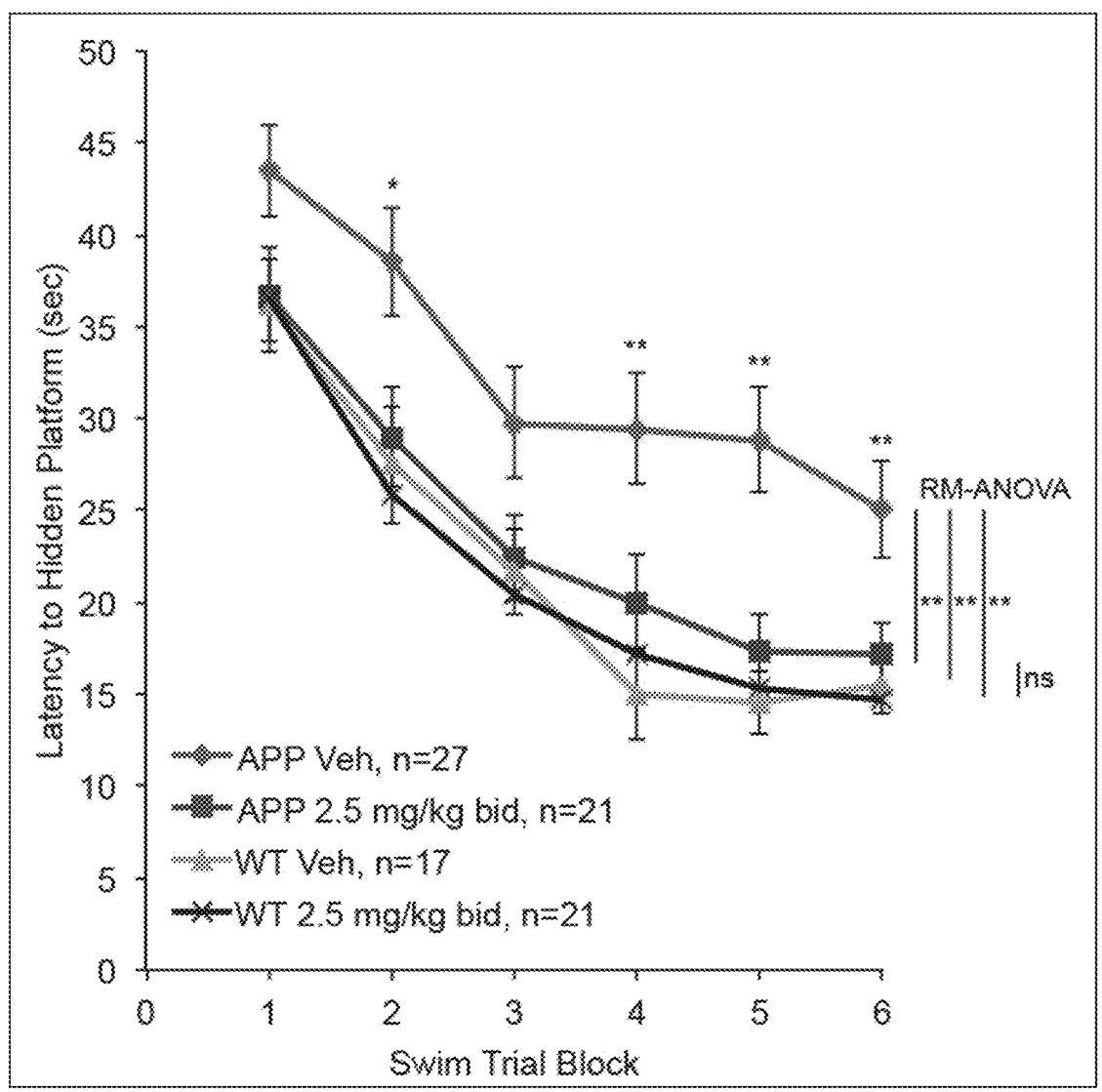
FIG. 3 is a graph illustrating the finding that saracatinib improves learning in transgenic AD mice. Spatial learning is plotted as latency to find a hidden platform in a Morris water maze at age 11-12 months. Mice were treated b.i.d. by oral gavage for 3-4 weeks prior to the start of testing with 0 or 5 mg/kg/d saracatinib and treatment was continued through the testing period. Mean±SEM for the indicated numbers of mice per genotype/treatment group. By Repeated Measures ANOVA with Tukey post-hoc pairwise comparisons across trial blocks 3-6, the vehicle-treated APPswe/PS1ΔE9 group differed from each of the other groups (P<0.001), whereas none of the other groups differed from each other (p>0.05). For specific trial blocks, the vehicle-treated APPswe/PS1ΔE9 group differed from each of the other groups,  P<0.005 or * P<0.05, whereas none of the other groups differed from each other (P>0.05).

The results of the pooled Morris water maze data for wild type and transgenic mice treated for 4-5 weeks with vehicle or 5 mg/kg/d saracatinib are shown in FIG. 3. The learning trials showed that wild type mice have progressively shortened latencies to a hidden platform, and this is not altered by treatment with 5 mg/kg/d saracatinib. The transgenic mice were impaired and did not show as much learning, with significantly prolonged latencies on the later blocks of swim trials. Treatment with saracatinib for 4-5 weeks eliminated the transgenic deficit, fully normalizing latencies to the hidden platform on trial blocks 4-6.

Figure 4:
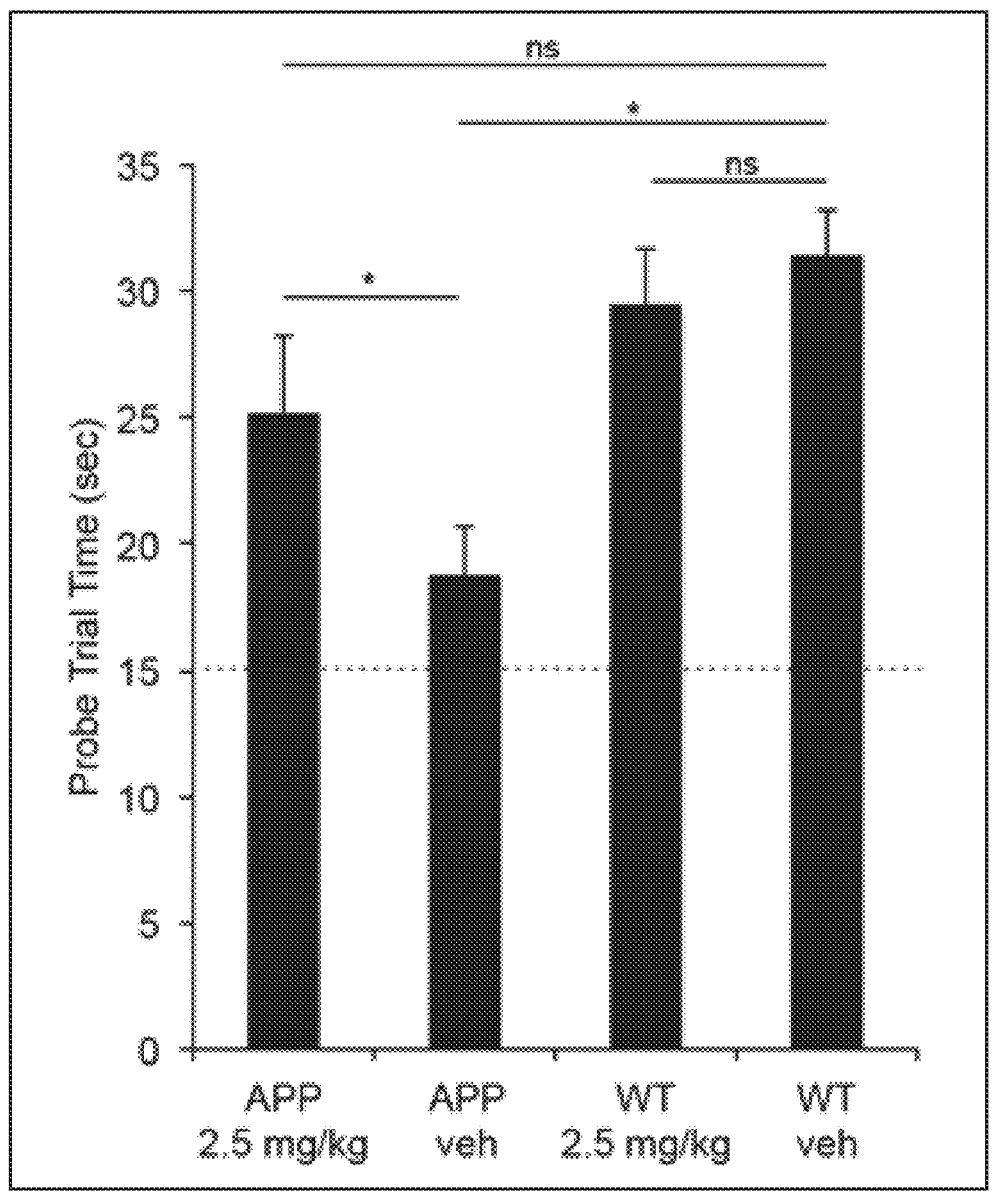
FIG. 4 is a bar graph illustrating the finding that saracatinib improves memory in transgenic AD mice. Memory performance during a 60 sec probe trial, 24 hr after learning, where time spent in the target quadrant was measured. Random chance is 15 sec. Mean±SEM for n=9-14 in each group. Target quadrant time differed by one-way ANOVA with post hoc LSD pairwise correction for the indicated comparisons (*, P<0.05).

After the learning trials, the mice were tested the subsequent day in a memory test, the 60 second probe trial with the hidden platform removed (FIG. 4). Random chance results in 15 sec occupancy in each quadrant. The wild type mice with or without 5 weeks saracatinib treatment preferred the target quadrant, with typical times of 30 seconds compared to an average of 10 sec in each of the non-target quadrants. In contrast, the APPswe/PS1ΔE9 mice treated with vehicle control spent much less time in the target quadrant, performing close to the chance level of 15 seconds. The 5 mg/kg/d-saracatinib treated group showed the same strong preference for the target quadrant as did WT mice. Thus, this dose of saracatinib fully rescued both learning and memory deficits in aged AD transgenic mice.

Shorter treatment duration or lesser doses did not have significant effects in these tests.

Figure 5:
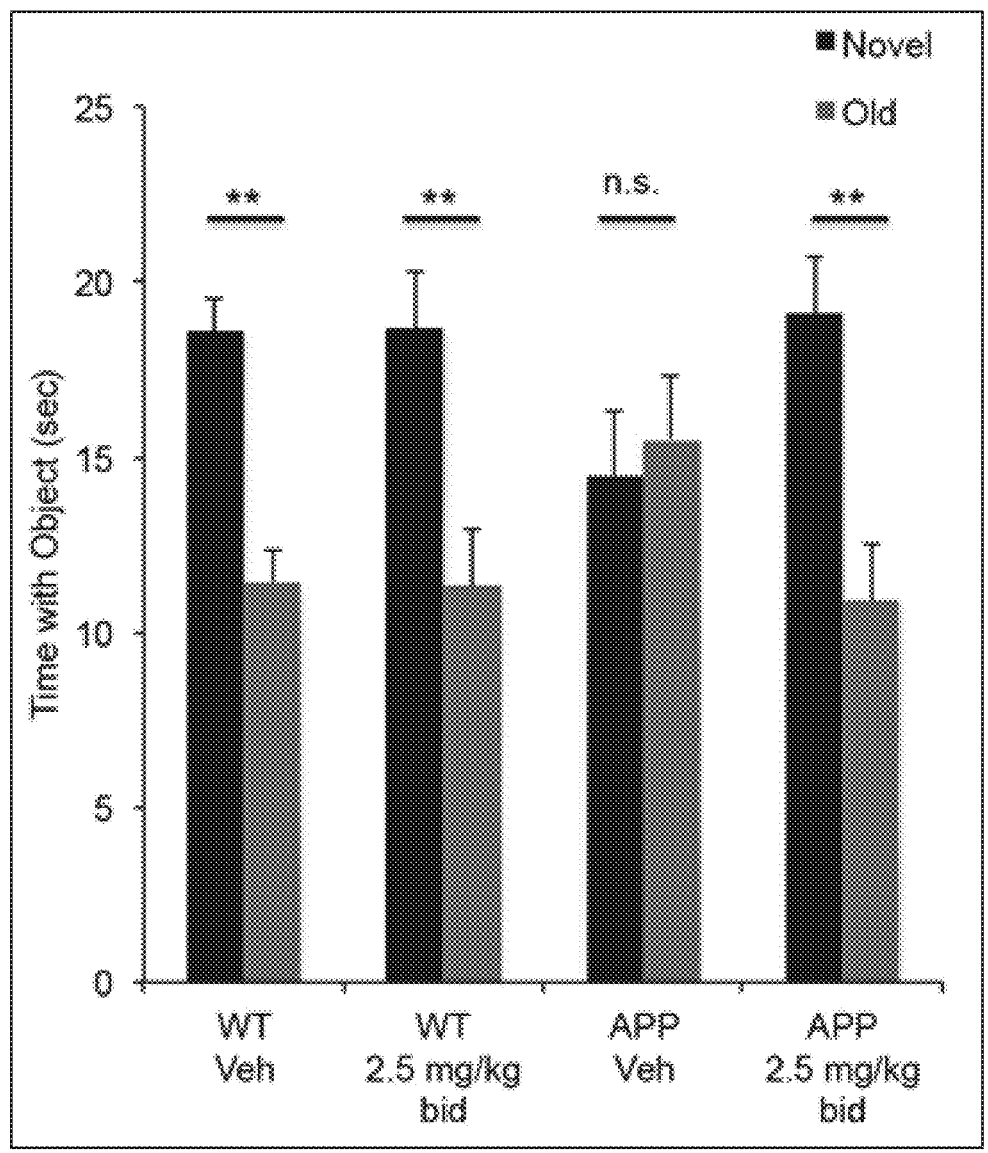
FIG. 5 is a bar graph illustrating the finding that saracatinib improves novel object recognition in transgenic AD mice. The time spent exploring a novel object was greater than a familiar object for the indicated cohorts (**, P<0.005, Student's t test) or was not significantly different as indicated (n.s., P>0.05). Mean±SEM for n=9-14 in each group.

As an independent test for memory, the same cohort was tested after 5 weeks of saracatinib or vehicle treatment for performance in Novel Object Recognition. The animals were familiarized with two objects on the first day of testing, and then observed on the next day with one novel object and one familiar object. The time spent exploring each object was scored by an observed unaware of drug treatment (FIG. 5). WT mice spend more time with the novel object. However, vehicle-treated APPswe/PS1ΔE9 mice spent equal time with both objects, consistent with impaired memory of familiarization on the previous day. The saracatinib treated transgenic mice exhibited performance equal to the WT mice. The tissue from these mice is analyzed histologically, e.g., for Aβ plaque and synaptic markers (which are reduced in the transgenic mice). No significant changes in Aβ plaque content was caused by saracatinib. Without wishing to be limited by theory, this finding is consistent with the fact that saracatinib blocks the downstream action of Aβo on neurons, but not the upstream production of Aβ.

Figure 10A:
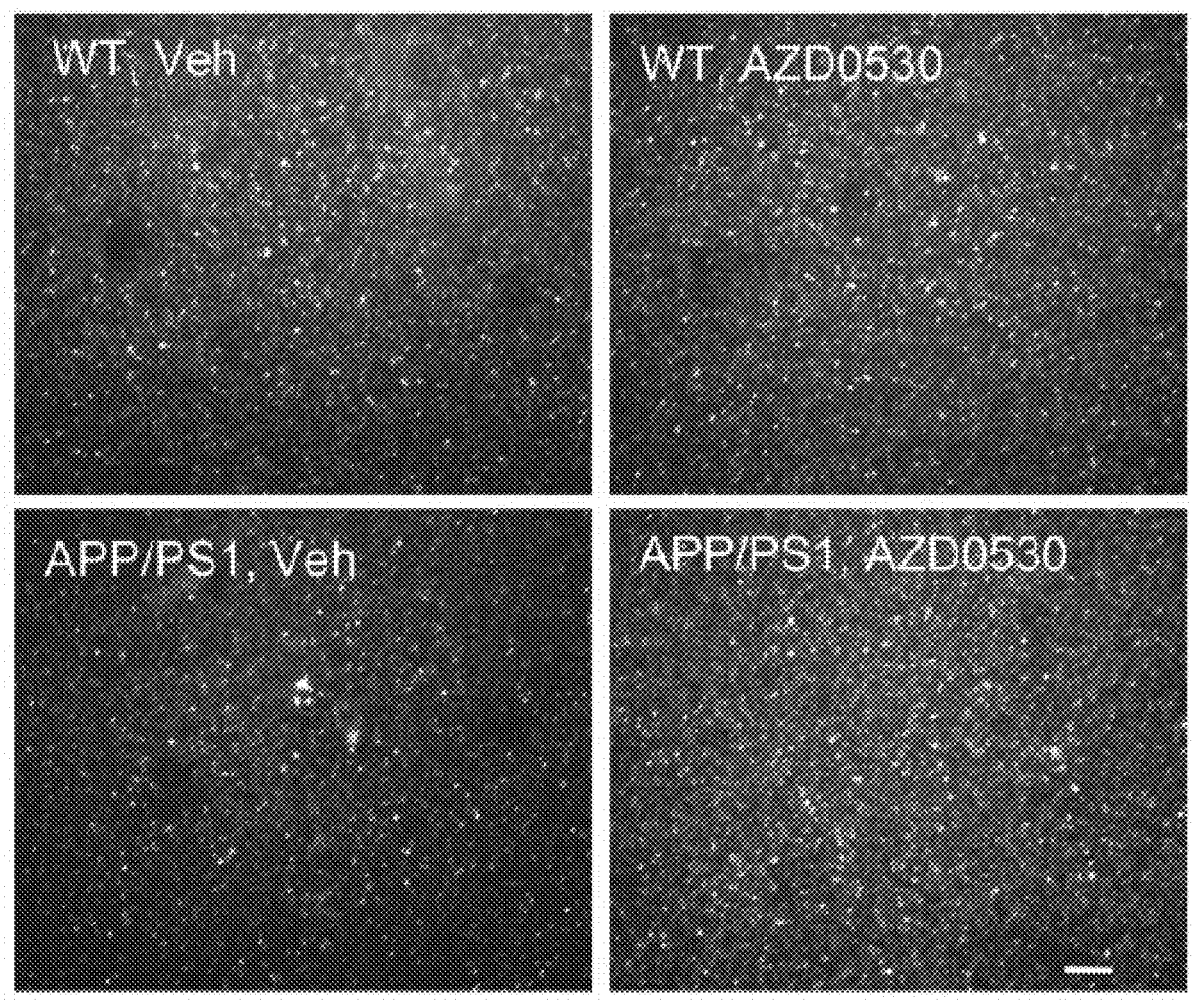
FIGS. 10A-10C illustrate the finding that synaptic markers recover after treatment with a Fyn inhibitor. WT and APP/PS1 mice that were aged to 13 months were treated with 2.5 mg/kg of saracatinib or vehicle by oral gavage twice a day for 6 weeks, and were then sacrificed for histological analysis.
Figure 10B:
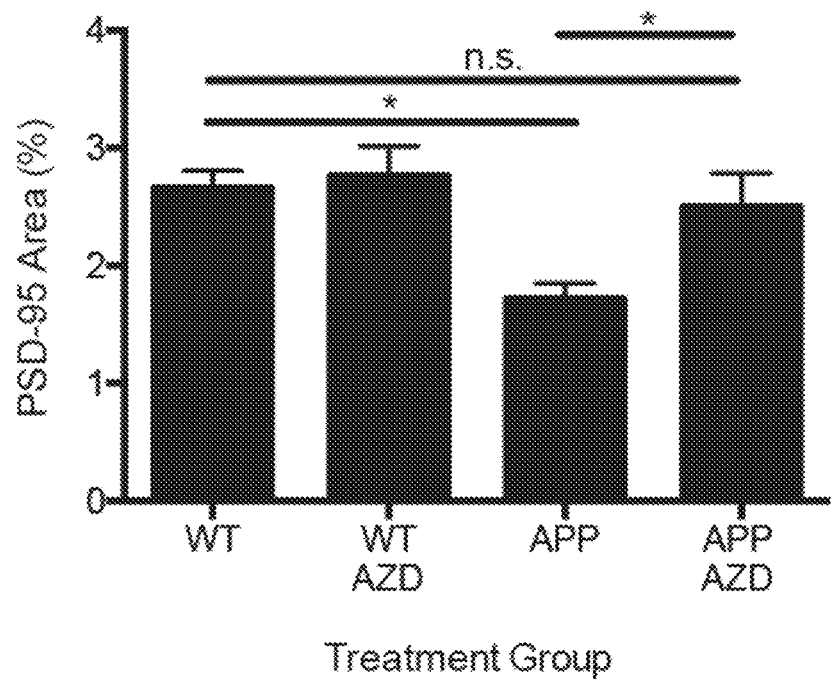
Figure 10C:
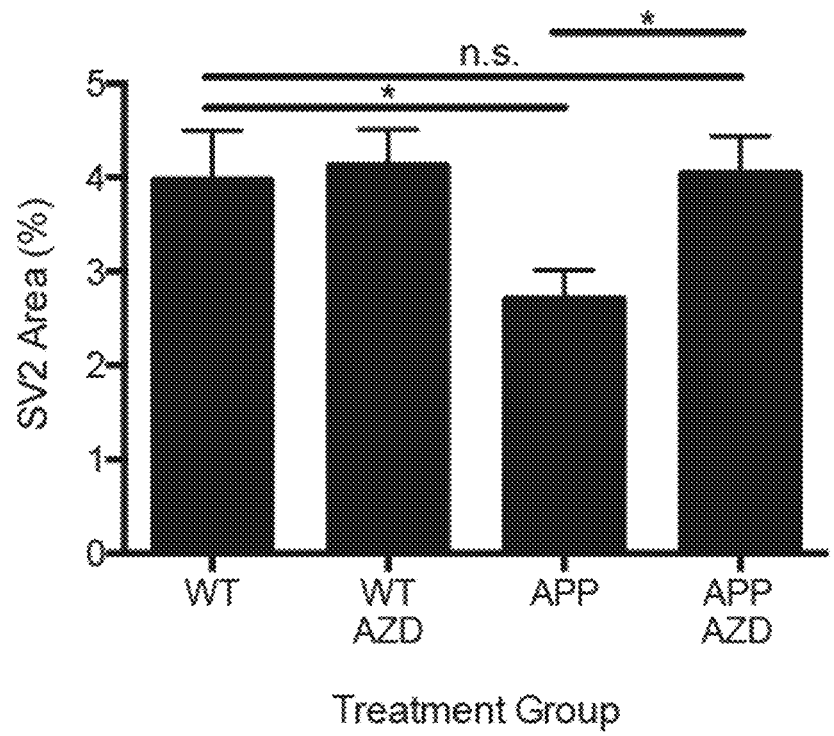

Upon analysis of a post-synaptic marker (PSD-95) or a presynaptic marker (SV2A) in the dentate gyrus of the hippocampus, an saracatinib-induced restoration of synapse density was observed. The twelve-month old transgenic mice have lost approximately 30-40% of synapses by the immunohistological measures. After 5 weeks of saracatinib, there was no change in synapse density for WT mice, but the decreased synapse density for APPswe/PS1ΔE9 mice was restored to WT control levels (FIGS. 10A-10C). Taken together, the data reported herein demonstrate saracatinib efficacy in the mice.

Figure 6:
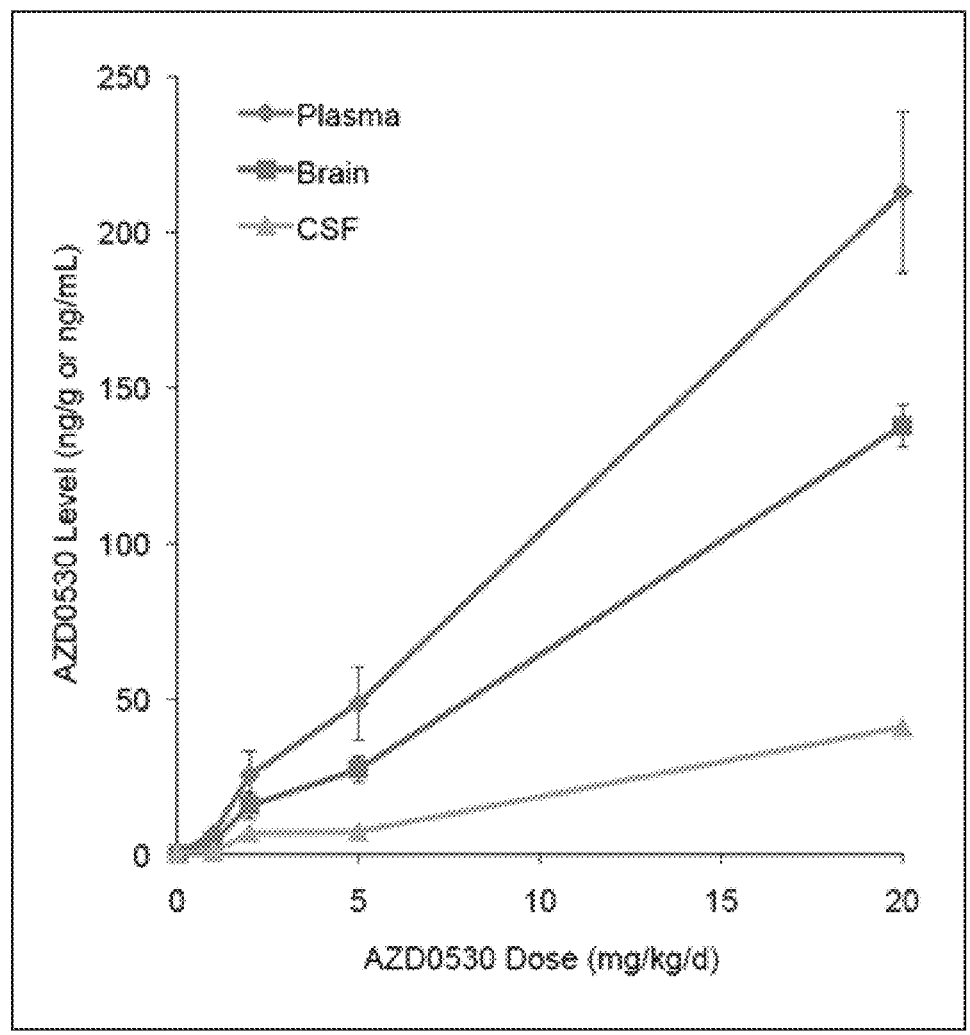
FIG. 6 is a graph illustrating saracatinib drug levels in mice with multiple doses. Mice were treated with the indicated levels of saracatinib by oral gavage for 6 b.i.d. doses and then brain, plasma and CSF were collected for assay. Data are mean±sem for separate mice for all points except CSF where samples pooled.

Saracatinib drug levels were analyzed after mice were dosed with 0, 1, 2, 5 or 20 mg/kg/d saracatinib in b.i.d. oral doses. At the time of the study, no data were available relating to mouse CNS saracatinib level, or CSF levels in any species. In an initial cohort after 6 doses, samples were collected 30-60 minutes after dosing to obtain a peak level (FIG. 6). Drug levels were measured with an LC/MS/MS method validated for clinical samples. The brain level was at least 50% of plasma levels in mouse. The CSF level was measurable, and about ⅓ of brain level. From this analysis, the peak brain level at the dose which was effective for improving memory (5 mg/kg/d) averaged 27 ng/g saracatinib free base or 50 nM. The peak CSF level at 5 mg/kg/d from one pooled sample was 7 ng/ml saracatinib free base or 13 nM.

Because human CSF was measured at trough and the half-life in mouse may be short, trough brain saracatinib levels was measured in another cohort of mice at 5 mg/kg/d and a range from 10 ng/g to 25 ng/g (19-46 nM) was observed. The trough CSF level at 5 mg/kg/d from one pooled mouse sample was 4.6 ng/ml saracatinib free base or 8.9 nM. The calculated trough CSF range calculated from multiple brain samples was 3.1 ng/ml to 7.6 ng/ml (5.8-14 nM). Given that the $K_i$ of saracatinib for Fyn kinase is 5 nM, these data show that oral delivery at doses which improve transgenic mouse memory function (FIGS. 3-5) yields levels expected to inhibit at least 50% of Fyn kinase activity in brain.

Figure 7:
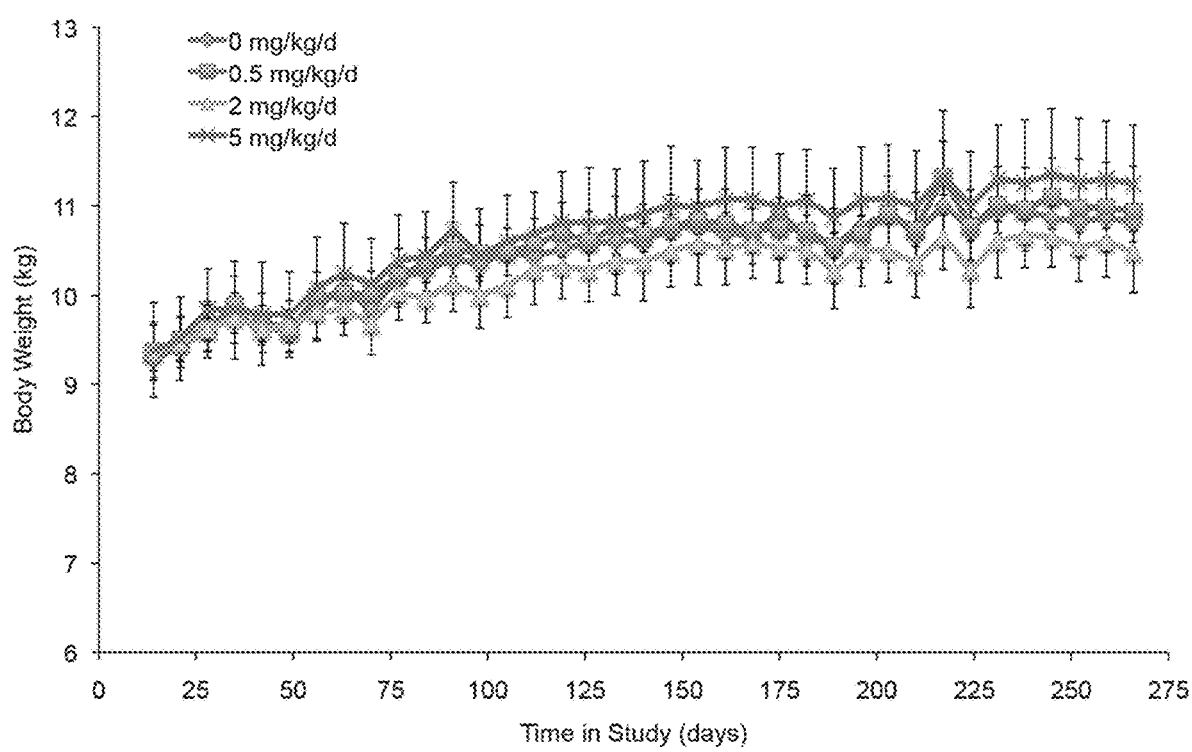
FIG. 7 is a graph illustrating body weight of dogs treated chronically with saracatinib. The body weight of dogs treated with different doses of saracatinib was plotted as a function of time. There were a total of 8 dogs (4 female and 4 male in each group), but a single sex (male) is shown here because the weight range is different between sexes. The trend for female dogs is similar but not shown. Values are mean±sem.

The $C_{max}$ and AUC values for dosing in dog at 5 mg/kg produces exposure equivalent to 125 mg saracatinib free base in human, and the exposure in dogs with multiple dosing is linear from 0.5 to 5 mg/kg oral daily dose. A nine-month dog toxicology study (8 dogs per dose) at 0 mg/kg/d, 0.5 mg/kg/d (NOAEL in 6 month), 2 mg/kg/d (equivalent to 50 mg daily in humans) and 5 mg/kg/d (a dose with mild GI toxicity in the 6 month study and equivalent to 125 mg daily in humans) was performed. There were no obvious adverse symptoms at 8.75 months, and the continued weight gain of dogs receiving the saracatinib (FIG. 7) suggests that there are no unexpected safety concerns with chronic use.

Example 3: Clinical Studies

A Phase Ib multiple ascending dose study of saracatinib was completed using 24 subjects with mild to moderate AD. Subjects were enrolled in three cohorts of 8 subjects each. Each cohort consisted of subjects receiving saracatinib (n=6) or placebo (n=2) PO daily. Daily, the first cohort received 50 mg saracatinib free base (71.4 mg saracatinib difumarate), the second 100 mg (142.9 mg saracatinib difumarate) and the third 125 mg (178.6 mg saracatinib difumarate).

There were no apparent study-related serious adverse events (SAEs), significant laboratory abnormalities, or early terminations. In particular, there were no significant hematological changes.

Figure 8:
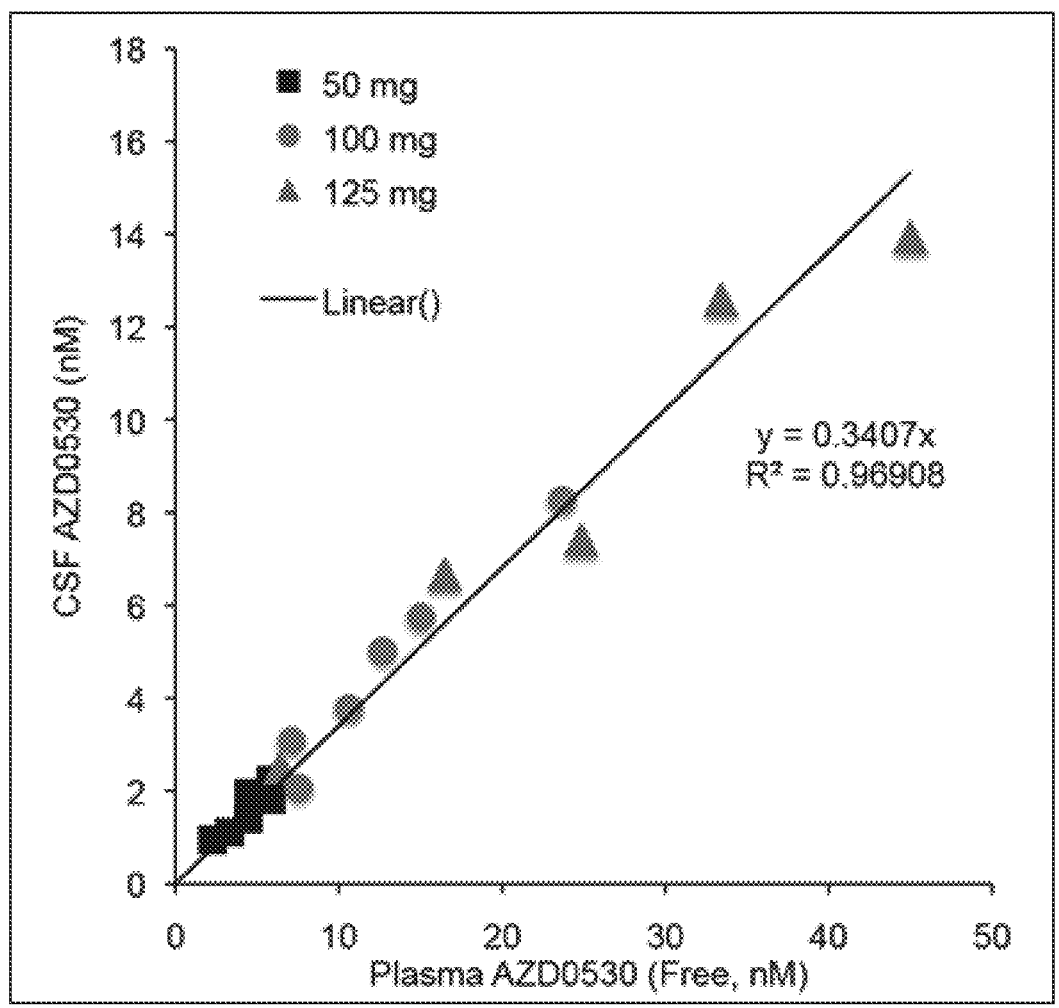
FIG. 8 is a graph illustrating results obtained for saracatinib in a human phase 1b trial. Each point is from a different individual. The different dose groups are illustrated with different colors. There was a tight correlation of plasma and CSF level as indicated: the CSF level was found to be about 0.3407 times the concentration of free saracatinib in plasma.

Beyond safety and tolerability, the Phase 1b collected both CSF and plasma for saracatinib levels, and obtained FDG-PET scans at the start and end of the treatment period. In certain embodiments, obtaining the scans worked as a pilot to the collection of brain metabolism data for the Phase 2a trial. In addition, saracatinib levels were measured in this study using a GLP-validated LC/MS/MS assay. There was a close correlation between free saracatinib in plasma and CSF saracatinib (FIG. 8). CSF levels are about a third of plasma free drug levels.

Figure 9:
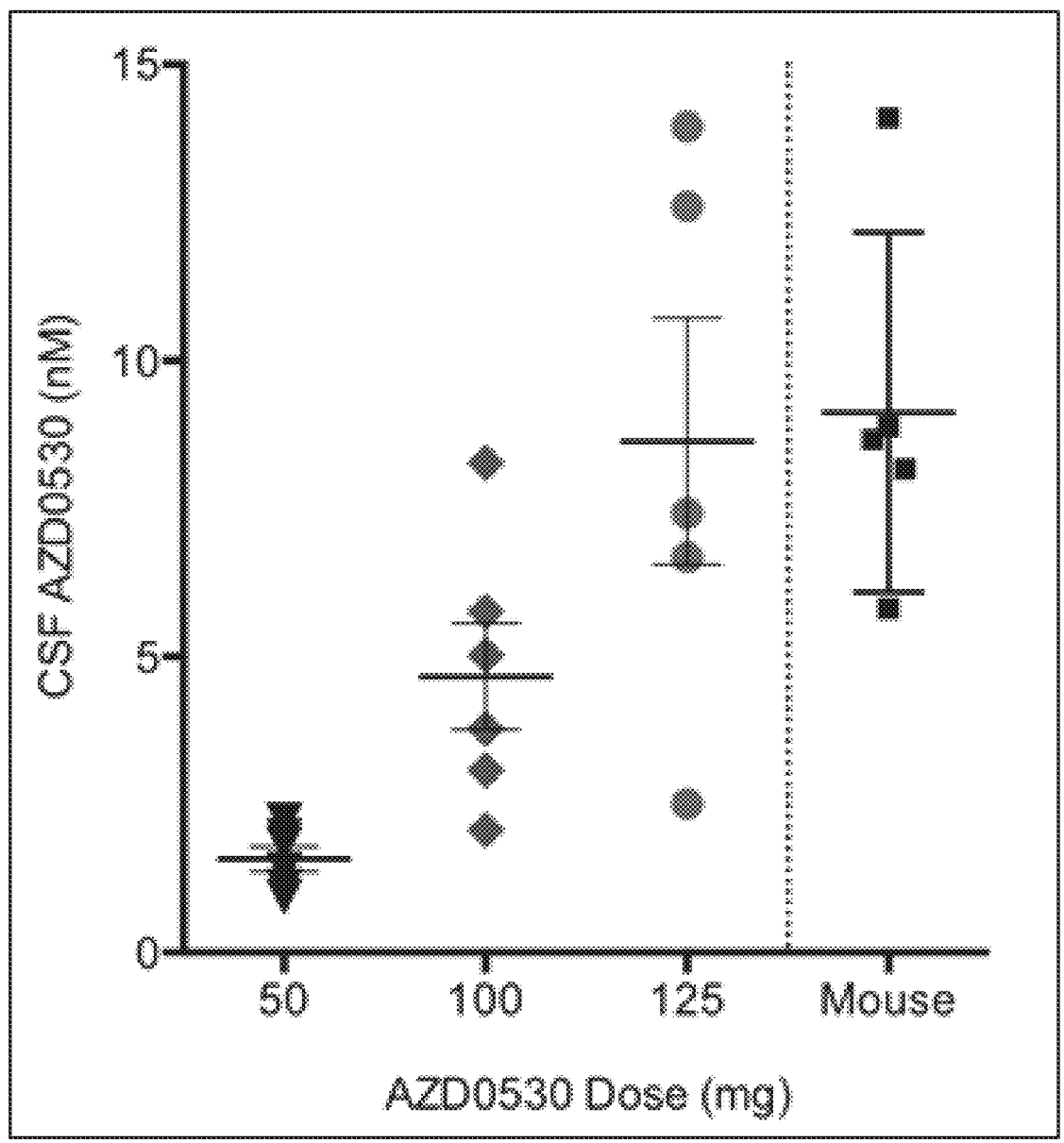
FIG. 9 is a graph illustrating the measured values of saracatinib in human CSF at various doses. Each point represents trough CSF saracatinib level from a different human subject for the left three columns. The mouse trough CSF values are derived from brain levels at the 5 mg/kg/d dose that rescued memory deficits in FIGS. 3-5. Bars represent mean+sem.

CSF levels were compared across the dosage groups. There was variability within any one group, but clear dose dependency (FIG. 9). The increase in CSF level was greater than linear, with a three-fold increase from 50 to 100 and a two-fold increase from 100 to 125 mg, and this was consistent with an exponential relationship. The trough CSF at 50 mg saracatinib free base is 0.5 ng/ml to 1.2 ng/ml (i.e., 0.9-2.2 nM). The trough CSF at 100 mg saracatinib free base is 1.1 ng/ml to 4.5 ng/ml (i.e., 2.1-8.3 nM). The trough CSF at 125 mg saracatinib free base was 1.4 ng/ml to 7.6 ng/ml (i.e., 2.5-14.0 nM).

Using the ratio of CSF:Brain in mouse, the estimated human brain concentrations at 50 mg saracatinib free base is 3-7 nM, at 100 mg saracatinib free base is 7-27 nM and at 125 mg saracatinib free base is 8-46 nM.

Using the trough CSF levels described above and the correlation identified in FIG. 8, the corresponding free concentrations of saracatinib in the plasma for the dosing groups were 50 mg saracatinib free base: about 2.6-6.5 nM; 100 mg saracatinib free base: about 6.2-24.4 nM; and 125 mg saracatinib free base: about 7.4-41.2 nM.

As mentioned elsewhere herein, the Fyn $K_i$ for saracatinib is 5-10 nM. Moreover, the mouse trough CSF at a dose effective in rescuing memory for transgenic mice is 3.1 ng/ml to 7.6 ng/ml saracatinib free base (i.e., 5.8-14 nM). This value overlaps with the human 100 mg saracatinib free base levels and spans the human 125 mg saracatinib free base range (FIG. 9).

Example 4

The present study evaluates the role of Fyn inhibition in Tau-selective neurodegeneration using genetic and traumatic mouse models Chronic inhibition of Fyn kinase activity in transgenic P301S Tau mice prevented neuronal phospho-Tau accumulation, microglial activation and presynaptic marker loss. Memory function was preserved by Fyn inhibition. The traumatic model combined low-grade repeated closed head injury with chronic variable stress to produce persistent memory dysfunction. Inhibition of Fyn kinase beginning one day after a 2-week-long injury period, reduced memory deficits and phospho-Tau accumulation. Fyn kinase inhibition can thus limit pathophysiology and reduce clinical symptoms dependent from Tauopathy.

Selected results follow.

Fyn Inhibition Rescues Behavioral Deficits of Tau Transgenic Mice

Figure 11A:
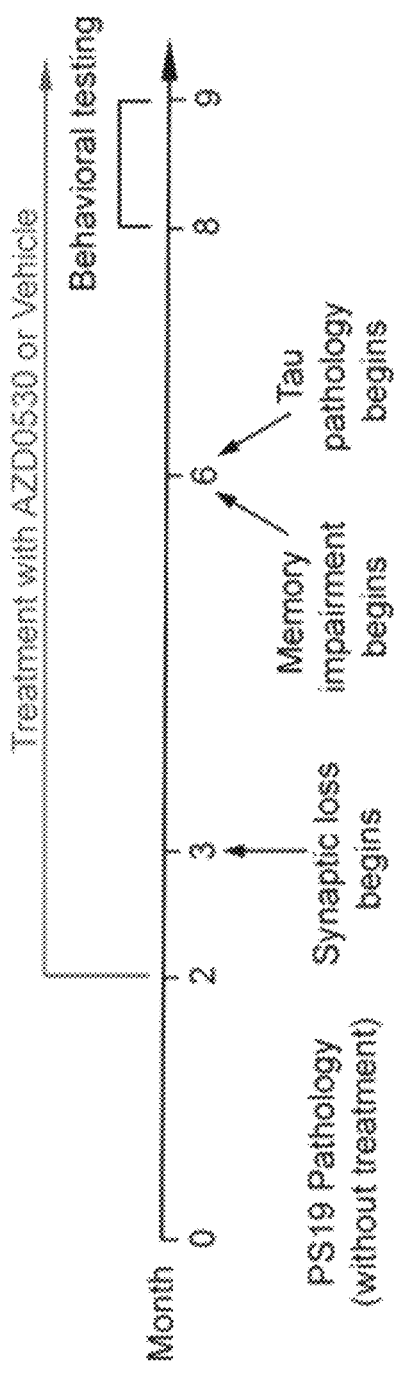
FIGS. 11A-11C illustrate that Fyn kinase inhibition prevents memory deficits in P301S Tau transgenic tice.

The PS19 transgenic strain is a commonly used mouse model of Tauopathy that expresses human 1N4R Tau with frontotemporal dementia-associated P301S mutation (Yoshiyama et al., 2007, Neuron 53:337-351). This PS19 model exhibits Tau pathology and recapitulates several phenotypes observed in human Tauopathies. Three-month-old PS19 mice begin to exhibit synaptic loss in the hippocampus, and at 6 months of age, cognitive impairments and Tau pathology have been observed ((Yoshiyama et al., 2007, Neuron 53:337-351). Thus, to test prophylactic effects of Fyn inhibition in the PS19 mice, cohorts of PS19 and WT mice were treated with Vehicle or AZD0530 starting at 2 months of age, prior to any Tau-associated pathology progression and treated chronically (FIG. 11A).

To provide chronic dosing of a Fyn kinase inhibitor to Tauopathy mice, mice were fed a diet of food pellets supplemented with AZD0530 at a dose calculated to achieve 5 mg/kg/d of active compound based on average consumption. Effectiveness of AZD0530 supplemented in the purified diet pellets in the brain was assessed using WT mice treated with AZD0530 or Vehicle for 9 months. Immunoblot analysis with phospho-Src (pY416) antibody using the RIPA-soluble fraction of hippocampus revealed a significant reduction in phosphorylation of Y416, a marker for activation of Src-family tyrosine kinase, in hippocampus of AZD0530-treated WT mice compared to that of Vehicle-treated WT mice (FIGS. 17A-17B). There was no difference in total Fyn levels between WT mice with and without AZD0530 treatment (FIG. 17C). Thus, AZD0530 formulated in diet pellets crosses the blood brain barrier and inhibits Fyn in the mouse brain.

Figure 11C:
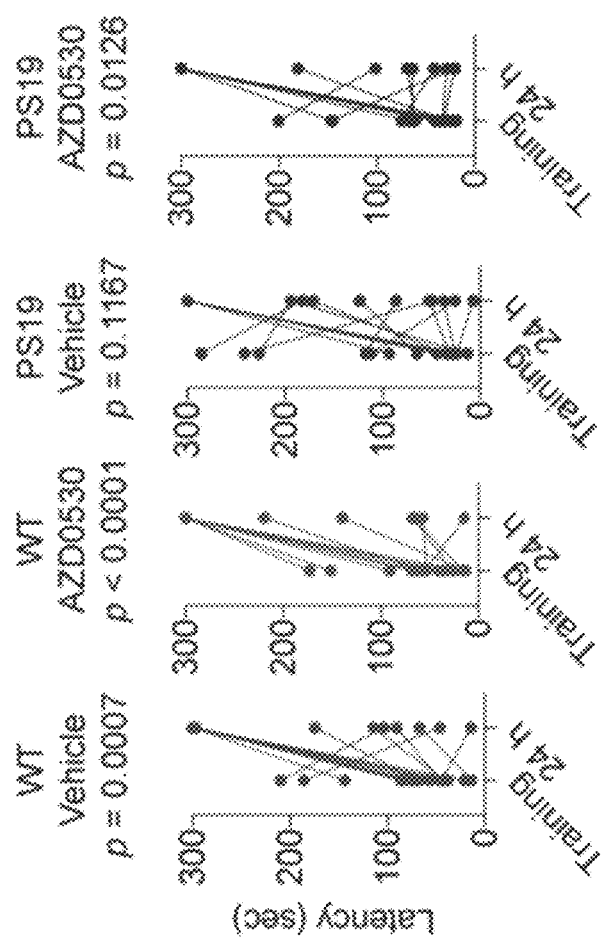
Figure 11B:
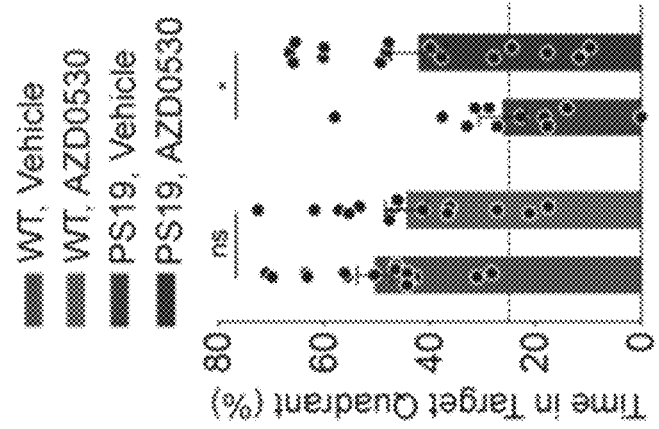

Spatial learning and memory of Vehicle and AZD-treated WT and PS19 mice at 8 months of age was assessed using the Morris water maze. In the forward and reverse learning trials, no statistically significant learning deficits were observed in the Vehicle-treated PS19 mice although the Vehicle-treated PS19 mice showed a trend to increase in the amount of time spent to reach the hidden platform in the reverse learning trial compared to AZD0530-treated PS19 mice and both WT groups (FIGS. 18A-18B). However, in the probe trial after the reverse learning trial, the Vehicle-treated PS19 mice significantly spent less time in the target quadrant than their WT littermates, exhibiting a memory deficit (FIG. 11B). Notably, AZD0530 treatment significantly improved the memory deficit in PS19 mice (FIG. 11B). Although a slight increase in the time to reach the platform was observed in Vehicle-treated PS19 mice in the visible platform trial, no motor impairment was observed in 8-month-old PS19 mice in the Rotarod test (FIGS. 18C-18D).

Fear-associated learning for the same cohorts of mice was also tested using passive avoidance test, where mice were placed inside a light-filled box with a door to a dark box and mice that crossed over to the dark box are given a mild foot shock. While both groups of WT mice and the AZD0530-treated PS19 mice exhibited passive avoidance at 24 hours after association of the foot shock with the dark box, the Vehicle-treated PS19 mice did not learn to associate the dark box with the foot shock (FIG. 11C). Together, these data demonstrate that chronic AZD0530 treatment prevents cognitive impairments in PS19 mice at 8 months of age.

Accumulation of phospho-Tau is Reduced by AZD0530

Without wishing to be limited by any theory, an explanation for improved function is reduced accumulation of transgene-dependent Tau as a result of Fyn inhibition. It was examined whether AZD0530 treatment reduces Tau pathology in PS19 mice at 9 months of age. Immunohistochemistry using the AT8 antibody directed against phospho-Tau (Ser202/Thr205) showed a significant increase in AT8 immunoreactivity in the dentate gyrus (DG) and CA1 areas of hippocampus of PS19 mice compared to WT mice (FIGS. 12A-12D). Strikingly, chronic AZD0530 treatment significantly mitigates the increase in AT8 immunoreactivity in PS19 mice. Similarly, immunostaining using PHF1 antibody directed against phospho-Tau (Ser396/Ser404) revealed a significant decrease in PHF-1-immunoreactive area in the CA1 area of hippocampus of AZD0530-treated PS19 mice compared to Vehicle-treated PS19 mice (FIGS. 12E-12F). These results indicate that chronic inhibition of Fyn by AZD0530 treatment reduces phospho-Tau pathology in hippocampus of PS19 mice.

Tau Transgene-Induced Gliosis is Lessened by Fyn Inhibition

Figure 13A:
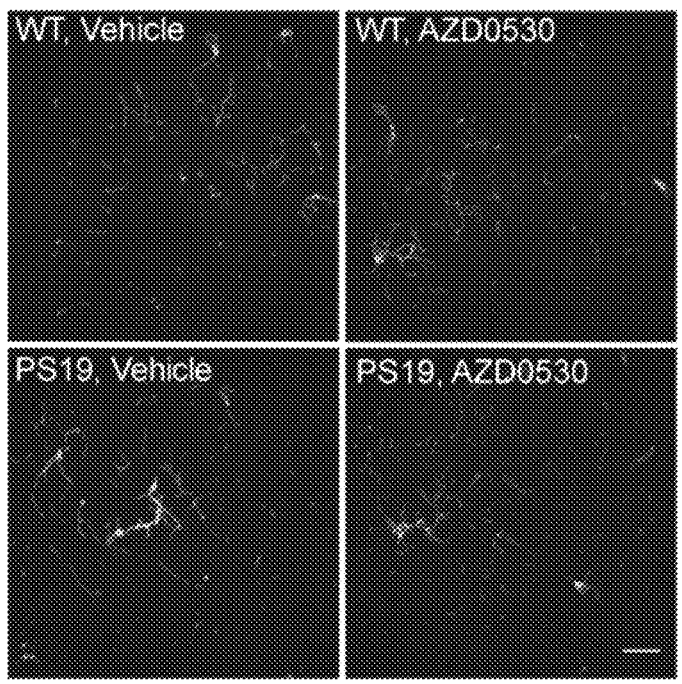
Figure 13C:
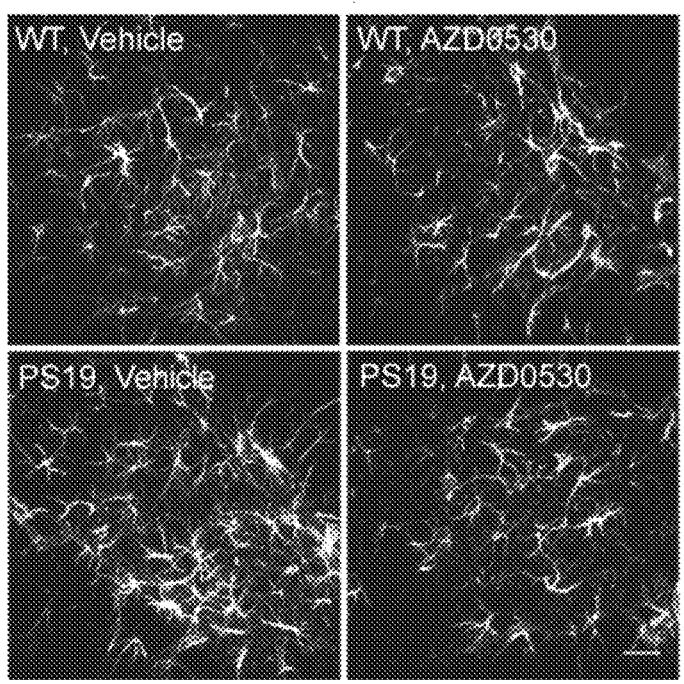

Pathological Tau induces neuroinflammation leading to synaptic deficits in PS19 mice. The effect of AZD0530 treatment on neuroinflammation in PS19 mice was examined using anti-Iba1 and GFAP antibodies, general makers for microgliosis and astrocytosis, respectively. At 9 months of age, despite an evident increase in Tau pathology, a significant increase in Iba1 or GFAP immunoreactivities in hippocampus of PS19 mice was observed under a low magnification condition (FIGS. 19A-19D). Subareas (i.e. the CA1, CA3, and DG areas) of hippocampus were analyzed using high-resolution spinning disc confocal microscopy. While there was no difference in Iba1-immunoreactivity between WT and PS19 mice even in these areas, co-immunostaining using an antibody against CD68, a maker for activated microglia, revealed a significant increase in CD68-immunoreactivity in Iba1-immunoreactive area of the CA3 area of hippocampus in PS19 mice. Consistent with the results showing a reduction in Tau pathology, AZD0530 treatment almost completely prevented the increase in CD68 immunoreactivity in PS19 mice (FIGS. 13A-13B). By using high-resolution imaging, a moderate but significant increase in GFAP-immunoreactive area was also found in dentate gyrus, but not the other areas, of hippocampus of Vehicle-treated PS19 mice at 9 months of age. Importantly, AZD0530 treatment also significantly attenuated the astrocytosis in PS19 mice (FIGS. 13C-13D). These results indicate that AZD0530 treatment prevents neuroinflammation in the hippocampus of PS19 mice.

Synapse Loss in PS19 Transgenics is Prevented by AZD0530

To further investigate the mechanisms by which AZD0530 treatment rescues behavioral deficits in PS19 mice, the effects of AZD0530 treatment on presynaptic degeneration observed in PS19 mice were examined. There was a significant reduction in immunoreactivity of SV2A, a presynaptic protein, in the CA3 area of hippocampus of PS19 mice compared to that of WT mice at 9 months of age (FIGS. 14A-14B). AZD0530 treatment fully rescued the reduction in SV2A immunoreactivity in the CA3 area of hippocampus of PS19 mice (FIGS. 14A-14B). Thus, chronic Fyn kinase inhibition prevents phospho-Tau accumulation, gliosis and synapse loss, allowing improved memory function in this model.

Fyn Inhibition Improves Memory Function in Mild TBI/Stress Model

Having observed a benefit of Fyn inhibition in the PS19 transgenic model, analysis was extended to a traumatic Tauopathy. In order to mimic conditions resembling those related to combat and those associated with CTE, mice were exposed to daily mild closed head injury and chronic variable stress for 14 consecutive days. The parasagittal injury site alternated right to left on different days. Preliminary work demonstrated that the exposure to injury plus stress is synergistic in establishing persistent neurological deficit. At the end of the 14 day induction period, motor deficits were minimal, as revealed by Rotarod performance indistinguishable from the Sham group, which received similar extent of handling and anesthesia (FIGS. 15A-15B). This demonstrates the mild nature of the injury paradigm.

Figure 15F:
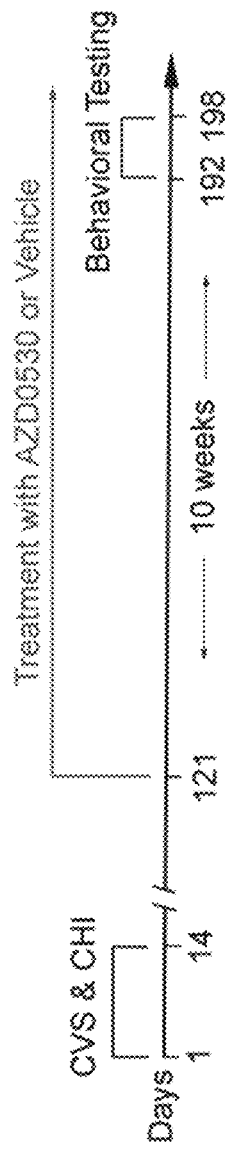
Figure 15G:
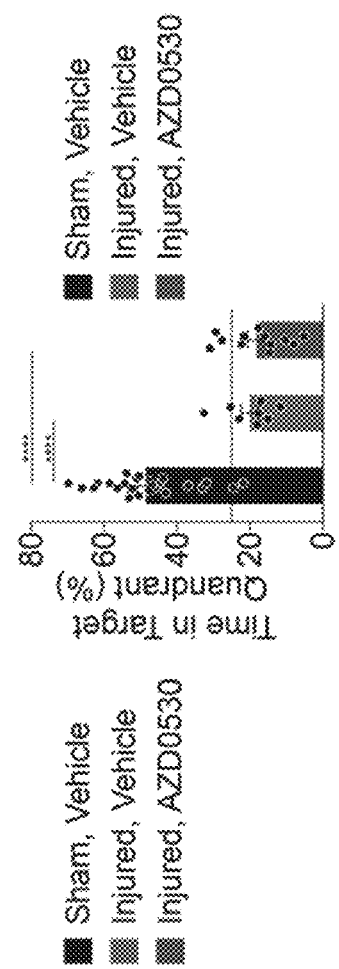

The first experimental subacute group received 5 mg/kg/day of AZD0530 or Vehicle beginning 24 hours after the final day of injury on Day 15 for a period of 10 weeks (FIGS. 15A & 15G). The daily dose was divided into twice a day oral gavage administration. While still receiving AZD0530 treatment or Vehicle, learning and memory were assessed. The Injured Vehicle group had profound deficits in novel object recognition test with no ability to distinguish novel versus familiar objects as opposed to Sham mice with a robust preference for novel objects (FIG. 15C). The Injured AZD0530 group recognized familiar objects as successfully as Sham Vehicle mice (FIG. 15C). Spatial learning and memory were assessed as described for PS19 mice. Despite the lack of a motor deficit, the Injured Vehicle group failed to learn the hidden platform location over 6 blocks of 4 swim trials, and was significantly impaired relative to Sham Vehicle mice (FIG. 15D). During a probe trial, one day after the learning trials, the Injured Vehicle group showed no evidence of memory for the platform location and performed at chance levels (FIG. 15E). The Injured mice treated with AZD0530 continued to show severely impaired learning relative to Sham Vehicle (FIG. 15D), but exhibited probe trial memory for the platform location that was not statistically distinguishable from Sham Vehicle (FIG. 15E). Thus, AZD0530 treatment beginning 24 hours after the 2-week injury epoch, fully rescued novel object recognition memory and partially rescued spatial memory performance.

Figure 15H:
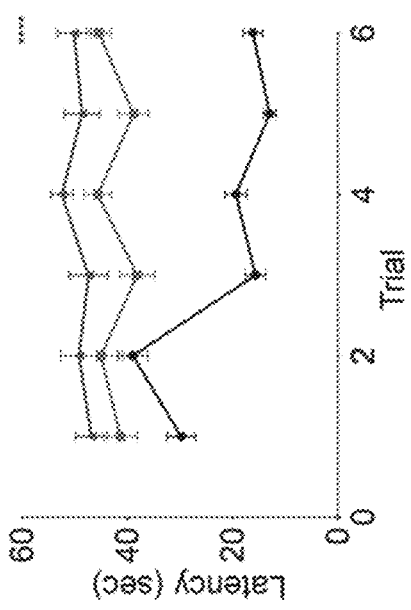
Figure 19A:
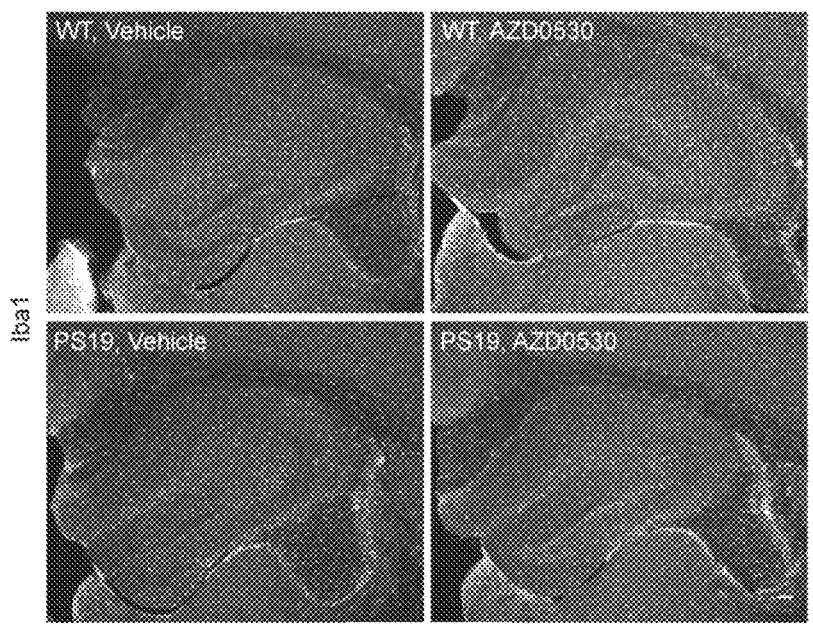
FIGS. 19A-19D illustrate low magnification survey of gliosis in PS19 mice unaffected by AZD0530.
Figure 19B:
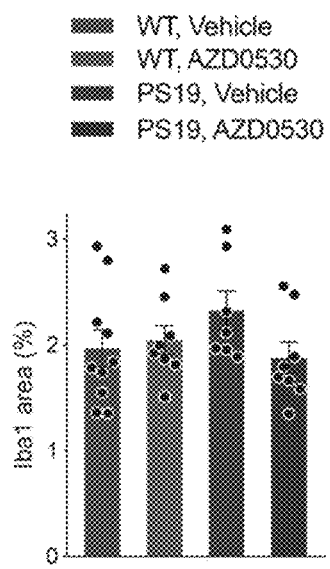
Figure 19C:
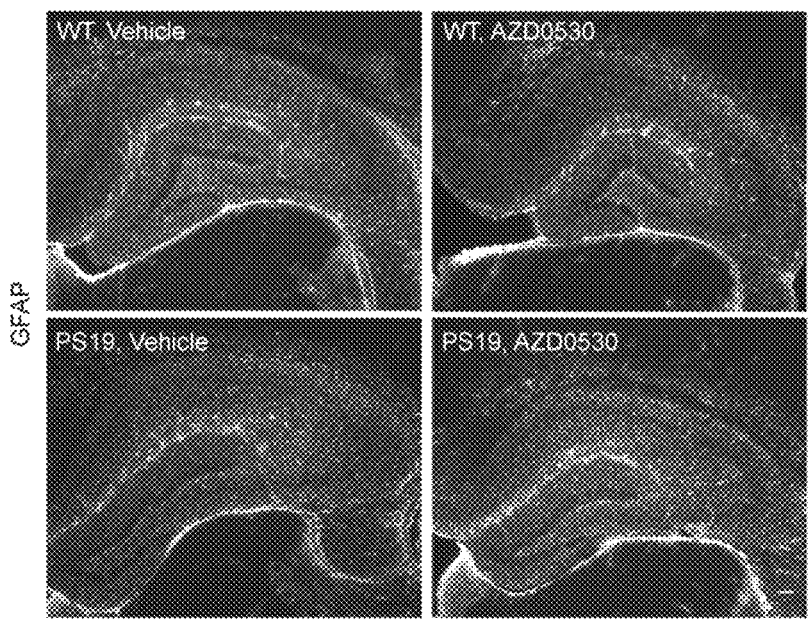
Figure 19D:
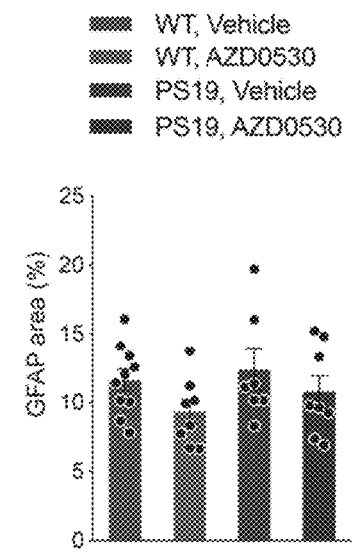

It was considered whether the benefit of Fyn kinase might extend to chronic injury conditions. A second group of mice received AZD0530 treatment beginning on Day 121, 107 days after the final day of injury for 10 weeks (FIG. 15F). Spatial learning and memory deficits in the Injured Vehicle group remained pronounced more than 4 months post injury reflecting the chronic nature of this model (FIGS. 15G-15H). As compared to the first cohort, for which treatment began one day after the 2-week injury period, there was no evidence of improved memory in the probe trial of the Morris water maze after the learning trials (FIG. 15H). It was concluded that the benefit of Fyn kinase inhibition in this model of combined TBI/Stress is limited to the subacute post-injury phase.

AZD0530 Treatment Reduces Tauopathy After Trauma

In the PS19 transgenic model, the benefit of AZD0530 treatment correlated with reduced phospho-Tau accumulation histologically. Tissue from the subacute TBI/Stress mice was examined by PHF-1 immunostaining in the cerebral cortex 0.5-1.0 mm medial to the injury site. PHF-1 immunoreactivity area was significantly increased in the Injured Vehicle group compared to the Sham Vehicle group. Similar to the results from the PS19 transgenic experiment, the AZD0503 injury samples exhibited dramatically reduced PHF-1 immunoreactivity area (FIGS. 16A-16B). In contrast, total Tau immunoreactivity area was not altered by injury or Fyn inhibitor treatment (FIGS. 16C-16D). Astrogliosis was also examined by anti-GFAP staining in the perilesional area (FIGS. 16E-16F). While variable gliosis was detected in some samples from these cohorts, there was no significant difference between Injured and Sham groups, reflecting the minor and chronic nature of the analysis.

Comments

One finding of the present study is the ability of Fyn kinase inhibition to prevent Tau accumulation and memory deficits in both transgenic and traumatic models of Tauopathy in mice. In the P301 S model, long term treatment initiated in early adulthood reduced subsequent gliosis and synaptic loss as well as phospho-Tau accumulation, and allowed preservation of learning and memory performance over 6 months. The traumatic model combined repeated head trauma with chronic variable stress to create persistent learning and memory deficits with no detectable motor impairment. In this mild trauma plus stress model, post-injury Fyn inhibition reduced focal phospho-Tau accumulation, fully rescuing object recognition and improving spatial memory function.

Blocking Fyn kinase activation with AZD0530 reduces autophosphorylation of the enzyme in the activation loop, and the conformational changes associated with enzyme activation are prevented. In this way, the inhibition of kinase activity with the ATP-competitive inhibitor AZD0530 prevents both phosphorylation and protein interactions dependent on the activated enzyme conformation. Tau is both a binding partner and a substrate of Fyn kinase. Occupancy with AZD0530 has the potential to reduce both phosphorylation of Fyn substrates as well as complex formation with Fyn partners. Tau accumulation is accompanied by phosphorylation of Ser/Thr residues introduced by other kinases, and common pathology-associated epitopes include Ser202/Thr205 detected by AT8 and Ser396/Ser404 detected by PHF-1. The reduction of these epitopes is an indirect result of Fyn kinase inhibition. Without wishing to be limited by any theory, the change in Ser/Thr phosphorylation and accumulation can be due to altered Tyr18 phosphorylation, or more likely to altered Fyn/Tau binding with shifted subcellular localization and changed access to Ser/Thr kinases. In certain embodiments, there is no change in PY18 Tau levels in AZD0530-treated PS19 samples despite reduction in AT8 and PHF-1 accumulation, and in WT mice with or without trauma, this phospho epitope is not detectable. The net result of Fyn kinase inhibition is reduced Ser/Thr phosphorylation and accumulation of Tau.

The clinical history for cases of CTE, and PTSD in combat veterans, typically includes both mild repetitive head injury and stress. A progressive Tauopathy with devastating behavioral and cognitive deficits has been described (Fesharaki-Zadeh et al., 2019, Front Neurol 10:713). This condition was modeled by combining daily mild closed head injury with chronic variable stress in mice over 2 weeks. It is clear that this paradigm produces profound learning and memory deficits and includes accumulation of phospho-Tau epitopes. Much like the clinical conditions, there is minimal if any motor dysfunction. In this mild head trauma plus stress model, Fyn kinase inhibition rescued object recognition memory deficits and reduced spatial memory deficits.

An important aspect of any potential therapeutic intervention is its timing relative to disease diagnosis, symptoms and progression. In the PS19 transgenic model, the Fyn kinase benefit was observed in a prophylactic mode prior to the onset of Tau accumulation. For the mild TBI/Stress model, treatment was initiated a full 24 hours after the 2 week injury/stress paradigm was complete in a therapeutic mode, and d robust benefit was observed. However, the time window for effective Fyn kinase intervention does not appear open-ended, since treatment initiated 3-4 months after the injury period did not reverse well established deficits.

It is clear from these studies that modulating the activation state of a Tau partner, Fyn kinase, alters the course of both genetic and traumatic Tauopathy. Specifically, reducing Fyn activation leads to less phospho-Tau accumulation, with a normalization of glial activity, synaptic density and memory function. Moreover, effective intervention can be achieved even when delayed by a full 24 hours after an extended 2 week trauma/stress exposure. The present studies establish the benefit of Fyn kinase inhibition in Tauopathy conditions.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating, ameliorating, or inhibiting further development of a Tauopathy in a mammal in need thereof, the method comprising administering to the mammal a therapeutically effective amount of a Fyn inhibitor,
   wherein the Fyn inhibitor is saracatinib, or a pharmaceutically acceptable salt thereof;
   wherein the Tauopathy is selected from the group consisting of traumatic brain injury, fronto-temporal dementia, after stroke aphasia, and any combinations thereof.

2. The method of claim 1, wherein accumulation of hyperphosphorylated Tau protein is reversed, inhibited, or minimized in the mammal.

3. The method of claim 1, wherein the Fyn inhibitor is selected from the group consisting of saracatinib free base, saracatinib difumarate, and any combinations thereof.

4. The method of claim 1, wherein the mammal is human.

5. The method of claim 1, wherein the inhibitor is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

6. The method of claim 1, further comprising administering to the mammal at least one additional agent that treats, ameliorates, or inhibits further development of the Tauopathy in the mammal.

7. The method of claim 6, wherein the inhibitor and at least one additional agent are coformulated.

8. A method of improving memory, ameliorating loss of memory, or preventing further loss of memory in a mammal afflicted with a Tauopathy, the method comprising administering to the mammal a therapeutically effective amount of a Fyn inhibitor,
   wherein the Fyn inhibitor is saracatinib, or a pharmaceutically acceptable salt thereof;
   wherein the Tauopathy is selected from the group consisting of traumatic brain injury, fronto-temporal dementia, after stroke aphasia, and any combinations thereof.

9. The method of claim 8, wherein the Fyn inhibitor is selected from the group consisting of saracatinib free base, saracatinib difumarate, and any combinations thereof.

10. The method of claim 8, wherein the inhibitor is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

11. A method of treating, ameliorating, or preventing further development of at least one of hyperphosphorylated Tau accumulation, synapse loss, and memory deficit in a mammal afflicted with traumatic brain injury,
   the method comprising administering to the mammal a therapeutically effective amount of a Fyn inhibitor after the mammal suffers the traumatic brain injury;
   wherein the Fyn inhibitor is saracatinib, or a pharmaceutically acceptable salt thereof.

12. The method of claim 11, wherein the administering minimizes, reduces, or reverses at least one of gliosis, neurodegeneration, and neurological function deficits in the afflicted mammal.

13. The method of claim 11, wherein the administering takes place 16 weeks or less after the traumatic brain injury.

14. The method of claim 13, wherein the administering takes place 1 day or less after the traumatic brain injury.

15. The method of claim 11, wherein the Fyn inhibitor is selected from the group consisting of saracatinib free base, saracatinib difumarate, and any combinations thereof.

16. The method of claim 11, wherein the inhibitor is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

* * * * *